United States Patent
Kemp et al.

(10) Patent No.: US 10,654,853 B2
(45) Date of Patent: May 19, 2020

(54) SPIRO-CONDENSED PYRROLIDINE DERIVATIVES AS DEUBIQUITYLATING ENZYMES (DUB) INHIBITORS

(71) Applicant: MISSION THERAPEUTICS LIMITED, Cambridge (GB)

(72) Inventors: Mark Ian Kemp, Cambridge (GB); Martin Lee Stockley, Cambridge (GB); Michael David Woodrow, Cambridge (GB); Alison Jones, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 16/078,518

(22) PCT Filed: Mar. 2, 2017

(86) PCT No.: PCT/GB2017/050565
§ 371 (c)(1),
(2) Date: Aug. 21, 2018

(87) PCT Pub. No.: WO2017/149313
PCT Pub. Date: Sep. 8, 2017

(65) Prior Publication Data
US 2019/0048008 A1   Feb. 14, 2019

(30) Foreign Application Priority Data
Mar. 4, 2016 (GB) .................................. 1603779.8

(51) Int. Cl.
*C07D 471/10* (2006.01)
*C07D 471/20* (2006.01)
*C07D 498/20* (2006.01)
*C07D 487/10* (2006.01)

(52) U.S. Cl.
CPC ......... *C07D 471/10* (2013.01); *C07D 471/20* (2013.01); *C07D 487/10* (2013.01); *C07D 498/20* (2013.01)

(58) Field of Classification Search
CPC .. C07D 471/10; C07D 471/20; C07D 487/10; C07D 498/20
See application file for complete search history.

(56) References Cited

U.S. PATENT DOCUMENTS

2006/0211757 A1   9/2006   Wang et al.
2012/0264738 A1   10/2012  Sugimoto et al.

FOREIGN PATENT DOCUMENTS

| EP | 2752191 A1 | 7/2014 |
|---|---|---|
| WO | 0177073 A1 | 10/2001 |
| WO | 2008036168 A2 | 3/2008 |
| WO | 2008144507 A2 | 11/2008 |
| WO | 2009026197 A1 | 2/2009 |
| WO | 2016/046530 A1 | 3/2016 |
| WO | 2016156816 A1 | 10/2016 |
| WO | 2017/009650 A1 | 1/2017 |
| WO | 2017/093718 A1 | 6/2017 |
| WO | 2017/109488 A1 | 6/2017 |
| WO | 2017103614 A1 | 6/2017 |
| WO | 2017141036 A1 | 8/2017 |
| WO | 2017/158381 A1 | 9/2017 |
| WO | 2017/158388 A1 | 9/2017 |
| WO | 2017/163078 A1 | 9/2017 |
| WO | 2018060689 A1 | 4/2018 |
| WO | 2018060691 A1 | 4/2018 |
| WO | 2018060742 A1 | 4/2018 |
| WO | 2018065768 A1 | 4/2018 |

OTHER PUBLICATIONS

Kubinyi (3D QSAR in Drug Design: Ligand-Protein Interactions and Molecular Similarity, vol. 2-3, Springer, 1998, p. 243.*
Wermuth, The Practice of Medicinal Chemsitry, 2d ed. (2003), p. 142.*
Ohayon et al. (J. Am. Chem. Soc. 2012, 134(6); 3281-3289.*
Ward et al., "Quantitative Chemical Proteomic Profiling of Ubiquitin Specific Proteases in Intact Cancer Cells," ACS Chem. Biol. 2016, 11, 3268-3272.
The International Search Report and Written Opinion, dated Apr. 20, 2017, in the corresponding PCT Appl. No. PCT/GB2017/050565.
Falgueyret et al., "Novel, Nonpeptidic Cyanamides as Potent and Reversible Inhibitors of Human Cathepsins K and L," J. Med. Chem. 2001, 44, 94-104.
Laine et al., "Discovery of Novel Cyanamide-Based Inhibitors of Cathepsin C," ACS Med. Chem. Lett. 2011, 2, 142-147.
Komander et al., "Breaking the chains: structure and function of the deubiquitinases," Nat Rev Mol Cell Biol. Aug. 2009;10(8):550-63.
Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.
Deaton et al, "Novel and potent cyclic cyanamide-based cathepsin K inhibitors", Bioorganic & Medicinal Chemistry Letters 15 (2005) 1815-1819.
Oballa et al, "A generally applicable method for assessing the electrophilicity and reactivity of diverse nitrile-containing compounds", Bioorganic & Medicinal Chemistry Letters 17 (2007) 998-1002.

(Continued)

Primary Examiner — Valerie Rodriguez-Garcia

(57) ABSTRACT

The present invention relates to novel compounds and methods for the manufacture of inhibitors of deubiquitylating enzymes (DUBs). In particular, the invention relates to the inhibition of Cezanne 1. The invention further relates to the use of DUB inhibitors in the treatment of cancer.

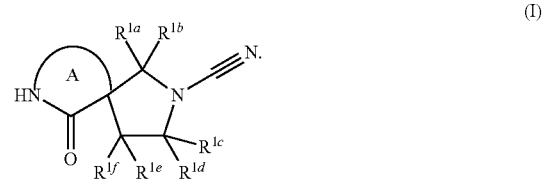

10 Claims, 1 Drawing Sheet

(56) References Cited

OTHER PUBLICATIONS

Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.

Shimrit Ohayon et al, "Targeting Deubiquitinases Enabled by Chemical Synthesis of Proteins", J. American Chemical Society, 134(6), pp. 3281-3289, Feb. 2012.

Zheng et al, "Heterogeneous expression and biological function of ubiquitin carboxy-terminal hydrolase-L1 in osteosarcoma", Cancer Letters, 359, pp. 36-46, Apr. 1, 2015.

Pareja et al, "Deubiquitination of EGFR by Cezanne-1 contributes to cancer progression", Oncogene. Oct. 25, 2012; 31(43): 4599-4608.

Hu et al, "Otud7b facilitates T cell activation and inflammatory responses by regulating Zap70 ubiquitination", The Journal of Experimental Medicine, 2016, 213(3), pp. 399-414.

* cited by examiner

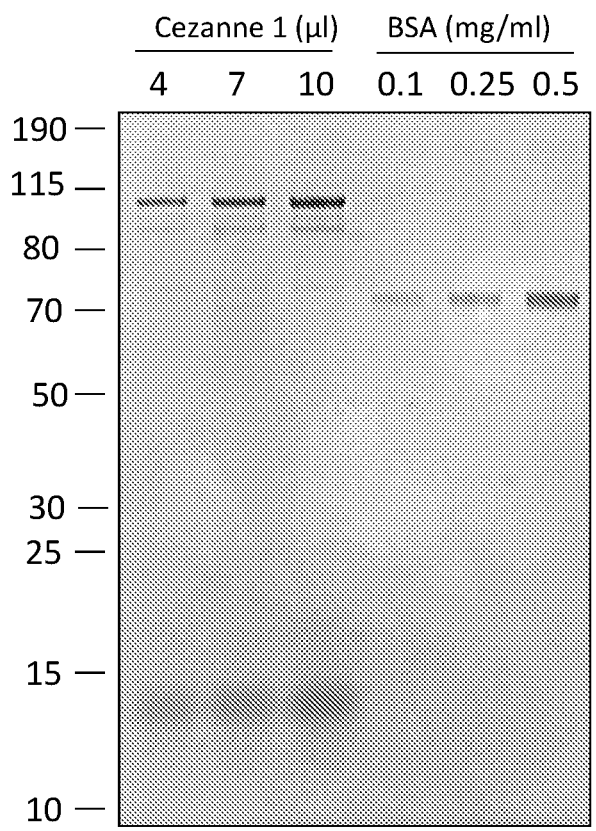
Figure 1: Expression and purification of FLAG-Cezanne 1 from mammalian cells
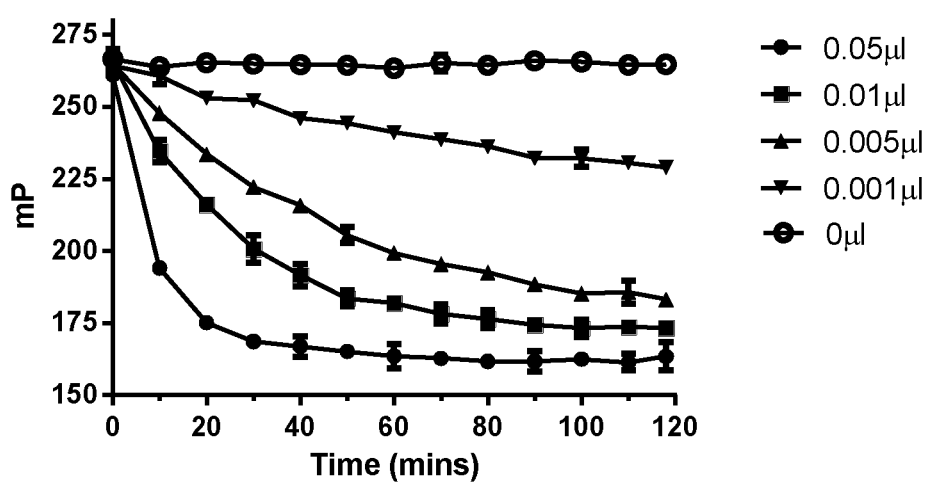
Figure 2: Cezanne 1 kinetic assay for high throughput screening of compounds using an isopeptide linked substrate

SPIRO-CONDENSED PYRROLIDINE DERIVATIVES AS DEUBIQUITYLATING ENZYMES (DUB) INHIBITORS

CROSS-REFERENCE TO RELATED APPLICATIONS

This application is a National Stage Application of PCT/GB2017/050565 filed Mar. 2, 2017, which claims priority from UK Patent Application No. 1603779.8, filed on Mar. 4, 2016. The priority of said PCT and UK Patent Application are claimed. Each of the prior mentioned applications is hereby incorporated by reference herein in its entirety.

The present invention relates to novel compounds and methods for the manufacture of inhibitors of deubiquitylating enzymes (DUBs). In particular, the invention relates to the inhibition of Cezanne 1. The invention further relates to the use of DUB inhibitors in the treatment of cancer.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein. These processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin molecules are cleaved from proteins by deubiquitylating enzymes (DUBs), of which there are approximately 95 DUBs in human cells, divided into sub-families based on sequence homology. The ovarian tumour (OTU) family consists of at least 14 active DUBs and are characterised by the presence of an OTU domain and the tendency to cleave ubiquitin chains in a linkage specific manner. Cezanne 1, also known as OTUD7B, is an 843 amino acid protein that was identified owing to its similarity to the OTU family member A20 that has been shown biochemically to have a strong preference for K11 ubiquitin chain linkages.

Cezanne 1 has been shown to act as a negative regulator of both the canonical and the non-canonical NF-κB pathway. It has been shown that Cezanne 1 acts on the canonical pathway by processing K63 chains on the RIP1 protein and on the non-canonical pathway by deubiquitylation of the inhibitory component TRAF3 (TNF receptor associated factor 3). It has also been shown to have a role in hypoxia by regulating HIF1α (hypoxia inducible factor 1α) protein levels. Cezanne 1 siRNA decreased HIF1α protein levels under hypoxia, and accordingly decreased HIF1α target gene expression. Knockdown of Cezanne 1 led to higher levels of apoptosis following hypoxia. Since HIF1α has oncogenic properties, and Cezanne 1 has a pro-survival role in hypoxia, Cezanne 1 has been suggested to be a good target for pharmacological intervention.

Cezanne 1 has been shown to facilitate T cell activation and inflammatory responses by regulating ZAP70 ubiquitination (Hu et al 2016 Journal of Exploratory Medicine). This shows that inhibition of Cezanne 1 would lead to a reduction in inflammatory response. There is a continued need for compounds which inhibit DUBs such as Cezanne for the treatment of inflammation.

Cezanne 1 has been shown to have a role in cell proliferation, migration and invasion by antagonizing EGFR (epidermal growth factor receptor) internalisation and degradation. Cezanne 1 and Cezanne 2 were identified in a genetic screen to find a DUB enzyme for EGFR. Cezanne 1 overexpression led to higher levels of phosphorylated EGFR, lower levels of ubiquitylated EGFR and EGFR stabilization. In MDA-MB-231 breast cancer cells, knockdown of Cezanne 1 led to decreased invasion and migration. Analysis of The Cancer Genome Atlas by Pareja et al. (2012) showed that Cezanne 1 was overexpressed in breast cancer and amplification of the gene was seen in a third of breast tumours. The level of Cezanne 1 expression correlated with poor prognosis. Although there has been a handful of DUB inhibitors published in the literature, there is a continuing need for compounds and pharmaceutical compositions which inhibit DUBs such as Cezanne 1 and USP30 for the treatment of cancer or other indications where DUB activity is observed.

SUMMARY OF THE INVENTION

In accordance with a first aspect of the invention there is provided a compound of formula (I)

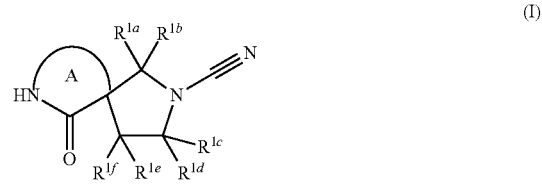

(I)

or a pharmaceutically acceptable salt thereof, wherein:
$R^{1a}$, $R^{1b}$, $R^{1c}$ and $R^{1d}$ each independently represent hydrogen or an optionally substituted $C_1$-$C_6$ alkyl, or $R^{1a}$ and $R^{1b}$ together form an optionally substituted cycloalkyl ring, $R^{1c}$ and $R^{1d}$ together form an optionally substituted cycloalkyl ring, or $R^{1d}$ together with $R^{1e}$ forms an optionally substituted cycloalkyl ring;

$R^{1e}$ and $R^{1f}$ each independently represent hydrogen, fluorine, cyano, hydroxyl, amino, optionally substituted $C_1$-$C_6$ alkyl, optionally substituted $C_1$-$C_6$ alkoxy or an optionally substituted 5 or 6 membered heteroaryl or aryl ring, or $R^{1e}$ forms an optionally substituted cycloalkyl ring with $R^{1f}$ or $R^{1d}$;

ring A is a 5 to 11 membered monocyclic or bicyclic heterocyclyl ring which may be optionally further substituted.

In one aspect, the invention also relates to pharmaceutical compositions comprising the compounds of the present invention and one or more pharmaceutically acceptable excipients.

In another aspect, the compounds of the invention are useful for the treatment of cancer.

BRIEF DESCRIPTION OF THE FIGURES

FIG. 1 provides an image of Cezanne 1 purified from mammalian cells. FLAG-purified protein or the indicated concentrations of BSA were separated by SDS-PAGE and stained with Imperial protein stain (Pierce Biotechnology).

FIG. 2 is a graph showing proteolytic activity of Cezanne 1 measured using a fluorescence polarisation assay. Various volumes of purified Cezanne 1 as indicated were incubated with a TAMRA labelled peptide linked to ubiquitin via an isopeptide bond.

DETAILED DESCRIPTION OF THE INVENTION

The definitions and explanations below are for the terms as used throughout this entire document including both the specification and the claims. Reference to compounds as described herein (e.g. a compound of Formula I), includes reference to Formula I and II including any sub-generic embodiments thereof.

Where any group of the compounds of formula I have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkylene, alkoxy, alkenyl, or alkynyl substituent (or linker) group or an alkyl, alkenyl moiety in a substituent group may be linear or branched. Alkyl, alkylene and alkenyl chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^{1a}$, $R^{1b}$, $R^{1c}$, $R^{1d}$, $R^{1e}$, $R^{1f}$, $R^3$, $R^4$, $R^{4a}$, $R^6$, $R^7$, $R^{7a}$, $Q^1$, and within the definition of substituents for $R^2$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, —$C_1$-$C_6$ alkylene, $C_1$-$C_4$ alkylene and $C_1$-$C_3$ alkylene within the definitions of $R^5$, $Q^1$, $Q^{2a}$, $Q^{2b}$ and $Q^{2c}$ may be unsubstituted or substituted with one or more of the substituents defined herein.

$C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl within the definitions of $Q^1$ and within the definition of substituents for $R^2$, may be unsubstituted or substituted with one or more of the substituents defined herein.

$C_2$-$C_6$ alkenylene refers to linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene within the definitions of $Q^1$, $Q^{2a}$, $Q^{2b}$ and $Q^{2c}$ may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definitions of $Q^1$ and within the definition of substituents for $R^2$, may be unsubstituted or substituted with one or more of the substituents defined herein.

$C_1$-$C_6$ alkoxy refers to a group or part of a group having an —O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, isopropoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, —$CH_2CH_2OCH_3$, or alternatively, the alkoxy is linked through oxygen to the remainder of the molecule, for example —$OC_{1-6}$ alkyl. In one instances, the alkoxy is linked through oxygen to the remainder of the molecule but the alkoxy group contains a further oxygen atom, for example $OCH_2CH_2OCH_3$. Unless specified otherwise, —$C_1$-$C_6$ alkoxy and $C_1$-$C_3$ alkoxy within the definitions $R^{1e}$, $R^{1f}$, $Q^1$, and within the definition of substituents for $R^2$, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_2CH_3$.

The term "halogen" or "halo" refers to chlorine, bromine, fluorine or iodine atoms, in particular chlorine or fluorine atoms.

The term "oxo" means =O.

The term "amino" means NR'R" wherein R' and R" each independently represent hydrogen or $C_1$-$C_3$ alkyl.

The term "amido" means C(O)NR'R" wherein R' and R" each independently represent hydrogen or $C_1$-$C_3$ alkyl.

For the avoidance of doubt it will be understood that the cycloalkyl, heterocyclyl, aryl and heteroaryl rings disclosed herein and within the definitions of $R^2$, $R^8$, ring A, do not include any unstable ring structures or, in the case of heteroaryl and heterocyclic rings systems, any O—O, O—S or S—S bonds. The ring systems may be monocyclic or bicyclic. Bicyclic ring systems include bridged, fused and spiro ring systems. A substituent if present may be attached to any suitable ring atom which may be a carbon atom or, in the case of heteroaryl and heterocyclic ring systems, a heteroatom. Substitution on a ring may also include a change in the ring atom at the position of the substitution. For example, substitution on a phenyl ring may include a change in the ring atom at the position of substitution from carbon to nitrogen, resulting in a pyridine ring.

"cycloalkyl" refers to a monocyclic saturated or partially unsaturated, non-aromatic ring, wherein all of the ring atoms are carbon, and having the number of ring atoms as indicated. For example $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^{1a}$, $R^{1b}$, $R^{1c}$, $R^{1d}$, $R^{1e}$, $R^{1f}$, $R^2$, $R^8$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably phenyl. Unless specified otherwise, aryl within the definitions of $R^{1e}$, $R^{1f}$, $R^2$, $R^8$, may be unsubstituted or substituted with one or more of the substituents defined herein.

"Heteroaryl" as used herein means a polyunsaturated, monocyclic or bicyclic 5 to 10 membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulphur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. In one example, a bicyclic heteroaryl is one in which the entire fused ring system is aromatic. A bicyclic heteroaryl can have the at least one heteroatom in either of the fused rings. For example, a bicyclic ring with an aromatic ring fused to a partially saturated ring may contain the at least one heteroatom in the aromatic ring or the partially saturate ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). In instances where ring A is a heteroaryl, the ring is an aromatic ring and may be fused to a further aromatic or partially saturated ring. Examples include pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, indolinyl, purinyl, furazanyl, imidazolyl, indazolyl, isothiazolyl, isoxazolyl, oxadiazolyl, oxazinanyl, tetrazolyl, thiadiazolyl, benzofuranyl, isobenzofuranyl, tetrahydrofuranyl, benzothiophenyl, isobenzothiophenyl, benzimidazolyl, benzothiazolyl, napthyridinyl, pteridinyl, pyrazinyl, 4H-quinolizinyl, quinolinyl, isoquinolinyl, cinnolinyl, phthalazinyl, quinazolinyl, imidazopyridinyl, pyrazolopyridinyl, thiazolopyridinyl, indolinyl, isoindolinyl, triazinyl, dihydrophyridinyl, quinoxalinyl and dihydrobenzoxazinyl. Unless specified otherwise, heteroaryl within the definitions of $R^{1e}$, $R^{1f}$, $R^2$, $R^8$, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members, where at least one member and up to 5 members, particularly 1, 2 or 3 members of the ring are heteroatoms selected from e.g., N, O and S and the remaining ring atoms are carbon atoms, in stable combinations known to those of skill in the art. Heterocyclic ring nitrogen and sulphur atoms are optionally oxidised, and the nitrogen atoms(s) are optionally quaternized. As used herein, the heterocyclic ring may be a fused ring to another ring system to form a bicycle, i.e. one or two of the heterocyclic ring carbons is common to an additional ring system. In instances where the heterocylcyl is a bicyclic ring, the second ring can be aromatic, e.g. a fused phenyl, pyridyl, pyrazolyl, or the like. The heterocyclyl may be linked through carbon or a heteroatom to the remainder of the molecule and in instances where the heterocylyl is a bicyclic ring, the link may be via the heteroatom containing ring or the fused ring. The heterocyclyl of ring A is a 5 to 11 membered monocyclic or bicyclic ring. When ring A is bicyclic, the second ring (i.e. the portion that does not include NH—C(O)—) can be aromatic, e.g. a fused phenyl or pyridinyl. When ring A is bicyclic, generally any further substituents will be on the second ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl and tetrahydroisoquinolinyl. Examples of heterocyclyl ring A include from piperidin-2-one, indoline-2-one, piperazine-2-one, pyrrolidin-2-one, 3,4-dihydroquinolin-2(1H)-one, 1H-pyrido[2,3-b][1,4]oxazin-2(3H)-one, 3,4-dihydropyrido[2,3-b]pyrazine-2(1H)-one, 1,5-diydrobenzo[e][1,4]oxazepin-2(3H)-one, 3,4-dihydro-1,5-naphthyridin-2 (1H)-one, 3,4-dihydro-1,6-naphthyridin-2(1H)-one, 3,4-dihydro-1,7-naphthyridin-2 (1H)-one, 3,4-dihydro-1,8-naphthyridin-2 (1H)-one and 3,4-dihydropyrazino[2,3-b]pyrazine-2 (1H)-one and 1,2,3,5-tetrahydro-4H-pyrido[2,3-b][1,4]diazepin-4-one. Unless specified otherwise, heterocyclyl within the definitions of $R^2$ and $R^8$, may be unsubstituted or substituted with one or more of the substituents defined herein. Examples of substituted heterocyclyl rings include 4,5-dihydro-1H-maleimido, tetramethylenesulfoxide and hydantoinyl. The monocyclic or bicyclic heterocycle ring A may be optionally further substituted as described herein.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl) within the definitions of $R^{1a}$, $R^{1b}$, $R^{1c}$, $R^{1d}$, $R^{1e}$, $R^{1f}$, $R^3$, $R^4$, $R^{4a}$, $R^6$, $R^7$, $R^{7a}$, $Q^1$, and within the definition of substituents for $R^2$, and $C_1$-$C_6$ alkylene (including $C_1$-$C_3$ alkylene) and $C_2$-$C_6$ alkenylene within the definitions of $R^5$, Q, $Q^{2a}$, $Q^{2b}$ and $Q^{2c}$, include halogen, hydroxyl, thiol, cyano, amino, nitro and $SF_5$ (a known mimetic of nitro), in particular, halogen (preferably fluorine or chlorine), hydroxyl and cyano. Other suitable substituents include amido, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl wherein any hydrocarbyl moiety may itself be substituted by halogen, e.g. fluorine, hydroxyl, cyano, amino, nitro or $SF_5$ (a known mimetic of nitro).

Examples of suitable substituents for "substituted" and "optionally substituted" rings, i.e. cycloalkyl, heterocyclyl, aryl and heteroaryl rings, within the definitions of $R^{1a}$, $R^{1b}$, $R^{1c}$, $R^{1d}$, $R^{1e}$, $R^{1f}$, $R^2$, $R^8$, ring A, include halogen, cyano, oxo, nitro, amino, hydroxy, —$C_1$-$C_6$ alkyl or $C_1$-$C_3$ alkyl, —$C_1$-$C_6$ alkoxy or $C_1$-$C_3$ alkoxy, aryl, heteroaryl, heterocyclyl, $C_3$-$C_6$ cycloalkyl, amino, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, nitro or $SF_5$.

Examples of suitable substituents for "substituted" and "optionally substituted" rings include in particular, fluorine, chlorine, oxo, cyano, $C_1$-$C_3$ alkyl, $C_1$-$C_3$ alkoxy, amino, amido, heterocyclyl, cycloalkyl, heteroary or aryl, wherein the alkyl or alkoxy is optionally substituted with one or more (e.g. one, two or three) substituents selected from halogen, hydroxyl, thiol, cyano, amino, nitro and $SF_5$.

Substituted groups thus include for example Br, Cl, F, CN, Me, Et, Pr, t-Bu, OMe, OEt, OPr, $C(CH_3)_3$, $CH(CH_3)_2$, $CF_3$, $OCF_3$, $C(O)NHCH_3$, cyclopropyl, phenyl, etc. In the case of aryl groups, the substitutions may be in the form of rings from adjacent carbon atoms in the aryl ring, for example cyclic acetals such as O—$CH_2$—O.

In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and $S(O)_2$-alkyl.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of the invention.

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Isotopes

The compounds described herein may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. Examples of isotopes include $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) may exist in crystalline or amorphous form and some of the crystalline forms may exist as polymorphs, which are included within the scope of the present invention.

Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

In accordance with a first aspect of the invention there is provided a compound of formula (I)

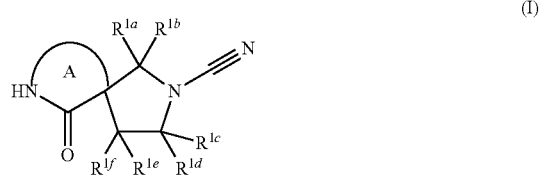

(I)

or a pharmaceutically acceptable salt thereof, wherein:
$R^{1a}$, $R^{1b}$, $R^{1c}$ and $R^{1d}$ each independently represent hydrogen or an optionally substituted $C_1$-$C_6$ alkyl, or $R^{1a}$ and $R^{1b}$ together form an optionally substituted cycloalkyl ring, $R^{1c}$ and $R^{1d}$ together form an optionally substituted cycloalkyl ring, or $R^{1d}$ together with $R^{1e}$ forms an optionally substituted cycloalkyl ring;

$R^{1e}$ and $R^{1f}$ each independently represent hydrogen, fluorine, cyano, hydroxyl, amino, optionally substituted $C_1$-$C_6$ alkyl, optionally substituted $C_1$-$C_6$ alkoxy or an optionally substituted 5 or 6 membered heteroaryl or aryl ring, or $R^{1e}$ forms an optionally substituted cycloalkyl ring with $R^{1f}$ or $R^{1d}$;

ring A is a 5 to 11 membered monocyclic or bicyclic heterocyclyl ring which may be optionally further substituted.

$R^{1a}$ may represent hydrogen. $R^{1a}$ may represent $C_1$-$C_6$ alkyl. $R^{1a}$ may represent hydrogen or $C_1$-$C_3$ alkyl, for example, methyl or ethyl. When $R^{1a}$ represents $C_1$-$C_6$ alkyl, $R^{1b}$, $R^{1c}$, $R^{1d}$, $R^{1e}$ and $R^{1f}$ may each represent hydrogen. The alkyl may be unsubstituted or substituted with one or more substituents selected from halogen, hydroxyl, thiol, cyano, amino, nitro and $SF_5$, in particular fluorine.

$R^{1b}$ may represent hydrogen. $R^{1b}$ may represent $C_1$-$C_6$ alkyl. $R^{1b}$ may represent hydrogen or $C_1$-$C_3$ alkyl, for example, methyl or ethyl. When $R^{1b}$ represents $C_1$-$C_6$ alkyl, $R^{1a}$, $R^{1c}$, $R^{1d}$, $R^{1e}$ and $R^{1f}$ may each represent hydrogen. The alkyl may be unsubstituted or substituted with one or more substituents selected from halogen, hydroxyl, thiol, cyano, amino, nitro and $SF_5$, in particular fluorine.

$R^{1c}$ may represent hydrogen. $R^{1c}$ may represent $C_1$-$C_6$ alkyl. $R^{1c}$ may represent hydrogen or $C_1$-$C_3$ alkyl, for example, methyl or ethyl. When $R^{1c}$ represents $C_1$-$C_6$ alkyl, $R^{1a}$, $R^{1b}$, $R^{1d}$, $R^{1e}$ and $R^{1f}$ may each represent hydrogen. The alkyl may be unsubstituted or substituted with one or more substituents selected from halogen, hydroxyl, thiol, cyano, amino, nitro and $SF_5$, in particular fluorine.

$R^{1d}$ may represent hydrogen. $R^{1d}$ may represent $C_1$-$C_6$ alkyl. $R^{1d}$ may represent hydrogen or $C_1$-$C_3$ alkyl, for example, methyl or ethyl. When $R^{1d}$ represents $C_1$-$C_6$ alkyl, $R^{1a}$, $R^{1b}$, $R^{1c}$, $R^{1e}$ and $R^{1f}$ may each represent hydrogen. The alkyl may be unsubstituted or substituted with one or more substituents selected from halogen, hydroxyl, thiol, cyano, amino, nitro and $SF_5$, in particular fluorine.

Alternatively, $R^{1a}$ and $R^b$ may together form a cycloalkyl ring. In addition or alternatively, but preferably alternatively, $R^{1c}$ and $R^{1d}$ may together form a cycloalkyl ring. The cycloalkyl ring can contain 3, 4, 5 or 6 atoms, in particular 3 or 4 atoms. When $R^{1a}$ and $R^b$ together form a $C_3$-$C_6$ cycloalkyl ring, $R^{1c}$, $R^{1d}$, $R^{1e}$ and $R^{1f}$ may be hydrogen. When $R^{1c}$ and $R^{1d}$ together form a cycloalkyl ring, $R^{1a}$, $R^{1b}$, $R^{1e}$ and $R^{1f}$ may each be hydrogen.

$R^{1e}$ may represent hydrogen, fluorine, cyano, hydroxyl, amino, optionally substituted $C_1$-$C_6$ alkyl, optionally substituted $C_1$-$C_6$ alkoxy, or an optionally substituted 5 or 6 membered heteroaryl or aryl ring. The alkyl and alkoxy may be substituted with one or more substituents selected from halogen, hydroxyl, thiol, cyano, amino, nitro and $SF_5$. The heteroaryl or aryl ring may be unsubstituted or substituted with halogen, cyano, nitro, amino, hydroxy, —$C_1$-$C_6$ alkyl or $C_1$-$C_3$ alkyl, —$C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, nitro or $SF_5$. In particular, the heteroaryl or aryl ring may be substituted with halogen, cyano, amino, $C_1$-$C_3$ alkoxy, —$C_1$-$C_6$ alkyl. $R^{1e}$ can represent hydrogen, fluorine, unsubstituted or substituted $C_1$-$C_3$ alkyl or unsubstituted or substituted $C_1$-$C_3$ alkoxy. $R^{1e}$ can represent hydrogen or methyl. $R^{1e}$ can represent hydrogen. $R^{1e}$ can represent fluorine. $R^{1e}$ can represent methyl. $R^{1e}$ can represent methoxy. $R^{1e}$ can represent $CF_3$. $R^{1e}$ can represent $OCF_3$. When $R^{1e}$ represents fluorine, cyano, hydroxyl, amino, optionally substituted $C_1$-$C_6$ alkyl or optionally substituted $C_1$-$C_6$ alkoxy or an optionally substituted 5 or 6 membered heteroaryl or aryl ring, $R^{1a}$, $R^{1b}$, $R^{1c}$, $R^{1d}$ and $R^{1f}$ may each represent hydrogen.

$R^{1f}$ may represent hydrogen, fluorine, cyano, hydroxyl, amino, optionally substituted $C_1$-$C_6$ alkyl, optionally substituted $C_1$-$C_6$ alkoxy, or an optionally substituted 5 or 6 membered heteroaryl or aryl ring. The alkyl and alkoxy may be substituted with one or more substituents selected from halogen, hydroxyl, thiol, cyano, amino, nitro and $SF_5$. The heteroaryl or aryl ring may be unsubstituted or substituted with halogen, cyano, oxo, nitro, amino, hydroxy, —$C_1$-$C_6$ alkyl or $C_1$-$C_3$ alkyl, —$C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, hydroxyl, cyano, amino, nitro or $SF_5$. In particular, the heteroaryl or aryl ring may be substituted with halogen, cyano, amino, $C_1$-$C_3$ alkoxy, —$C_1$-$C_6$ alkyl. $R^{1f}$ can represent hydrogen, fluorine, unsubstituted or substituted $C_1$-$C_3$ alkyl or unsubstituted or substituted $C_1$-$C_3$ alkoxy. $R^{1f}$ can represent hydrogen or methyl. $R^{1f}$ can represent hydrogen. $R^{1f}$ can represent fluorine. $R^{1f}$ can represent methyl. $R^{1f}$ can represent methoxy. $R^{1f}$ can represent $CF_3$. $R^{1f}$ can represent $OCF_3$. When $R^{1f}$ represents fluorine, cyano, hydroxyl, amino, optionally substituted $C_1$-$C_6$ alkyl or optionally substituted $C_1$-$C_6$ alkoxy or an optionally substituted 5 or 6 membered heteroaryl or aryl ring, $R^{1a}$, $R^{1b}$, $R^{1c}$, $R^{1d}$ and $R^{1e}$ may each represent hydrogen.

When $R^{1e}$ is hydrogen, $R^{1f}$ may represent hydrogen, fluorine, cyano, hydroxyl, amino, optionally substituted $C_1$-$C_6$ alkyl, optionally substituted $C_1$-$C_6$ alkoxy, or an optionally substituted 5 or 6 membered heteroaryl or aryl ring.

Alternatively, $R^{1e}$ and $R^{1f}$ may together form a cycloalkyl ring. Alternatively, $R^{1e}$ and $R^{1d}$ may together form a cycloalkyl ring. The cycloalkyl ring can contain 3, 4, 5 or 6 atoms, in particular 3 or 4 atoms. When $R^{1e}$ and $R^{1f}$ together form a $C_3$-$C_6$ cycloalkyl ring, $R^{1a}$, $R^{1b}$, $R^{1c}$ and $R^{1d}$ may be hydrogen. When $R^{1e}$ and $R^{1d}$ together form a $C_3$-$C_6$ cycloalkyl ring, $R^{1a}$, $R^{1b}$, $R^{1c}$ and $R^{1f}$ may each be hydrogen.

The cycloalkyl rings within the definitions of $R^{1a}$, $R^{1b}$, $R^{1c}$, $R^{1d}$, $R^{1e}$ and $R^{1f}$ may be unsubstituted or substituted with one or more substituents selected from halogen, cyano, oxo, nitro, amino, hydroxy, $C_1$-$C_3$ alkyl, $C_1$-$C_3$ alkoxy, $C_{1-3}$ alkylamino, $C_{2-6}$ alkenylamino, $C_1$-$C_3$ acylamino, carboxy, $C_1$-$C_3$ alkoxycarbonyl, carboxamidyl, carbamoyl, mono-$C_{1-3}$ carbamoyl and di-$C_{1-3}$ carbamoyl wherein any hydrocarbyl moiety may itself be substituted by one or more halogen, hydroxyl, cyano, amino, nitro or $SF_5$, in particular fluorine. In particular, the cycloalkyl ring may be unsubstituted or substituted with one or two substituents selected from halogen, cyano, oxo, nitro, amino, hydroxy, $C_1$-$C_3$ alkyl and $C_1$-$C_3$ alkoxy, wherein the alkyl and alkoxy may be substituted with one or more halogen, in particular fluorine.

The compounds may be in the form where $R^{1a}$, $R^{1b}$, $R^{1c}$, $R^{1d}$, $R^{1e}$ and $R^{1f}$ each represent hydrogen. In such cases the compounds may be of formula:

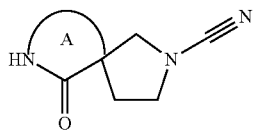

(IA)

or a pharmaceutically acceptable salt thereof, wherein ring A is a 5 to 11 membered monocyclic or bicyclic heterocyclyl ring which may be optionally further substituted.

Ring A may be monocyclic or bicyclic. Where the ring is bicyclic, the second ring (i.e. the ring not directly attached to the pyrrolidine ring) may be aromatic, saturated or may be partly saturated.

Preferably, the second ring is aromatic.

Ring A represents a 5 to 11 membered (e.g. 5, 6, 7, 8, 9, 10 or 11 membered) heterocyclyl ring which may be optionally further substituted with one or more (e.g. one, two, three or four) of $-Q^1-(R^2)_n$.

Ring A may represent a 5 or 6 membered heterocyclyl ring which may be optionally further substituted with one or more (e.g. one, two, three or four) of $-Q^1-(R^2)_n$.

Alternatively, ring A may represent a 9, 10 or 11 membered fused bicyclic heterocyclic ring which may be optionally further substituted with one or more (e.g. one, two, three or four) of $-Q^1-(R^2)_n$.

Ring A may comprise one or more (e.g. 1, 2 or 3) heteroatoms in addition to the amide nitrogen, wherein the additional heteroatom(s) are independently selected from nitrogen, oxygen and sulphur.

In particular, ring A may further comprise one or more additional heteroatoms selected from nitrogen and oxygen. When ring A is a bicyclic ring, the additional heteroatoms may be in first ring (i.e. the ring containing —NH—C(O)—) and/or the second ring (i.e. the fused ring portion not containing —NH—C(O)—).

Ring A may be selected from piperidin-2-one, indoline-2-one, piperazine-2-one, pyrrolidin-2-one, 3,4-dihydroquinolin-2(1H)-one, 1H-pyrido[2,3-b][1,4]oxazin-2(3H)-one, 3,4-dihydropyrido[2,3-b]pyrazine-2(1H)-one, 1,5-diydrobenzo[e][1,4]oxazepin-2(3H)-one, 3,4-dihydro-1,5-naphthyridin-2(1H)-one, 3,4-dihydro-1,6-naphthyridin-2(1H)-one, 3,4-dihydro-1,7-naphthyridin-2(1H)-one, 3,4-dihydro-1,8-naphthyridin-2(1H)-one and 3,4-dihydropyrazino[2,3-b]pyrazine-2(1H)-one and 1,2,3,5-tetrahydro-4H-pyrido[2,3-b][1,4]diazepin-4-one.

More particularly, ring A is selected from pyrrolidin-2-one, piperazine2-one, 3,4-dihydroquinolin-2(1H)-one, 1H-pyrido[2,3-b][1,4]oxazin-2(3H)-one, 3,4-dihydropyrido[2,3-b]pyrazine-2(1H)-one, 1,5-dihydrobenzo[e][1,4]oxazepin-2(3H)-one and 1,2,3,5-tetrahydro-4H-pyrido[2,3-b][1,4]diazepin-4-one.

In all case described herein, ring A may be further substituted with one or more $-Q^1-(R^2)_n$ wherein each occurrence of $-Q^1-(R^2)_n$ is the same or different, and wherein: n is 0 or 1;

$Q^1$ represents halogen, cyano, oxo, nitro, hydroxyl, —SR³, —NR³R⁴, —CONR³R⁴, —NR³COR⁴, —NR³CONR⁴R⁴ᵃ, —COR³, —C(O)OR³, —SO₂R³, —SO₂NR³R⁴, —NR³SO₂R⁴, NR³SO₂NR⁴R⁴ᵃ, —NR³C(O)OR⁴, optionally substituted —C₁-C₆ alkyl, optionally substituted —C₁-C₆ alkoxy, optionally substituted —C₂-C₆ alkenyl, optionally substituted —C₂-C₆ alkynyl, a covalent bond, an oxygen atom, a sulphur atom, —OR⁵—, —SO—, —SO₂—, —CO—, —C(O)O—, —C(O)O—, —C₀-C₃ alkylene-CONR³—C₀-C₃ alkylene, —C₀-C₃ alkylene-NR³—C₀-C₃ alkylene, —C₀-C₃ alkylene-NR³CO—C₀-C₃ alkylene, —C₀-C₃ alkylene-NR³CONR⁴—C₀-C₃ alkylene, —SO₂NR³—, —NR³SO₂—, —NR³SO₂NR⁴—, —NR³C(O)O—, —NR³C(O)OR⁵—, optionally substituted C₁-C₆ alkylene or optionally substituted —C₂-C₆ alkenylene;

R³, R⁴ and R⁴ᵃ each independently represent hydrogen or optionally substituted C₁-C₆ alkyl; and R⁵ represents optionally substituted C₁-C₆ alkylene.

When n is 1, R² represents an optionally substituted 3 to 10 membered heterocyclyl, cycloalkyl, heteroaryl or aryl ring (when n is 0, Q¹ is present and R² is absent).

Ring A may be further substituted with one, two, three or four of $-Q^1-(R^2)_n$. Substitution is in addition to the oxo substitution which forms part of the amide.

In particular, ring A may not be further substituted or may be further substituted with one, two or three of $-Q^1-(R^2)_n$. Ring A may be further substituted with one or two of $-Q^1-(R^2)_n$. Each occurrence of $-Q^1-(R^2)_n$ may be the same or different. Alternatively, ring A may be further substituted with one of $-Q^1-(R^2)_n$. Q¹, R² and n are as defined herein. In certain instances, ring A may not be further substituted.

In certain embodiments, ring A is substituted with a further optionally substituted ring, i.e. ring A is substituted with one or more $-Q^1-(R^2)_n$ moieties where n is 1 for at least one of the moieties. Generally, ring A will only be substituted with one $-Q^1-(R^2)_n$ moiety where n is 1, i.e. ring A will only be substituted with one ring, which may be in addition to other non-ring substituents.

In all cases described herein, Q¹ may be selected from halogen (e.g. fluorine, chlorine or bromine), cyano, oxo, nitro, hydroxyl, —SR³ (e.g. thiol), —NR³R⁴ (e.g. amino or N,N-dimethylamino), —CONR³R⁴ (e.g. amido), —NR³COR⁴ (N-acetyl), —NR³CONR⁴R⁴ᵃ, —COR³ (e.g. acetyl), —C(O)OR³ (e.g. methoxycarbonyl or ethoxycarbonyl), —SO₂R³ (e.g. methyl sulphonyl), —SO₂NR³R⁴ (e.g. dimethylaminosulphonyl), —NR³SO₂R⁴, NR³SO₂NR⁴R⁴ᵃ, —NR³C(O)OR⁴, optionally substituted —C₁-C₄ alkyl (e.g. propyl, isobutyl or tert butyl), optionally substituted C₁-C₂ alkyl (e.g. methyl or eithyl), optionally substituted —C₁-C₆ alkoxy, optionally substituted —C₂-C₆ alkenyl, optionally substituted —C₂-C₆ alkynyl, a covalent bond, an oxygen atom, a sulphur atom, —OR⁵—, —SO—, —SO₂—, —CO—, —C(O)O—, —C₀-C₃ alkylene-CONR³—C₀-C₃ alkylene, —C₀-C₃ alkylene-NR³—C₀-C₃ alkylene (e.g. methylamino), —C₀-C₃ alkylene-NR³CO—C₀-C₃ alkylene, —NR³CONR⁴—, —SO₂NR³—, —NR³SO₂—, —NR³SO₂NR⁴—, —NR³C(O)O—, —NR³C(O)OR⁵—, optionally substituted C₁-C₄ alkylene (e.g. methylene or ethylene) or optionally substituted —C₂-C₄ alkenylene (e.g. vinyl), wherein R³, R⁴, R⁴ᵃ and R⁵ are as defined above.

In one embodiment, Q¹ is selected from halogen, cyano, oxo, nitro, hydroxyl, —SR³, —NR³R⁴, —CONR³R⁴, —NR³COR⁴, —NR³CONR⁴R⁴ᵃ, —COR³, —C(O)OR³, —SO₂R³, —SO₂NR³R⁴, —NR³SO₂R⁴, NR³SO₂NR⁴R⁴ᵃ, —NR³C(O)OR⁴, optionally substituted —C₁-C₄ alkyl, optionally substituted C₁-C₂ alkyl, optionally substituted —C₁-C₆ alkoxy, optionally substituted —C₂-C₆ alkenyl, optionally substituted —C₂-C₆ alkynyl, a covalent bond, an oxygen atom, a sulphur atom, —OR⁵—, —SO—, —SO₂—, —CO—, —C(O)O—, —CONR³—, —NR³—, —NR³CO—, —NR³CONR⁴—, —SO₂NR³—, —NR³SO₂—, —NR³SO₂NR⁴—, —NR³C(O)O—, —NR³C(O)OR⁵—, optionally substituted C₁-C₄ alkylene or optionally substituted —C₂-C₄ alkenylene, wherein R³, R⁴, R⁴ᵃ and R⁵ are as defined above.

When n is 0, ring A may be further substituted with one or more (e.g. one, two, three or four) $Q^1$ substituents independently selected from halogen (e.g. fluorine, chlorine or bromine), cyano, oxo, nitro, hydroxyl, —$SR^3$, —$NR^3R^4$, —$CONR^3R^4$, —$NR^3C(O)R^4$, —$NR^3C(O)NR^4R^{4a}$, —$C(O)R^3$, —$C(O)OR^3$, —$SO_2R^3$, —$SO_2NR^3R^4$, —$NR^3SO_2R^4$, $NR^3SO_2NR^4R^{4a}$, —$NR^3C(O)OR^4$, —$C_1$-$C_6$ alkyl, —$C_1$-$C_6$ alkoxy, —$C_2$-$C_6$ alkenyl, or —$C_2$-$C_6$ alkynyl, wherein alkyl, alkoxy, alkenyl or alkynyl, may be unsubstituted or substituted with one or more substituents selected from halogen, hydroxyl, thiol, cyano, amino, nitro and $SF_5$, and wherein $R^3$, $R^4$, $R^{4a}$ and $R^5$ are as defined above.

In particular, when n is 0, $Q^1$ may represent oxo, methyl, ethyl, $CF_3$, methoxy, halogen (e.g. fluorine or chlorine), —$C(O)NR^3R^4$, wherein $R^3$ and $R^4$ are each independently represent hydrogen or methyl.

In particular examples, n is 0 and ring A represents a 5 or 6 membered heterocyclyl ring which is optionally substituted with one or more (e.g. one, two, three or four) $Q^1$ substituents independently selected from halogen (e.g. fluorine or chlorine), oxo, —$C_1$-$C_6$ alkyl or $C_1$-$C_3$ alkyl optionally substituted with one or more fluorine, e.g. $CF_3$.

Alternatively, n is 0 and ring A represents a 9 or 10 membered heterocyclyl ring which is optionally substituted with one or more (e.g. one, two, three or four) $Q^1$ substituents independently selected from halogen (e.g. fluorine or chlorine), —$C_1$-$C_6$ alkyl or $C_1$-$C_3$ alkyl or $C_1$-$C_6$ alkoxy or $C_1$-$C_3$ alkoxy, wherein the alkyl or alkoxy is optionally substituted with one or more fluorine, e.g. $CF_3$, or $C(O)NR^3R^4$ wherein $R^3$ and $R^4$ are each independently represent hydrogen and methyl.

When n is 1, $Q^1$ is a covalent bond or a linker selected from an oxygen atom, a sulphur atom, —$OR^5$—, —SO—, —$SO_2$—, —CO—, —C(O)O—, —$C_0$-$C_3$ alkylene-$CONR^3$—$C_0$-$C_3$ alkylene, —$C_0$-$C_3$ alkylene-$NR^3$—$C_0$-$C_3$ alkylene, —$C_0$-$C_3$ alkylene-$NR^3CO$—$C_0$-$C_3$ alkylene, —$NR^3CONR^4$—, —$SO_2NR^3$—, —$NR^3SO_2$—, —$NR^3SO_2NR^4$—, —$NR^3C(O)O$—, —$NR^3C(O)OR^5$—, —$C_1$-$C_6$ alkylene or —$C_2$-$C_6$ alkenylene, wherein the alkylene or alkenylene is optionally substituted with one or more substituents selected from halogen, hydroxyl, thiol, cyano, amino, nitro and $SF_5$, and wherein $R^3$, $R^4$ and $R^5$ are as defined above.

In particular, when n is 1, $Q^1$ may be selected from a covalent bond or a linker selected from covalent bond, an oxygen atom, a sulphur atom, —$OR^5$—, —SO—, —$SO_2$—, —CO—, —C(O)O—, —$CONR^3$—, —$NR^3$—, —$NR^3CO$—, —$NR^3CONR^4$—, —$SO_2NR^3$—, —$NR^3SO_2$—, —$NR^3SO_2NR^4$—, —$NR^3C(O)O$—, —$NR^3C(O)OR^5$—, —$C_1$-$C_6$ alkylene or —$C_2$-$C_6$ alkenylene, wherein the alkylene or alkenylene is optionally substituted with one or more substituents selected from halogen, hydroxyl, thiol, cyano, amino, nitro and $SF_5$, and wherein $R^3$, $R^4$ and $R^5$ are as defined above.

In particular, when n is 1, $Q^1$ is a covalent bond or $C_1$-$C_6$ alkylene, e.g. $C_1$-$C_3$ alkylene, wherein the alkylene is optionally substituted with one or more substituents selected from halogen, hydroxyl, thiol, cyano, amino, nitro and $SF_5$.

It is preferred that ring A is substituted with a further ring either directly or via a linker, i.e. ring A is substituted with at least one -$Q^1$-($R^2$)$_n$ wherein n is 1.

In all cases described herein, $R^2$ represents a 3 to 10 membered heterocyclyl, cycloalkyl, heteroaryl or aryl ring. $R^2$ may be selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl and tetrahydroisoquinolinyl.

$R^2$ may represent an optionally substituted 5 or 6 membered monocyclic heterocyclyl, cycloalkyl, heteroaryl or aryl ring.

Alternatively, $R^2$ may represent an optionally substituted 9 or 10 membered bicyclic heterocyclyl, cycloalkyl, heteroaryl or aryl ring.

In particular, $R^2$ is selected from phenyl, pyrazolyl, indazolyl, pyridinyl, benzothiazolyl and pyrimidinyl. More particularly, $R^2$ is phenyl.

In all cases described herein, $R^2$ may be optionally substituted with one or more substituents selected from halogen, cyano, oxo, nitro, hydroxyl —$SR^6$, —$NR^6R^7$, —$CONR^6R^7$, —$NR^6COR^7$, —$NR^6CONR^7R^{7a}$, —$COR^6$, —$C(O)OR^6$, —$SO_2R^6$, —$SO_2NR^6R^7$, —$NR^6SO_2R^7$, $NR^6SO_2NR^7R^{7a}$, —$NR^6C(O)OR^7$, —$C_1$-$C_6$ alkyl, —$C_1$-$C_6$ alkoxy, —$C_2$-$C_6$ alkenyl, —$C_2$-$C_6$, -$Q^{2a}$-$R^8$, -$Q^{2b}$-$NR^6CONR^7R^{7a}$, -$Q^{2b}$-$NR^6CONR^7$-$Q^{2c}$-$R^8$, -$Q^{2b}$-$NR^6R^7$, -$Q^{2b}$-$NR^6$-$Q^2$-$R^8$, -$Q^{2b}$-$COR^6$, -$Q^{2b}$-$CO$-$Q^{2c}$-$R^8$, -$Q^{2b}NR^6COR^7$, -$Q^{2b}NR^6CO$-$Q^2$-$R^8$, -$Q^{2b}$-$NR^6C(O)OR^7$, -$Q^{2b}$-$NR^6C(O)O$-$Q^2$-$R^8$, -$Q^{2b}$-$SO_2R^6$, -$Q^{2b}$-$SO_2$-$Q^{2c}$-$R^8$, -$Q^{2b}$-$CONR^6R^7$, -$Q^{2b}$-$CONR^6$-$Q^{2c}$-$R^8$, -$Q^{2b}$-$CO_2R^6$, -$Q^{2b}$-$CO_2$-$Q^{2c}$-$R^8$, -$Q^{2b}$-$SO_2NR^6R^7$, -$Q^{2b}$-$SO_2NR^6$-$Q^2$-$R^8$, -$Q^2$-$NR^6SO_2R^7$, -$Q^2$-$NR^6SO_2$-$Q^2$-$R^8$, -$Q^{2b}$-$NR^6SO_2NR^7R^{7a}$ and -$Q^{2b}$-$NR^6SO_2NR^7$-$Q^{2c}$-$R^8$ wherein the alkyl, alkoxy, alkenyl or alkynyl are optionally substituted with one or more substituents selected from halogen, hydroxyl, thiol, cyano, amino, nitro and $SF_5$, wherein $Q^{2a}$ represents a covalent bond, an oxygen atom, a sulphur atom, —SO—, —$SO_2$—, —CO—, optionally substituted $C_1$-$C_6$ alkylene or optionally substituted $C_2$-$C_6$ alkenylene;

$Q^{2b}$ and $Q^2C$ each independently represent a covalent bond, optionally substituted $C_1$-$C_6$ alkylene or optionally substituted $C_2$-$C_6$ alkylenylene;

$R^6$, R and $R^{7a}$ each independently represent hydrogen or optionally substituted $C_1$-$C_6$ alkyl; and $R^8$ represents optionally substituted heterocyclyl, optionally substituted heteroaryl, optionally substituted aryl, or an optionally substituted cycloalkyl.

$R^2$ may be substituted with one or more (e.g. one, two, three or four), in particular one or two, substituents independently selected from halogen, cyano, oxo, nitro, hydroxyl, —$SR^6$, —$NR^6R^7$, —$CONR^6R^7$, —$NR^6COR^7$, —$NR^6CONR^7R^{7a}$, —$COR^6$, —$C(O)OR^6$, —$SO_2R^7$, —$SO_2NR^6R^7$, —$NR^6SO_2R^7$, $NR^6SO_2NR^7R^{7a}$, —$NR^6C(O)OR^7$, —$C_1$-$C_6$ alkyl, —$C_1$-$C_6$ alkoxy, —$C_2$-$C_6$ alkenyl, —$C_2$-$C_6$ alkynyl, -$Q^{2b}$-$NR^6CONR^7R^{7a}$, -$Q^{2b}NR^6R^7$, -$Q^{2b}$-$C(O)R^6$, -$Q^{2b}NR^6C(O)R^7$, -$Q^{2b}NR^6C(O)OR^7$, -$Q^{2b}$-$SO_2R^6$, -$Q^{2b}$-$C(O)NR^6R^7$, -$Q^{2b}$-$CO_2R^6$, -$Q^{2b}$-$SO_2NR^6R^7$, -$Q^{2b}$-

$NR^6SO_2R^7$ and $-Q^{2b}-NR^6SO_2NR^7R^{7a}$, wherein $Q^{2b}$ represents a covalent bond, optionally substituted $C_1$-$C_6$ alkylene or optionally substituted $C_2$-$C_6$ alkenylene, and wherein $R^6$, $R^7$ and $R^{7a}$ each independently represent hydrogen or optionally substituted $C_1$-$C_6$ alkyl, wherein any alkyl, alkoxy, alkenyl, alkynyl, alkylene or alkenylene is optionally substituted with one or more (e.g. one, two, three or four) substituents selected from halogen, hydroxyl, thiol, cyano, amino, nitro and $SF_5$.

In particular, $R^2$ may be substituted with one or more substituents selected from halogen (e.g. fluorine), cyano, oxo, $C_1$-$C_3$ alkyl or $C_1$-$C_3$ alkoxy wherein the alkyl or alkoxy is optionally substituted with fluorine, $-CONR^6R^7$, $-NR^6COR^7$, $-Q^{2a}$-$R^8$, $-Q^{2b}$-$NR^6SO_2$-$Q^{2c}$-$R^8$, wherein $Q^{2a}$ is a covalent bond, an oxygen atom, $-CO-$, $-SO_2-$ or $-C_1$-$C_3$ alkylene, $Q^{2b}$ is a covalent bond or $C_1$-$C_3$ alkylene and $Q^{2c}$ is a covalent bond, and wherein $R^6$ and $R^7$ are each independently selected from hydrogen or $C_1$-$C_3$ alkyl, and $R^8$ is a 3 to 10 membered optionally substituted cycloalkyl, heterocyclcyl, aryl or heteroaryl ring, in particular a 3 to 6 membered monocyclic cycloalkyl, heterocyclyl, heteroaryl or aryl ring. More particularly, $R^8$ is selected from phenyl, piperazinyl, cyclopropyl, morpholinyl and piperidinyl.

More particularly, $R^2$ may be substituted with one or more substituents selected from halogen (e.g. chlorine or fluorine), cyano, oxo, methyl, i-propyl, OMe, $OCF_3$, O-i-propyl, $-C(O)NHMe$, $-C(O)N(CH_3)_2$, $-NHC(O)Me$, piperidinyl, $-NHSO_2$-cyclopropyl, $Q^{2a}$-phenyl wherein $Q^{2a}$ is a covalent bond, an oxygen atom or methyleneoxy, $Q^{2a}$-piperazinyl wherein $Q^{2a}$ is a covalent bond or $-CO-$ and $Q^{2a}$-morpholinyl wherein $Q^{2a}$ is $-CO-$ or $-SO_2-$.

In particular, $R^2$ is unsubstituted, mono-substituted or disubstituted.

In certain instances, $R^2$ is optionally substituted with a 3 to 10 membered heterocyclyl, cycloalkyl, heteroaryl or aryl ring, either directly attached or via a linking group. The linking group may be an oxygen atom, carbonyl, $-SO_2-$, $-NHSO_2-$, or an optionally substituted $C_1$-$C_3$ alkylene. The linking group may be oxygen, $-CO-$ or an alkylene chain, for example, methylene or methyleneoxy. For example, $R^2$ may be substituted with a 5 or 6 membered ring selected from phenyl, piperidinyl, piperazinyl and morpholinyl. $R^2$ may be further substituted, in addition to the ring substitution, with one or more non-ring substituents selected from halogen, cyano, oxo, $C_1$-$C_3$ alkyl, $C_1$-$C_3$ alkoxy wherein the alkyl or alkoxy may be optionally substituted with fluorine, $-C(O)NHMe$, $-C(O)N(CH_3)_2$ and $-NHC(O)Me$.

In certain instances, $R^2$ represents a 3 to 10 membered heterocyclyl, cycloalkyl, heteroaryl or aryl ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl and tetrahydroisoquinolinyl, which is either unsubstituted or substituted with one or more (e.g. one, two or three) substituents selected from halogen (e.g. fluorine or chlorine), cyano, oxo, nitro, hydroxyl, $-SR^6$, $-NR^6R^7$, $-CONR^6R^7$, $-NR^6COR^7$, $-NR^6CONR^7R^{7a}$, $-COR^6$, $-C(O)OR^6$, $-SO_2R^6$, $-SO_2NR^6R^7$, $-NR^6SO_2R^7$, $NR^6SO_2NR^7R^{7a}$, $-NR^6C(O)OR^7$, $-C_1$-$C_6$ alkyl, $-C_1$-$C_6$ alkoxy, $-C_2$-$C_6$ alkenyl, $-C_2$-$C_6$ alkynyl, $-Q^{2a}$-$R^8$, $-Q^{2b}$-$NR^6CONR^7R^{7a}$-$Q^{2b}$-$NR^6CONR^7$-$Q^{2c}$-$R^8$, $-Q^{2b}NR^6R^7$, $-Q^{2b}$-$NR^6$-$Q^2$-$R^8$, $-Q^{2b}$-$COR^6$, $-Q^{2b}$-$CO$-$Q^{2c}$-$R^8$, $-Q^{2b}NR^6COR^7$, $-Q^{2b}NR^6CO$-$Q^{2c}$-$R^8$, $-Q^{2b}$-$NR^6C(O)OR^7$, $-Q^{2b}$-$NR^6C(O)O$-$Q^{2c}$-$R^8$, $-Q^{2b}$-$SO_2R^6$, $-Q^{2b}$-$SO_2$-$Q^{2c}$-$R^8$, $-Q^{2b}$-$CONR^6R^7$, $-Q^{2b}$-$CONR^6$-$Q^{2c}$-$R^8$, $-Q^{2b}$-$CO_2R^6$, $-Q^{2b}$-$CO_2$-$Q^{2c}$-$R^8$, $-Q^{2b}SO_2NR^6R^7$, $-Q^{2b}$-$SO_2NR^6$-$Q^{2c}$-$R^8$, $-Q^{2b}NR^6SO_2R^7$, $-Q^{2b}$-$NR^6SO_2$-$Q^{2c}$-$R^8$, $-Q^2$-$NR^6SO_2NR^7R^8$ and $-Q^{2b}$-$NR^6SO_2NR^7$-$Q^{2c}$-$R^8$, wherein the alkyl, alkoxy, alkenyl or alkynyl are optionally substituted with one or more substituents selected from halogen, hydroxyl, thiol, cyano, amino, nitro and $SF_5$, wherein $Q^{2a}$ represents a covalent bond, an oxygen atom, a sulphur atom, $-SO-$, $-SO_2-$, $-CO-$, $-C_1$-$C_6$ alkylene or optionally substituted $C_2$-$C_6$ alkenylene, $Q^{2b}$ and $Q^{2C}$ each independently represent a covalent bond, optionally substituted $C_1$-$C_6$ alkylene or optionally substituted $C_2$-$C_6$ alkylenylene, $R^6$, $R^7$ and $R^{7a}$ each independently represent hydrogen or optionally substituted $C_1$-$C_6$ alkyl, and $R^8$ represents optionally substituted heterocyclyl, optionally substituted heteroaryl, optionally substituted aryl, or an optionally substituted cycloalkyl.

In particular, $R^2$ may be selected from phenyl, pyrazolyl, indazolyl, pyridinyl, benzothiazolyl and pyrimidinyl, wherein the ring is unsubstituted or substituted with one or more (e.g. one, two or three) substitutents selected from halogen, cyano, oxo, $C_1$-$C_3$ alkyl or $C_1$-$C_3$ alkoxy wherein the alkyl or alkoxy is optionally substituted with fluorine, $-CONR^6R^7$, $-NR^6COR^7$, $-Q^{2a}$-$R^8$, $-Q^{2b}$-$NR^6SO_2$-$Q^{2c}$-$R^8$, wherein $Q^{2a}$ is a covalent bond, an oxygen atom, $-CO-$, $-SO_2-$ or $-C_1$-$C_3$ alkylene, $Q^{2b}$ is a covalent bond or $C_1$-$C_3$ alkylene and $Q^2C$ is a covalent bond and wherein $R^6$ and $R^7$ are each independently selected from hydrogen or $C_1$-$C_3$ alkyl and $R^8$ is a 3 to 10 membered optionally substituted cycloalkyl, heterocyclcyl, aryl or heteroaryl ring.

The present invention further relates to compounds of formula (I), or a pharmaceutically acceptable salt thereof, wherein:

$R^{1a}$, $R^{1b}$, $R^{1c}$ and $R^{1d}$ are each independently selected from hydrogen and $C_1$-$C_3$ alkyl which may be optionally substituted with fluorine;

$R^{1e}$ and $R^{1f}$ are each independently selected from hydrogen, fluorine, $C_1$-$C_3$ alkyl or $C_1$-$C_3$ alkoxy wherein the alkyl or alkoxy is optionally substituted with fluorine;

Ring A is a monocyclic or bicyclic 5 to 10 membered heterocyclyl ring which is optionally further substituted with one, two, or three of $-Q^1$-$(R^2)_n$ wherein $Q^1$, $R^2$ and n are as defined herein.

The present invention further relates to compounds of formula (I), or a pharmaceutically acceptable salt thereof, wherein:

$R^{1a}$, $R^{1b}$, $R^{1c}$, $R^{1d}$, $R^{1e}$ and $R^{1f}$ each represent hydrogen;

Ring A is selected from pyrrolidin-2-one, piperazine2-one, 3,4-dihydroquinolin-2(1H)-one, 1H-pyrido[2,3-b][1,4]

oxazin-2(3H)-one, 3,4-dihydropyrido[2,3-b]pyrazine-2 (1H)-one, 1,5-dihydrobenzo[e][1,4]oxazepin-2(3H)-one and 1,2,3,5-tetrahydro-4H-pyrido[2,3-b][1,4]diazepin-4-one wherein the ring is optionally further substituted with one, two or three of -$Q^1$-$(R^2)_n$ wherein $Q^1$, $R^2$ and n are as defined herein.

The present invention further relates to compounds of formula (I), or a pharmaceutically acceptable salt thereof, wherein:

$R^{1a}$, $R^{1b}$, $R^{1c}$, $R^{1d}$, $R^{1e}$ and $R^{1f}$ each represent hydrogen;

Ring A represents a monocyclic or bicyclic 5 to 10 membered heterocyclyl ring which is optionally further substituted with one, two or three of -$Q^1$-$(R^2)_n$; wherein n is 0 or 1;

$R^2$ is selected from piperidiniyl, pyrrolyl, phenyl, pyrazolyl, isoxazolyl, indazolyl, pyridinyl, dihidropyridinyl, benzothiazolyl and pyrimidinyl;

$Q^1$ is as defined herein.

Examples of the monocyclic and bicyclic heterocyclyl ring represented by A include those shown below:

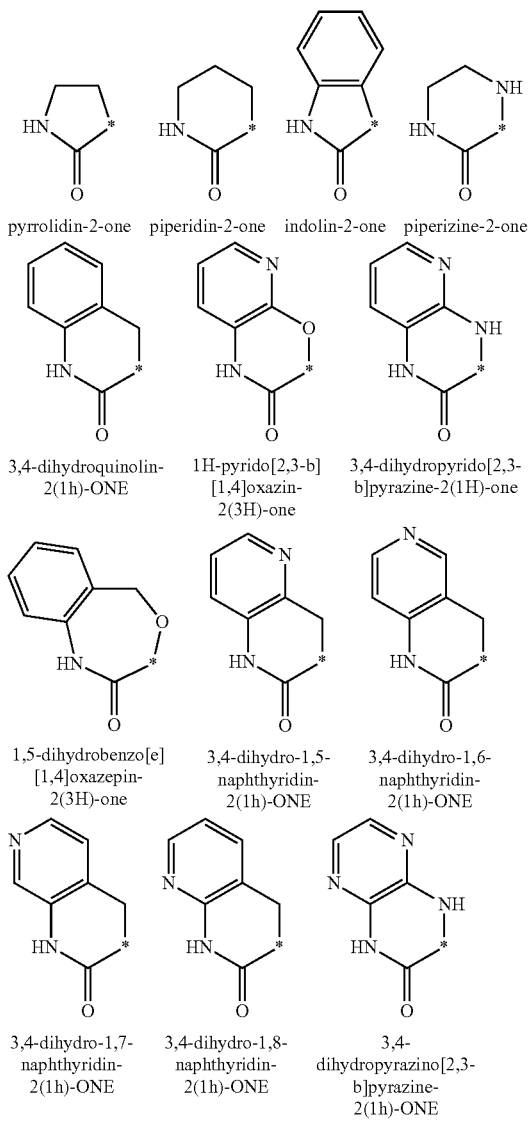

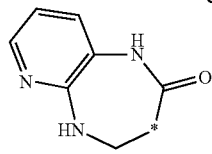

1,2,3,5-tetrahydro-
4H-pyrido[2,3-
b][1,4]diazepin-4-one wherein * represents the point of attachment to the remainder of the molecule, i.e. to the pyrrolidine cyanamide to form a spirocycle, and wherein the rings are optionally substituted with one or more of -$Q^1$-$(R^2)_n$.

Examples of novel compounds of formula I include:

2'-oxo-1',4'-dihydro-2'H-spiro[pyrrolidine-3,3'-quinoline]-1-carbonitrile

7'-chloro-2'-oxo-1',4'-dihydro-2'H-spiro[pyrrolidine-3,3'-quinoline]-1-carbonitrile 7'-methoxy-2'-oxo-1',4'-dihydro-2'H-spiro[pyrrolidine-3,3'-quinoline]-1-carbonitrile 7'-(5-isopropyl-2-methoxyphenyl)-2'-oxo-1',4'-dihydro-2'H-spiro[pyrrolidine-3,3'-quinoline]-1-carbonitrile 7'-([1,1'-biphenyl]-4-yl)-2'-oxo-1',4'-dihydro-2'H-spiro[pyrrolidine-3,3'-quinoline]-1-carbonitrile 7'-(4-(benzyloxy)phenyl)-2'-oxo-1',4'-dihydro-2'H-spiro[pyrrolidine-3,3'-quinoline]-1-carbonitrile 7'-(2-fluoro-5-methylphenyl)-2'-oxo-1',4'-dihydro-2'H-spiro[pyrrolidine-3,3'-quinoline]-1-carbonitrile 7'-(3-cyanophenyl)-2'-oxo-1',4'-dihydro-2'H-spiro[pyrrolidine-3,3'-quinoline]-1-carbonitrile 7'-(1-methyl-1H-pyrazol-5-yl)-2'-oxo-1',4'-dihydro-2'H-spiro[pyrrolidine-3,3'-quinoline]-1-carbonitrile 2'-oxo-7'-(4-phenoxyphenyl)-1',4'-dihydro-2'H-spiro[pyrrolidine-3,3'-quinoline]-1-carbonitrile 7'-(1-methyl-1H-pyrazol-4-yl)-2'-oxo-1',4'-dihydro-2'H-spiro[pyrrolidine-3,3'-quinoline]-1-carbonitrile 7'-(4-cyanophenyl)-2'-oxo-1',4'-dihydro-2'H-spiro[pyrrolidine-3,3'-quinoline]-1-carbonitrile 7'-(2-chloro-5-(trifluoromethoxy)phenyl)-2'-oxo-1',4'-dihydro-2'H-spiro[pyrrolidine-3,3'-quinoline]-1-carbonitrile 5-(1-cyano-2'-oxo-1',4'-dihydro-2'H-spiro[pyrrolidine-3,3'-quinolin]-7'-yl)-N-methylpicolinamide 7'-(2-(benzyloxy)phenyl)-2'-oxo-1',4'-dihydro-2'H-spiro[pyrrolidine-3,3'-quinoline]-1-carbonitrile 4-(1-cyano-2'-oxo-1',4'-dihydro-2'H-spiro[pyrrolidine-3,3'-quinolin]-7'-yl)-N-methylbenzamide 7'-(3-((2-chlorobenzyl)oxy)phenyl)-2'-oxo-1',4'-dihydro-2'H-spiro[pyrrolidine-3,3'-quinoline]-1-carbonitrile 7'-(4-(4-methylpiperazin-1-yl)phenyl)-2'-oxo-1',4'-dihydro-2'H-spiro[pyrrolidine-3,3'-quinoline]-1-carbonitrile 7'-(6-methoxypyridin-3-yl)-2'-oxo-1',4'-dihydro-2'H-spiro[pyrrolidine-3,3'-quinoline]-1-carbonitrile 7'-(5-fluoro-2-isopropoxyphenyl)-2'-oxo-1',4'-dihydro-2'H-spiro[pyrrolidine-3,3'-quinoline]-1-carbonitrile 7'-(3-methyl-1H-indazol-6-yl)-2'-oxo-1',4'-dihydro-2'H-spiro[pyrrolidine-3,3'-quinoline]-1-carbonitrile 7'-(4-(4-methylpiperazine-1-carbonyl)phenyl)-2'-oxo-1',4'-dihydro-2'H-spiro[pyrrolidine-3,3'-quinoline]-1-carbonitrile 7'-(1-methyl-1H-indazol-5-yl)-2'-oxo-1',4'-dihydro-2'H-spiro[pyrrolidine-3,3'-quinoline]-1-carbonitrile 7'-(5-methyl-1H-indazol-4-yl)-2'-oxo-1',4'-dihydro-2'H-spiro[pyrrolidine-3,3'-quinoline]-1-carbonitrile N-(3-(1-cyano-2'-oxo-1',4'-dihydro-2'H-spiro[pyrrolidine-3, 3'-quinolin]-7'-yl)phenyl)cyclopropanesulfonamide
7'-(3-methyl-1H-pyrazol-4-yl)-2'-oxo-1',4'-dihydro-2'H-spiro[pyrrolidine-3,3'-quinoline]-1-carbonitrile
2'-oxo-7'-(pyrimidin-5-yl)-1',4'-dihydro-2'H-spiro[pyrrolidine-3,3'-quinoline]-1-carbonitrile
N-(3-(1-cyano-2'-oxo-1',4'-dihydro-2'H-spiro[pyrrolidine-3, 3'-quinolin]-7'-yl)phenyl)acetamide
3-(1-cyano-2'-oxo-1',4'-dihydro-2'H-spiro[pyrrolidine-3,3'-quinolin]-7'-yl)-N,N-dimethylbenzamide
N-(4-(1-cyano-2'-oxo-1',4'-dihydro-2'H-spiro[pyrrolidine-3, 3'-quinolin]-7'-yl)phenyl)acetamide
7'-(4-(morpholinosulfonyl)phenyl)-2'-oxo-1',4'-dihydro-2'H-spiro[pyrrolidine-3,3'-quinoline]-1-carbonitrile
7'-(3,5-dimethyl-1H-pyrazol-4-yl)-2'-oxo-1',4'-dihydro-2'H-spiro[pyrrolidine-3,3'-quinoline]-1-carbonitrile
7'-(2-methylpyridin-4-yl)-2'-oxo-1',4'-dihydro-2'H-spiro[pyrrolidine-3,3'-quinoline]-1-carbonitrile
2'-oxo-7'-(3-(piperidin-1-yl)phenyl)-1',4'-dihydro-2'H-spiro[pyrrolidine-3,3'-quinoline]-1-carbonitrile
N-(2-(1-cyano-2'-oxo-1',4'-dihydro-2'H-spiro[pyrrolidine-3, 3'-quinolin]-7'-yl)phenyl)acetamide
7'-(4-(morpholine-4-carbonyl)phenyl)-2'-oxo-1',4'-dihydro-2'H-spiro[pyrrolidine-3,3'-quinoline]-1-carbonitrile
7'-(3-(morpholinosulfonyl)phenyl)-2'-oxo-1',4'-dihydro-2'H-spiro[pyrrolidine-3,3'-quinoline]-1-carbonitrile
7'-(1-methyl-6-oxo-1,6-dihydropyridin-3-yl)-2'-oxo-1',4'-dihydro-2'H-spiro[pyrrolidine-3,3'-quinoline]-1-carbonitrile
7'-(2-methylbenzo[d]thiazol-5-yl)-2'-oxo-1',4'-dihydro-2'H-spiro[pyrrolidine-3,3'-quinoline]-1-carbonitrile
2'-oxo-6'-phenyl-1',4'-dihydro-2'H-spiro[pyrrolidine-3,3'-quinoline]-1-carbonitrile
6'-(4-cyanophenyl)-2'-oxo-1',4'-dihydro-2'H-spiro[pyrrolidine-3,3'-quinoline]-1-carbonitrile
6'-(3-cyanophenyl)-2'-oxo-1',4'-dihydro-2'H-spiro[pyrrolidine-3,3'-quinoline]-1-carbonitrile
6'-(4-fluorophenyl)-2'-oxo-1',4'-dihydro-2'H-spiro[pyrrolidine-3,3'-quinoline]-1-carbonitrile
6'-(3-fluorophenyl)-2'-oxo-1',4'-dihydro-2'H-spiro[pyrrolidine-3,3'-quinoline]-1-carbonitrile
1-cyano-N,N-dimethyl-2'-oxo-1',4'-dihydro-2'H-spiro[pyrrolidine-3,3'-quinoline]-7'-carboxamide
1-cyano-N-methyl-2'-oxo-1',4'-dihydro-2'H-spiro[pyrrolidine-3,3'-quinoline]-7'-carboxamide
2-oxo-1,2-dihydrospiro[pyrido[2,3-b][1,4]oxazine-3,3'-pyrrolidine]-1'-carbonitrile
2-oxo-7-phenyl-1,2-dihydrospiro[pyrido[2,3-b][1,4]oxazine-3,3'-pyrrolidine]-1'-carbonitrile
7-(4-cyanophenyl)-2-oxo-1,2-dihydrospiro[pyrido[2,3-b][1,4]oxazine-3,3'-pyrrolidine]-1'-carbonitrile
7-(3-cyanophenyl)-2-oxo-1,2-dihydrospiro[pyrido[2,3-b][1,4]oxazine-3,3'-pyrrolidine]-1'-carbonitrile
7-(4-fluorophenyl)-2-oxo-1,2-dihydrospiro[pyrido[2,3-b][1,4]oxazine-3,3'-pyrrolidine]-1'-carbonitrile
7-(3-fluorophenyl)-2-oxo-1,2-dihydrospiro[pyrido[2,3-b][1,4]oxazine-3,3'-pyrrolidine]-1'-carbonitrile
2-oxo-6-phenyl-1,2-dihydrospiro[pyrido[2,3-b][1,4]oxazine-3,3'-pyrrolidine]-1'-carbonitrile
2-oxo-1,4-dihydro-2H-spiro[pyrido[2,3-b]pyrazine-3,3'-pyrrolidine]-1'-carbonitrile
2-oxo-6-(trifluoromethyl)-1,4-dihydro-2H-spiro[pyrido[2,3-b]pyrazine-3,3'-pyrrolidine]-1'-carbonitrile
2-oxo-7-phenyl-1,4-dihydro-2H-spiro[pyrido[2,3-b]pyrazine-3,3'-pyrrolidine]-1'-carbonitrile
7-(4-cyanophenyl)-2-oxo-1,4-dihydro-2H-spiro[pyrido[2,3-b]pyrazine-3,3'-pyrrolidine]-1'-carbonitrile
7-(4-fluorophenyl)-2-oxo-1,4-dihydro-2H-spiro[pyrido[2,3-b]pyrazine-3,3'-pyrrolidine]-1'-carbonitrile
7-(3-fluorophenyl)-2-oxo-1,4-dihydro-2H-spiro[pyrido[2,3-b]pyrazine-3,3'-pyrrolidine]-1'-carbonitrile
3-oxo-3,4-dihydro-1H-spiro[pyrido[2,3-b]pyrazine-2,3'-pyrrolidine]-1'-carbonitrile
6-oxo-2,7-diazaspiro[4.4]nonane-2-carbonitrile
(R)-6-oxo-2,7-diazaspiro[4.4]nonane-2-carbonitrile
(S)-2-oxo-7-phenyl-1,2-dihydrospiro[pyrido[2,3-b][1,4]oxazine-3,3'-pyrrolidine]-1'-carbonitrile
(S)-2-oxo-1,2-dihydrospiro[pyrido[2,3-b][1,4]oxazine-3,3'-pyrrolidine]-1'-carbonitrile
(S)-2-oxo-1,4-dihydro-2H-spiro[pyrido[2,3-b]pyrazine-3,3'-pyrrolidine]-1'-carbonitrile
(R)-2'-oxo-6'-phenyl-1',4'-dihydro-2'H-spiro[pyrrolidine-3,3'-quinoline]-1-carbonitrile
(S)-2-oxo-7-phenyl-1,4-dihydro-2H-spiro[pyrido[2,3-b]pyrazine-3,3'-pyrrolidine]-1'-carbonitrile
(S)-7-(3-fluorophenyl)-2-oxo-1,2-dihydrospiro[pyrido[2,3-b][1,4]oxazine-3,3'-pyrrolidine]-1'-carbonitrile
(S)-7-(4-cyanophenyl)-2-oxo-1,2-dihydrospiro[pyrido[2,3-b][1,4]oxazine-3,3'-pyrrolidine]-1'-carbonitrile
(S)-7-(3-cyanophenyl)-2-oxo-1,2-dihydrospiro[pyrido[2,3-b][1,4]oxazine-3,3'-pyrrolidine]-1'-carbonitrile
(S)-7-(4-fluorophenyl)-2-oxo-1,4-dihydro-2H-spiro[pyrido[2,3-b]pyrazine-3,3'-pyrrolidine]-1'-carbonitrile
(S)-7-(3-fluorophenyl)-2-oxo-1,4-dihydro-2H-spiro[pyrido[2,3-b]pyrazine-3,3'-pyrrolidine]-1'-carbonitrile
(S)-7-(4-fluorophenyl)-2-oxo-1,2-dihydrospiro[pyrido[2,3-b][1,4]oxazine-3,3'-pyrrolidine]-1'-carbonitrile
(S)-7-(3-cyanophenyl)-2-oxo-1,4-dihydro-2H-spiro[pyrido[2,3-b]pyrazine-3,3'-pyrrolidine]-1'-carbonitrile
(8R)-8-methyl-7,10-dioxo-2,6,9-triazaspiro[4.5]decane-2-carbonitrile
7,10-dioxo-2,6,9-triazaspiro[4.5]decane-2-carbonitrile
(8S)-8-methyl-7,10-dioxo-2,6,9-triazaspiro[4.5]decane-2-carbonitrile
7,10-dioxo-8-phenyl-2,6,9-triazaspiro[4.5]decane-2-carbonitrile
8-ethyl-6-oxo-2,7-diazaspiro[4.4]nonane-2-carbonitrile
8-benzyl-6-oxo-2,7-diazaspiro[4.4]nonane-2-carbonitrile
8-methyl-6-oxo-2,7-diazaspiro[4.4]nonane-2-carbonitrile
2-oxo-1,5-dihydro-2H-spiro[benzo[e][1,4]oxazepine-3,3'-pyrrolidine]-1'-carbonitrile
2-oxo-1,2,4,5-tetrahydrospiro[pyrido[2,3-b][1,4]diazepine-3,3'-pyrrolidine]-1'-carbonitrile
8-methyl-7,10-dioxo-8-phenyl-2,6,9-triazaspiro[4.5]decane-2-carbonitrile
2'-oxo-1',4'-dihydro-2'H-spiro[pyrrolidine-3,3'-quinoline]-1-carbonitrile
7'-chloro-2'-oxo-1',4'-dihydro-2'H-spiro[pyrrolidine-3,3'-quinoline]-1-carbonitrile
7'-methoxy-2'-oxo-1',4'-dihydro-2'H-spiro[pyrrolidine-3,3'-quinoline]-1-carbonitrile
7'-(5-isopropyl-2-methoxyphenyl)-2'-oxo-1',4'-dihydro-2'H-spiro[pyrrolidine-3,3'-quinoline]-1-carbonitrile
7'-([1,1'-biphenyl]-4-yl)-2'-oxo-1',4'-dihydro-2'H-spiro[pyrrolidine-3,3'-quinoline]-1-carbonitrile
7'-(4-(benzyloxy)phenyl)-2'-oxo-1',4'-dihydro-2'H-spiro[pyrrolidine-3,3'-quinoline]-1-carbonitrile
7'-(2-fluoro-5-methylphenyl)-2'-oxo-1',4'-dihydro-2'H-spiro[pyrrolidine-3,3'-quinoline]-1-carbonitrile
7'-(3-cyanophenyl)-2'-oxo-1',4'-dihydro-2'H-spiro[pyrrolidine-3,3'-quinoline]-1-carbonitrile
7'-(1-methyl-1H-pyrazol-5-yl)-2'-oxo-1',4'-dihydro-2'H-spiro[pyrrolidine-3,3'-quinoline]-1-carbonitrile 2'-oxo-7'-(4-phenoxyphenyl)-1',4'-dihydro-2'H-spiro[pyrrolidine-3,3'-quinoline]-1-carbonitrile
7'-(1-methyl-1H-pyrazol-4-yl)-2'-oxo-1',4'-dihydro-2'H-spiro[pyrrolidine-3,3'-quinoline]-1-carbonitrile
7'-(4-cyanophenyl)-2'-oxo-1',4'-dihydro-2'H-spiro[pyrrolidine-3,3'-quinoline]-1-carbonitrile
7'-(2-chloro-5-(trifluoromethoxy)phenyl)-2'-oxo-1',4'-dihydro-2'H-spiro[pyrrolidine-3,3'-quinoline]-1-carbonitrile
5-(1-cyano-2'-oxo-1',4'-dihydro-2'H-spiro[pyrrolidine-3,3'-quinolin]-7'-yl)-N-methylpicolinamide
7'-(2-(benzyloxy)phenyl)-2'-oxo-1',4'-dihydro-2'H-spiro[pyrrolidine-3,3'-quinoline]-1-carbonitrile
4-(1-cyano-2'-oxo-1',4'-dihydro-2'H-spiro[pyrrolidine-3,3'-quinolin]-7'-yl)-N-methylbenzamide
7'-(3-((2-chlorobenzyl)oxy)phenyl)-2'-oxo-1',4'-dihydro-2'H-spiro[pyrrolidine-3,3'-quinoline]-1-carbonitrile
7'-(4-(4-methylpiperazin-1-yl)phenyl)-2'-oxo-1',4'-dihydro-2'H-spiro[pyrrolidine-3,3'-quinoline]-1-carbonitrile
7'-(6-methoxypyridin-3-yl)-2'-oxo-1',4'-dihydro-2'H-spiro[pyrrolidine-3,3'-quinoline]-1-carbonitrile
7'-(5-fluoro-2-isopropoxyphenyl)-2'-oxo-1',4'-dihydro-2'H-spiro[pyrrolidine-3,3'-quinoline]-1-carbonitrile
7'-(3-methyl-1H-indazol-6-yl)-2'-oxo-1',4'-dihydro-2'H-spiro[pyrrolidine-3,3'-quinoline]-1-carbonitrile
7'-(4-(4-methylpiperazine-1-carbonyl)phenyl)-2'-oxo-1',4'-dihydro-2'H-spiro[pyrrolidine-3,3'-quinoline]-1-carbonitrile
7'-(1-methyl-1H-indazol-5-yl)-2'-oxo-1',4'-dihydro-2'H-spiro[pyrrolidine-3,3'-quinoline]-1-carbonitrile
7'-(5-methyl-1H-indazol-4-yl)-2'-oxo-1',4'-dihydro-2'H-spiro[pyrrolidine-3,3'-quinoline]-1-carbonitrile
N-(3-(1-cyano-2'-oxo-1',4'-dihydro-2'H-spiro[pyrrolidine-3,3'-quinolin]-7'-yl)phenyl)cyclopropanesulfonamide
7'-(3-methyl-1H-pyrazol-4-yl)-2'-oxo-1',4'-dihydro-2'H-spiro[pyrrolidine-3,3'-quinoline]-1-carbonitrile
2'-oxo-7'-(pyrimidin-5-yl)-1',4'-dihydro-2'H-spiro[pyrrolidine-3,3'-quinoline]-1-carbonitrile
N-(3-(1-cyano-2'-oxo-1',4'-dihydro-2'H-spiro[pyrrolidine-3,3'-quinolin]-7'-yl)phenyl)acetamide
3-(1-cyano-2'-oxo-1',4'-dihydro-2'H-spiro[pyrrolidine-3,3'-quinolin]-7'-yl)-N,N-dimethylbenzamide
N-(4-(1-cyano-2'-oxo-1',4'-dihydro-2'H-spiro[pyrrolidine-3,3'-quinolin]-7'-yl)phenyl)acetamide
7'-(4-(morpholinosulfonyl)phenyl)-2'-oxo-1',4'-dihydro-2'H-spiro[pyrrolidine-3,3'-quinoline]-1-carbonitrile
7'-(3,5-dimethyl-1H-pyrazol-4-yl)-2'-oxo-1',4'-dihydro-2'H-spiro[pyrrolidine-3,3'-quinoline]-1-carbonitrile
7'-(2-methylpyridin-4-yl)-2'-oxo-1',4'-dihydro-2'H-spiro[pyrrolidine-3,3'-quinoline]-1-carbonitrile
2'-oxo-7'-(3-(piperidin-1-yl)phenyl)-1',4'-dihydro-2'H-spiro[pyrrolidine-3,3'-quinoline]-1-carbonitrile
N-(2-(1-cyano-2'-oxo-1',4'-dihydro-2'H-spiro[pyrrolidine-3,3'-quinolin]-7'-yl)phenyl)acetamide
7'-(4-(morpholine-4-carbonyl)phenyl)-2'-oxo-1',4'-dihydro-2'H-spiro[pyrrolidine-3,3'-quinoline]-1-carbonitrile
7'-(3-(morpholinosulfonyl)phenyl)-2'-oxo-1',4'-dihydro-2'H-spiro[pyrrolidine-3,3'-quinoline]-1-carbonitrile
7'-(1-methyl-6-oxo-1,6-dihydropyridin-3-yl)-2'-oxo-1',4'-dihydro-2'H-spiro[pyrrolidine-3,3'-quinoline]-1-carbonitrile
7'-(2-methylbenzo[d]thiazol-5-yl)-2'-oxo-1',4'-dihydro-2'H-spiro[pyrrolidine-3,3'-quinoline]-1-carbonitrile
2'-oxo-6'-phenyl-1',4'-dihydro-2'H-spiro[pyrrolidine-3,3'-quinoline]-1-carbonitrile
6'-(4-cyanophenyl)-2'-oxo-1',4'-dihydro-2'H-spiro[pyrrolidine-3,3'-quinoline]-1-carbonitrile
6'-(3-cyanophenyl)-2'-oxo-1',4'-dihydro-2'H-spiro[pyrrolidine-3,3'-quinoline]-1-carbonitrile
6'-(4-fluorophenyl)-2'-oxo-1',4'-dihydro-2'H-spiro[pyrrolidine-3,3'-quinoline]-1-carbonitrile
6'-(3-fluorophenyl)-2'-oxo-1',4'-dihydro-2'H-spiro[pyrrolidine-3,3'-quinoline]-1-carbonitrile
1-cyano-N,N-dimethyl-2'-oxo-1',4'-dihydro-2'H-spiro[pyrrolidine-3,3'-quinoline]-7'-carboxamide
1-cyano-N-methyl-2'-oxo-1',4'-dihydro-2'H-spiro[pyrrolidine-3,3'-quinoline]-7'-carboxamide
2-oxo-1,2-dihydrospiro[pyrido[2,3-b][1,4]oxazine-3,3'-pyrrolidine]-1'-carbonitrile
2-oxo-7-phenyl-1,2-dihydrospiro[pyrido[2,3-b][1,4]oxazine-3,3'-pyrrolidine]-1'-carbonitrile
7-(4-cyanophenyl)-2-oxo-1,2-dihydrospiro[pyrido[2,3-b][1,4]oxazine-3,3'-pyrrolidine]-1'-carbonitrile
7-(3-cyanophenyl)-2-oxo-1,2-dihydrospiro[pyrido[2,3-b][1,4]oxazine-3,3'-pyrrolidine]-1'-carbonitrile
7-(4-fluorophenyl)-2-oxo-1,2-dihydrospiro[pyrido[2,3-b][1,4]oxazine-3,3'-pyrrolidine]-1'-carbonitrile
7-(3-fluorophenyl)-2-oxo-1,2-dihydrospiro[pyrido[2,3-b][1,4]oxazine-3,3'-pyrrolidine]-1'-carbonitrile
2-oxo-6-phenyl-1,2-dihydrospiro[pyrido[2,3-b][1,4]oxazine-3,3'-pyrrolidine]-1'-carbonitrile
2-oxo-1,4-dihydro-2H-spiro[pyrido[2,3-b]pyrazine-3,3'-pyrrolidine]-1'-carbonitrile
2-oxo-6-(trifluoromethyl)-1,4-dihydro-2H-spiro[pyrido[2,3-b]pyrazine-3,3'-pyrrolidine]-1'-carbonitrile
2-oxo-7-phenyl-1,4-dihydro-2H-spiro[pyrido[2,3-b]pyrazine-3,3'-pyrrolidine]-1'-carbonitrile
7-(4-cyanophenyl)-2-oxo-1,4-dihydro-2H-spiro[pyrido[2,3-b]pyrazine-3,3'-pyrrolidine]-1'-carbonitrile
7-(4-fluorophenyl)-2-oxo-1,4-dihydro-2H-spiro[pyrido[2,3-b]pyrazine-3,3'-pyrrolidine]-1'-carbonitrile
7-(3-fluorophenyl)-2-oxo-1,4-dihydro-2H-spiro[pyrido[2,3-b]pyrazine-3,3'-pyrrolidine]-1'-carbonitrile
3-oxo-3,4-dihydro-H-spiro[pyrido[2,3-b]pyrazine-2,3'-pyrrolidine]-1'-carbonitrile
6-oxo-2,7-diazaspiro[4.4]nonane-2-carbonitrile
(R)-6-oxo-2,7-diazaspiro[4.4]nonane-2-carbonitrile
(S)-2-oxo-7-phenyl-1,2-dihydrospiro[pyrido[2,3-b][1,4]oxazine-3,3'-pyrrolidine]-1'-carbonitrile
(S)-2-oxo-1,2-dihydrospiro[pyrido[2,3-b][1,4]oxazine-3,3'-pyrrolidine]-1'-carbonitrile
(S)-2-oxo-1,4-dihydro-2H-spiro[pyrido[2,3-b]pyrazine-3,3'-pyrrolidine]-1'-carbonitrile
(R)-2'-oxo-6'-phenyl-1',4'-dihydro-2'H-spiro[pyrrolidine-3,3'-quinoline]-1-carbonitrile
(S)-2-oxo-7-phenyl-1,4-dihydro-2H-spiro[pyrido[2,3-b]pyrazine-3,3'-pyrrolidine]-1'-carbonitrile
(S)-7-(3-fluorophenyl)-2-oxo-1,2-dihydrospiro[pyrido[2,3-b][1,4]oxazine-3,3'-pyrrolidine]-1'-carbonitrile
(S)-7-(4-cyanophenyl)-2-oxo-1,2-dihydrospiro[pyrido[2,3-b][1,4]oxazine-3,3'-pyrrolidine]-1'-carbonitrile
(S)-7-(3-cyanophenyl)-2-oxo-1,2-dihydrospiro[pyrido[2,3-b][1,4]oxazine-3,3'-pyrrolidine]-1'-carbonitrile
(S)-7-(4-fluorophenyl)-2-oxo-1,4-dihydro-2H-spiro[pyrido[2,3-b]pyrazine-3,3'-pyrrolidine]-1'-carbonitrile
(S)-7-(3-fluorophenyl)-2-oxo-1,4-dihydro-2H-spiro[pyrido[2,3-b]pyrazine-3,3'-pyrrolidine]-1'-carbonitrile
(S)-7-(4-fluorophenyl)-2-oxo-1,2-dihydrospiro[pyrido[2,3-b][1,4]oxazine-3,3'-pyrrolidine]-1'-carbonitrile
(S)-7-(3-cyanophenyl)-2-oxo-1,4-dihydro-2H-spiro[pyrido[2,3-b]pyrazine-3,3'-pyrrolidine]-1'-carbonitrile
(8R)-8-methyl-7,10-dioxo-2,6,9-triazaspiro[4.5]decane-2-carbonitrile
7,10-dioxo-2,6,9-triazaspiro[4.5]decane-2-carbonitrile (8S)-8-methyl-7,10-dioxo-2,6,9-triazaspiro[4.5]decane-2-carbonitrile
7,10-dioxo-8-phenyl-2,6,9-triazaspiro[4.5]decane-2-carbonitrile
8-ethyl-6-oxo-2,7-diazaspiro[4.4]nonane-2-carbonitrile
8-benzyl-6-oxo-2,7-diazaspiro[4.4]nonane-2-carbonitrile
8-methyl-6-oxo-2,7-diazaspiro[4.4]nonane-2-carbonitrile
2-oxo-1,5-dihydro-2H-spiro[benzo[e][1,4]oxazepine-3,3'-pyrrolidine]-1'-carbonitrile
2-oxo-1,2,4,5-tetrahydrospiro[pyrido[2,3-b][1,4]diazepine-3,3'-pyrrolidine]-1'-carbonitrile
8-methyl-7,10-dioxo-8-phenyl-2,6,9-triazaspiro[4.5]decane-2-carbonitrile
2-oxo-6-phenyl-1,4-dihydro-2H-spiro[pyrido[2,3-b]pyrazine-3,3'-pyrrolidine]-1'-carbonitrile
7-(5-methyl-1H-indazol-4-yl)-2-oxo-1,4-dihydro-2H-spiro[pyrido[2,3-b]pyrazine-3,3'-pyrrolidine]-1'-carbonitrile
7-(1,4-dimethyl-1H-pyrazol-5-yl)-2-oxo-1,4-dihydro-2H-spiro[pyrido[2,3-b]pyrazine-3,3'-pyrrolidine]-1'-carbonitrile
(R)-7'-(5-methyl-1H-indazol-4-yl)-2'-oxo-1',4'-dihydro-2'H-spiro[pyrrolidine-3,3'-quinoline]-1-carbonitrile
(R)-7'-(4-(4-methylpiperazin-1-yl)phenyl)-2'-oxo-1',4'-dihydro-2'H-spiro[pyrrolidine-3,3'-quinoline]-1-carbonitrile
7'-(1H-indazol-4-yl)-2'-oxo-1',4'-dihydro-2'H-spiro[pyrrolidine-3,3'-quinoline]-1-carbonitrile
6'-(1H-indazol-4-yl)-2'-oxo-1',4'-dihydro-2'H-spiro[pyrrolidine-3,3'-quinoline]-1-carbonitrile
(R)-7'-(1H-indazol-4-yl)-2'-oxo-1',4'-dihydro-2'H-spiro[pyrrolidine-3,3'-quinoline]-1-carbonitrile
(S)-7'-(1H-indazol-4-yl)-2'-oxo-1',4'-dihydro-2'H-spiro[pyrrolidine-3,3'-quinoline]-1-carbonitrile
(R)-6'-(1H-indazol-4-yl)-2'-oxo-1',4'-dihydro-2'H-spiro[pyrrolidine-3,3'-quinoline]-1-carbonitrile
1'-cyano-N-(4-fluorophenyl)-2-oxo-1,2-dihydrospiro[pyrido[2,3-b][1,4]oxazine-3,3'-pyrrolidine]-6-carboxamide
2-oxo-6-(piperidine-1-carbonyl)-1,2-dihydrospiro[pyrido[2,3-b][1,4]oxazine-3,3'-pyrrolidine]-1'-carbonitrile
7-(1H-indazol-4-yl)-2-oxo-1,2-dihydrospiro[pyrido[2,3-b][1,4]oxazine-3,3'-pyrrolidine]-1'-carbonitrile
6-(1H-indazol-4-yl)-2-oxo-1,2-dihydrospiro[pyrido[2,3-b][1,4]oxazine-3,3'-pyrrolidine]-1'-carbonitrile
(S)-7-(1H-indazol-4-yl)-2-oxo-1,2-dihydrospiro[pyrido[2,3-b][1,4]oxazine-3,3'-pyrrolidine]-1'-carbonitrile
(S)-6-(1H-indazol-4-yl)-2-oxo-1,2-dihydrospiro[pyrido[2,3-b][1,4]oxazine-3,3'-pyrrolidine]-1'-carbonitrile
(S)-1'-cyano-N-(4-fluorophenyl)-2-oxo-1,2-dihydrospiro[pyrido[2,3-b][1,4]oxazine-3,3'-pyrrolidine]-6-carboxamide
1'-cyano-2-oxo-N-phenyl-1,2-dihydrospiro[pyrido[2,3-b][1,4]oxazine-3,3'-pyrrolidine]-6-carboxamide
1'-cyano-N-(2-fluorophenyl)-2-oxo-1,2-dihydrospiro[pyrido[2,3-b][1,4]oxazine-3,3'-pyrrolidine]-6-carboxamide
7-(1-methyl-1H-indazol-4-yl)-2-oxo-1,2-dihydrospiro[pyrido[2,3-b][1,4]oxazine-3,3'-pyrrolidine]-1'-carbonitrile
(R)-7-(1-methyl-1H-indazol-4-yl)-2-oxo-1,2-dihydrospiro[pyrido[2,3-b][1,4]oxazine-3,3'-pyrrolidine]-1'-carbonitrile
(S)-7-(1-methyl-1H-indazol-4-yl)-2-oxo-1,2-dihydrospiro[pyrido[2,3-b][1,4]oxazine-3,3'-pyrrolidine]-1'-carbonitrile
7-(1-(2-hydroxyethyl)-1H-indazol-4-yl)-2-oxo-1,2-dihydrospiro[pyrido[2,3-b][1,4]oxazine-3,3'-pyrrolidine]-1'-carbonitrile
(R)-7-(1-(2-hydroxyethyl)-1H-indazol-4-yl)-2-oxo-1,2-dihydrospiro[pyrido[2,3-b][1,4]oxazine-3,3'-pyrrolidine]-1'-carbonitrile
(S)-7-(1-(2-hydroxyethyl)-1H-indazol-4-yl)-2-oxo-1,2-dihydrospiro[pyrido[2,3-b][1,4]oxazine-3,3'-pyrrolidine]-1'-carbonitrile
7-(1-(2-methoxyethyl)-1H-indazol-4-yl)-2-oxo-1,2-dihydrospiro[pyrido[2,3-b][1,4]oxazine-3,3'-pyrrolidine]-1'-carbonitrile
(R)-7-(1-(2-methoxyethyl)-1H-indazol-4-yl)-2-oxo-1,2-dihydrospiro[pyrido[2,3-b][1,4]oxazine-3,3'-pyrrolidine]-1'-carbonitrile
(S)-7-(1-(2-methoxyethyl)-1H-indazol-4-yl)-2-oxo-1,2-dihydrospiro[pyrido[2,3-b][1,4]oxazine-3,3'-pyrrolidine]-1'-carbonitrile
7-(6-methoxy-2-methylpyridin-3-yl)-2-oxo-1,2-dihydrospiro[pyrido[2,3-b][1,4]oxazine-3,3'-pyrrolidine]-1'-carbonitrile
(R)-7-(6-methoxy-2-methylpyridin-3-yl)-2-oxo-1,2-dihydrospiro[pyrido[2,3-b][1,4]oxazine-3,3'-pyrrolidine]-1'-carbonitrile
(S)-7-(6-methoxy-2-methylpyridin-3-yl)-2-oxo-1,2-dihydrospiro[pyrido[2,3-b][1,4]oxazine-3,3'-pyrrolidine]-1'-carbonitrile
2'-oxo-7'-(3-(trifluoromethoxy)phenyl)-1',4'-dihydro-2'H-spiro[pyrrolidine-3,3'-quinoline]-1-carbonitrile
4-(1-cyano-2'-oxo-1',4'-dihydro-2'H-spiro[pyrrolidine-3,3'-quinolin]-7'-yl)-N,N-dimethylbenzamide
7'-(3-(4-methylpiperazine-1-carbonyl)phenyl)-2'-oxo-1',4'-dihydro-2'H-spiro[pyrrolidine-3,3'-quinoline]-1-carbonitrile
7'-(1-methyl-1H-pyrrol-2-yl)-2'-oxo-1',4'-dihydro-2'H-spiro[pyrrolidine-3,3'-quinoline]-1-carbonitrile
6'-([1,1'-biphenyl]-4-yl)-2'-oxo-1',4'-dihydro-2'H-spiro[pyrrolidine-3,3'-quinoline]-1-carbonitrile
6'-(4-(benzyloxy)phenyl)-2'-oxo-1',4'-dihydro-2'H-spiro[pyrrolidine-3,3'-quinoline]-1-carbonitrile
6'-(1-methyl-1H-pyrazol-5-yl)-2'-oxo-1',4'-dihydro-2'H-spiro[pyrrolidine-3,3'-quinoline]-1-carbonitrile
2'-oxo-6'-(3-(trifluoromethoxy)phenyl)-1',4'-dihydro-2'H-spiro[pyrrolidine-3,3'-quinoline]-1-carbonitrile
2'-oxo-6'-(4-phenoxyphenyl)-1',4'-dihydro-2'H-spiro[pyrrolidine-3,3'-quinoline]-1-carbonitrile
6'-(1-methyl-1H-pyrazol-4-yl)-2'-oxo-1',4'-dihydro-2'H-spiro[pyrrolidine-3,3'-quinoline]-1-carbonitrile
5-(1-cyano-2'-oxo-1',4'-dihydro-2'H-spiro[pyrrolidine-3,3'-quinolin]-6'-yl)-N-methylpicolinamide
6'-(2-(benzyloxy)phenyl)-2'-oxo-1',4'-dihydro-2'H-spiro[pyrrolidine-3,3'-quinoline]-1-carbonitrile
4-(1-cyano-2'-oxo-1',4'-dihydro-2'H-spiro[pyrrolidine-3,3'-quinolin]-6'-yl)-N-methylbenzamide
6'-(5-isopropyl-2-methoxyphenyl)-2'-oxo-1',4'-dihydro-2'H-spiro[pyrrolidine-3,3'-quinoline]-1-carbonitrile
6'-(3-((2-chlorobenzyl)oxy)phenyl)-2'-oxo-1',4'-dihydro-2'H-spiro[pyrrolidine-3,3'-quinoline]-1-carbonitrile
6'-(6-methoxypyridin-3-yl)-2'-oxo-1',4'-dihydro-2'H-spiro[pyrrolidine-3,3'-quinoline]-1-carbonitrile
6'-(5-fluoro-2-isopropoxyphenyl)-2'-oxo-1',4'-dihydro-2'H-spiro[pyrrolidine-3,3'-quinoline]-1-carbonitrile
6'-(3-methyl-1H-indazol-6-yl)-2'-oxo-1',4'-dihydro-2'H-spiro[pyrrolidine-3,3'-quinoline]-1-carbonitrile
6'-(4-(4-methylpiperazine-1-carbonyl)phenyl)-2'-oxo-1',4'-dihydro-2'H-spiro[pyrrolidine-3,3'-quinoline]-1-carbonitrile 6'-(1-methyl-1H-indazol-5-yl)-2'-oxo-1',4'-dihydro-2'H-spiro[pyrrolidine-3,3'-quinoline]-1-carbonitrile 6'-(5-methyl-1H-indazol-4-yl)-2'-oxo-1',4'-dihydro-2'H-spiro[pyrrolidine-3,3'-quinoline]-1-carbonitrile N-(3-(1-cyano-2'-oxo-1',4'-dihydro-2'H-spiro[pyrrolidine-3,3'-quinolin]-6'-yl)phenyl)cyclopropanesulfonamide 4-(1-cyano-2'-oxo-1',4'-dihydro-2'H-spiro[pyrrolidine-3,3'-quinolin]-6'-yl)-N,N-dimethylbenzamide 2'-oxo-6'-(pyrimidin-5-yl)-1',4'-dihydro-2'H-spiro[pyrrolidine-3,3'-quinoline]-1-carbonitrile N-(3-(1-cyano-2'-oxo-1',4'-dihydro-2'H-spiro[pyrrolidine-3,3'-quinolin]-6'-yl)phenyl)acetamide N-(4-(1-cyano-2'-oxo-1',4'-dihydro-2'H-spiro[pyrrolidine-3,3'-quinolin]-6'-yl)phenyl)acetamide 6'-(3-(4-methylpiperazine-1-carbonyl)phenyl)-2'-oxo-1',4'-dihydro-2'H-spiro[pyrrolidine-3,3'-quinoline]-1-carbonitrile 6'-(1-methyl-1H-pyrrol-2-yl)-2'-oxo-1',4'-dihydro-2'H-spiro[pyrrolidine-3,3'-quinoline]-1-carbonitrile 6'-(4-(morpholinosulfonyl)phenyl)-2'-oxo-1',4'-dihydro-2'H-spiro[pyrrolidine-3,3'-quinoline]-1-carbonitrile 6'-(3,5-dimethyl-1H-pyrazol-4-yl)-2'-oxo-1',4'-dihydro-2'H-spiro[pyrrolidine-3,3'-quinoline]-1-carbonitrile 2'-oxo-6'-(3-(piperidin-1-yl)phenyl)-1',4'-dihydro-2'H-spiro[pyrrolidine-3,3'-quinoline]-1-carbonitrile N-(2-(1-cyano-2'-oxo-1',4'-dihydro-2'H-spiro[pyrrolidine-3,3'-quinolin]-6'-yl)phenyl)acetamide 6'-(4-(morpholine-4-carbonyl)phenyl)-2'-oxo-1',4'-dihydro-2'H-spiro[pyrrolidine-3,3'-quinoline]-1-carbonitrile 6'-(3-(morpholinosulfonyl)phenyl)-2'-oxo-1',4'-dihydro-2'H-spiro[pyrrolidine-3,3'-quinoline]-1-carbonitrile 6'-(1-methyl-6-oxo-1,6-dihydropyridin-3-yl)-2'-oxo-1',4'-dihydro-2'H-spiro[pyrrolidine-3,3'-quinoline]-1-carbonitrile 6'-(2-methylbenzo[d]thiazol-5-yl)-2'-oxo-1',4'-dihydro-2'H-spiro[pyrrolidine-3,3'-quinoline]-1-carbonitrile 6'-(3,5-dimethylisoxazol-4-yl)-2'-oxo-1',4'-dihydro-2'H-spiro[pyrrolidine-3,3'-quinoline]-1-carbonitrile 6'-(2-chloro-5-(trifluoromethoxy)phenyl)-2'-oxo-1',4'-dihydro-2'H-spiro[pyrrolidine-3,3'-quinoline]-1-carbonitrile 6'-(4-(4-methylpiperazin-1-yl)phenyl)-2'-oxo-1',4'-dihydro-2'H-spiro[pyrrolidine-3,3'-quinoline]-1-carbonitrile N-benzyl-4-(1-cyano-2'-oxo-1',4'-dihydro-2'H-spiro[pyrrolidine-3,3'-quinolin]-6'-yl)benzamide 6'-(3-methyl-1H-pyrazol-4-yl)-2'-oxo-1',4'-dihydro-2'H-spiro[pyrrolidine-3,3'-quinoline]-1-carbonitrile 6'-(4-(morpholinomethyl)phenyl)-2'-oxo-1',4'-dihydro-2'H-spiro[pyrrolidine-3,3'-quinoline]-1-carbonitrile 3-(1-cyano-2'-oxo-1',4'-dihydro-2'H-spiro[pyrrolidine-3,3'-quinolin]-6'-yl)-N,N-dimethylbenzamide and 6'-(2-methylpyridin-4-yl)-2'-oxo-1',4'-dihydro-2'H-spiro[pyrrolidine-3,3'-quinoline]-1-carbonitrile.

It should be noted that each of the chemical compounds listed above represents a particular and independent aspect of the invention.

According to a further aspect of the invention there is provided a process for the preparation of a compound of formula I or a pharmaceutically acceptable salt thereof comprising the steps of reacting an amine of formula II with cyanogen bromide to form N—CN compounds:

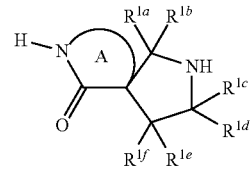

Where $R^{1a}$-$R^{1f}$ and A are as defined elsewhere.

According to a further aspect of the invention there is provided a pharmaceutical composition comprising a compound of the invention.

Pharmaceutical compositions of this invention comprise any of the compounds of the invention combined with any pharmaceutically acceptable carrier, adjuvant or vehicle. Examples of pharmaceutically acceptable carriers, are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of the invention may be used in the treatment of disorders and diseases related to DUB inhibition, particularly Cezanne 1 and USP30 inhibition.

According to a further aspect of the invention there is provided a compound of formula (I) or pharmaceutical composition thereof for use in therapy. In particular, the compounds of the invention have use in the treatment of cancer and more particularly in the treatment of cancer linked to DUB activity. Compounds of the invention may be useful against any DUB enzyme, including but not limited to Cezanne 1 and USP30.

The compounds described herein may be used in the manufacture of a medicament for the treatment of cancer linked to DUB activity.

In a further aspect of the invention there is provided a method of treatment or prevention of cancer linked to Cezanne 1 or USP30 activity, the method comprising administering a pharmaceutically effective amount of a compound of the invention or a pharmaceutical composition thereof to an individual suffering from cancer linked to Cezanne 1 or USP30 activity.

The compounds or compositions disclosed herein may be used to treat cancer. References to "cancer" or "tumour" include but are not limited to breast, ovarian, prostate, lung, kidney, gastric, colon, testicular, head and neck, pancreas, brain, melanoma, bone or other cancers of tissue organs and cancers of the blood cells such as lymphomas and leukaemias. Particular cancers include lymphoma, multiple myeloma, colorectal cancer, and non-small cell lung carcinoma.

The compounds or compositions disclosed herein may be used to treat additional diseases linked to Cezanne 1 activity.

The compounds of the invention or pharmaceutical compositions thereof as described herein may be combined with one or more additional agents. The compounds may be combined with one or more additional anti-tumour therapeutic agents, for example chemotherapeutic drugs or inhibitors of other regulatory proteins. In one embodiment the one or more anti-tumour therapeutic agent is a chemotherapeutic agent. Chemotherapeutic agents may be selected from olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin. In a further embodiment the additional anti-tumour therapeutic agent is a BH-3 mimetic. In a further embodiment BH-3 mimetics may be selected from but not limited to one or more of ABT-737, ABT-199, ABT-263, and Obatoclax.

As mentioned above, inhibition of Cezanne 1 would lead to a reduction in inflammatory response, and therefore the compounds of the invention (Formula (I)) may be used in the treatment of inflammation.

As discussed above, the compounds of the invention may be useful in the treatment of disorders and diseases related to USP30 inhibition. The compounds of the invention may therefore be useful in the treatment of disorders or diseases having a component relating to mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency; and age-dependent decline in cognitive function and muscle strength.

The condition involving mitochondrial dysfunction may be a CNS disorder, for example a neurodegenerative disease. Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

Dosage Forms

The pharmaceutical compositions of the invention may be designed for administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, cachets, granules, capsules, etc. For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

Preparations according to the invention for parenteral administration include sterile aqueous, aqueous-organic, and organic solutions, suspensions and emulsions.

Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration.

These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 μg to about 100 mg per kg body weight of a human and non-human animal and in general may be around 10 μg to 30 mg per kg body weight per dose. The above dose may be given from one to three times per day.

Synthetic methodologies Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All single enantiomers listed were prepared from the corresponding racemic mixture by chiral preparative HPLC or Supercritical Fluid Chromatography (SFC).

All the compounds were characterised by liquid chromatography-mass spectroscopy (LCMS) and/or $^1$H NMR.

ABBREVIATIONS

ABPR Automated back pressure regulator
AIBN Azobisisobutyronitrile
Boc Tert-butoxycarbonyl
br Broad (NMR signal)
CAS Chemical Abstracts Service
d Doublet (NMR signal)
DCM Dichloromethane
DIPEA Diisopropylethylamine
DMF N,N-Dimethylformamide
DMSO Dimethylsulphoxide
dppf 1,1'-Bis(diphenylphosphino)ferrocene
ES Electrospray
EtOAc Ethyl acetate
h Hour(s)
HATU 1-[Bis(dimethylamino)methylene]-1H-1,2,3-triazolo[4,5-b]pyridinium3-oxid hexafluorophosphate
HPLC High performance liquid chromatography
IPA Propan-2-ol
LCMS Liquid chromatography-mass spectrometry
LiHMDS Lithium bis(trimethylsilyl)amide
m Multiplet (NMR signal)
MeCN Acetonitrile
MeOH Methanol
MTBE Methyl tert-butyl ether
NBS N-Bromosuccinimide
n-Bu n-butyl
NMR nuclear magnetic resonance
PE Petroleum Ether
Ph Phenyl
Prep Preparative
psi Pounds per square inch
rt Room temperature
RT Retention time
s Singlet (NMR signal)
t Triplet (NMR signal)
TBD 1,5,7-Triazabicyclo[4.4.0]dec-5-ene
TEA Triethylamine
TFA Trifluoroacetic acid
THF Tetrahydrofuran
TLC Thin layer chromatography
LCMS Methods

| Method 1 | | |
|---|---|---|
| Column | BEH C18, 50 × 2.1 mm, 1.7 μm or equivalent | |
| Mobile Phase | (A) 5 mM Ammonium Acetate + 0.1% Formic Acid in Water | |
| | (B) 0.1% Formic Acid in MeCN | |
| Flow Rate | 0.55 mL/min | |
| | Time | % B |
| Gradient | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

| Method 2 | | |
|---|---|---|
| Column | BEH C18, 50 × 2.1 mm, 1.7 μm or equivalent | |
| Mobile Phase | (A) 5 mM Ammonium Acetate + 0.1% Formic Acid in Water | |
| | (B) 0.1% Formic Acid in MeCN | |
| Flow Rate | 0.45 mL/min | |
| | Time | % B |
| Gradient | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

| Method 3 | | |
|---|---|---|
| Column | X-bridge C18, 50 × 4.6 mm, 3.5 μm or equivalent | |
| Mobile Phase | (A) 0.1% Ammonia in Water | |
| | (B) 0.1% Ammonia in MeCN | |
| Flow Rate | 1.0 mL/min | |
| | Time | % B |
| Gradient | 0.01 | 5 |
| | 5.00 | 90 |
| | 5.80 | 95 |
| | 7.20 | 95 |
| | 7.21 | 5 |
| | 10.00 | 5 |

| Method 4 | |
|---|---|
| Column | X-bridge C18, 250 × 4.6 mm, 5 μm or equivalent |
| Mobile Phase | (A) 0.1% Ammonia in Water<br>(B) 0.1% Ammonia in MeCN |
| Flow Rate | 1.0 mL/min |

| | Time | % B |
|---|---|---|
| Gradient | 0.01 | 5 |
| | 5.00 | 5 |
| | 10.00 | 30 |
| | 15.00 | 30 |
| | 25.00 | 60 |
| | 30.00 | 90 |
| | 35.00 | 90 |
| | 35.01 | 5 |
| | 40.00 | 5 |

| Method 5 | |
|---|---|
| Column | CHIRALPAK IC, 250 × 4.6 mm, 5 μm or equivalent |
| Mobile Phase | (A) 5 mM Ammonium Acetate + 0.1% Formic Acid in Water<br>(B) 0.1% Formic Acid in IPA |
| Flow Rate | 3 mL/min |

| | Time | % B |
|---|---|---|
| Gradient | 0.01 | 55 |
| | 10.00 | 55 |
| | 10.01 | 95 |
| | 11.00 | 95 |
| | 11.01 | 2 |
| | 12.00 | 2 |

| Method 6 | |
|---|---|
| Column | Chiral ART SA 250 × 4.6 mm, 5 μm or equivalent |
| Mobile Phase | (A) Liquid CO2<br>(B) 0.1% Ammonia in IPA |
| Flow Rate | 3.0 mL/min |

| | Time | % B |
|---|---|---|
| Gradient | 0.01 | 2 |
| | 2.00 | 2 |
| | 10.00 | 50 |
| | 15.00 | 50 |

| Method 7 | |
|---|---|
| Column | Xbridge C18, 150 × 19 mm, 5 μm or equivalent |
| Mobile Phase | (A) 20 mM Ammonium Acetate in water<br>(B) MeCN:MeOH (50:50) |
| Flow Rate | 15 mL/min |

| | Time | % B |
|---|---|---|
| Gradient | 0.01 | 0 |
| | 32.00 | 10 |
| | 32.01 | 100 |
| | 35.00 | 100 |
| | 35.01 | 0 |
| | 40.00 | 0 |

| Method 8 | |
|---|---|
| Column | Agilent TC-C18, 50 × 2.1 mm, 5 μm or equivalent |
| Mobile Phase | (A) 0.04% TFA in water<br>(B) 0.02% TFA in MeCN |
| Flow Rate | 0.8 mL/min |

| | Time | % B |
|---|---|---|
| Gradient | 0.00 | 1 |
| | 0.40 | 1 |
| | 3.40 | 100 |
| | 4.00 | 100 |
| | 4.01 | 1 |
| | 4.50 | 1 |

| Method 9 | |
|---|---|
| Column | YMC Triart C18 150 × 4.6 mm, 5 μm or equivalent |
| Mobile Phase | (A) 10 mM Ammonium Acetate in water<br>(B) MeCN |
| Flow Rate | 1.0 mL/min |

| | Time | % B |
|---|---|---|
| Gradient | 0.01 | 0 |
| | 5.00 | 0 |
| | 10.00 | 30 |
| | 13.00 | 70 |
| | 15.00 | 90 |
| | 17.00 | 90 |
| | 17.01 | 0 |
| | 20.00 | 0 |

| Method 10 | |
|---|---|
| Column | XBridge ShieldRP18, 2.1 × 50 mm, 5 μm or equivalent |
| Mobile Phase | (A) 0.05% NH3•H2O in water<br>(B) MeCN |
| Flow Rate | 0.80 mL/min |

| | Time | % B |
|---|---|---|
| Gradient | 0.01 | 5 |
| | 3.40 | 100 |
| | 4.00 | 100 |
| | 4.01 | 5 |
| | 4.50 | 5 |

| Method 11 | |
|---|---|
| Column | Agilent TC-C18, 2.1 × 50 mm, 5 μm or equivalent |
| Mobile Phase | (A) 0.04% TFA in water<br>(B) 0.02% TFA in MeCN |
| Flow Rate | 0.80 mL/min |

| | Time | % B |
|---|---|---|
| Gradient | 0.01 | 10 |
| | 3.40 | 100 |
| | 4.00 | 100 |
| | 4.01 | 10 |
| | 4.50 | 10 |

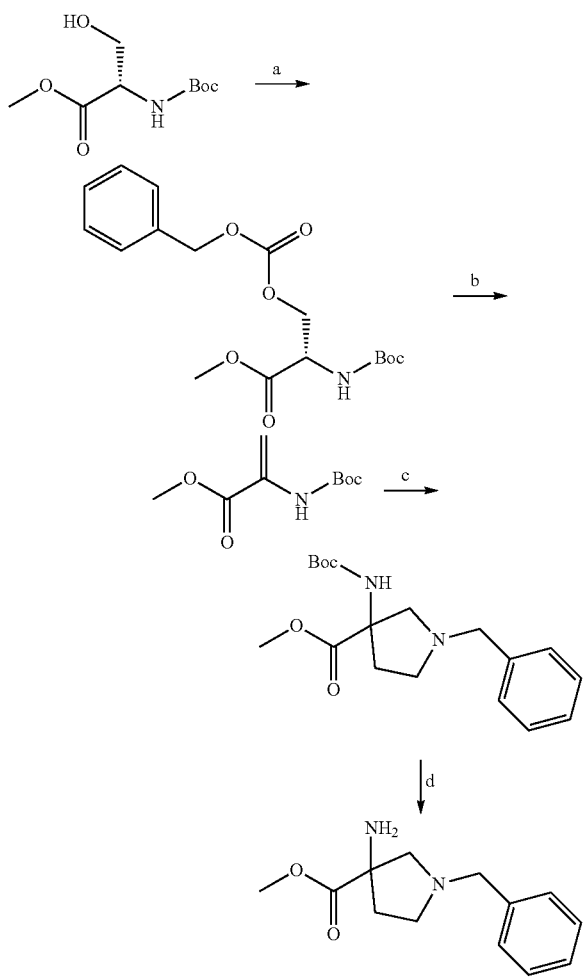

Step a.

To a stirred solution of methyl (tert-butoxycarbonyl)-L-serinate (CAS Number 2766-43-0; 30 g, 136.9 mmol) in DCM (600 ml) was added pyridine (27.03 g, 342.1 mmol) at −50° C. Benzyl chloroformate (23.35 g, 136.9 mmol) was added slowly to the reaction mixture at −50° C. and the reaction mixture was stirred at rt for 16 h. The resulting mixture was poured into 10% citric acid solution (1500 ml) and the organic phase was separated and aqueous phase was re-extracted with DCM (2×300 ml). The combined organic phase was separated, dried over $Na_2SO_4$, filtered and concentrated under reduced pressure. The residue was purified by column chromatography (20% EtOAc in hexane) yielding methyl O-((benzyloxy)carbonyl)-N-(tert-butoxycarbonyl)-L-serinate (22.0 g, 62.323 mmol). LCMS: Method 3, 4.98 min, MS: ES+ 354.2; $^1$H NMR (400 MHz, DMSO-$d_6$) δ ppm: 7.49 (d, J=7.2 Hz, 1H), 7.36-7.39 (m, 5H), 5.16 (s, 2H), 4.35-4.40 (m, 2H), 4.21-4.27 (m, 1H), 3.64 (s, 3H), 1.38 (s, 9H).

Step b.

To a stirred solution of methyl O-((benzyloxy)carbonyl)-N-(tert-butoxycarbonyl)-L-serinate (22.0 g, 62.3 mmol) in DMF (150 ml) was added $K_2CO_3$ (17.2 g, 124.6 mmol) at rt and the reaction mixture was stirred at 65° C. for 1 h. The mixture was cooled to rt, poured into water (2000 ml) and extracted with EtOAc (2×500 ml). The combined organic phase was separated, dried over $Na_2SO_4$, filtered and concentrated under reduced pressure. The residue was purified by flash chromatography (5% EtOAc in hexane) yielding methyl 2-((tert-butoxycarbonyl)amino)acrylate (11.0 g, 54.726 mmol). $^1$H NMR (400 MHz, DMSO-$d_6$) δ ppm: 8.39 (s, 1H), 5.60 (s, 1H), 5.49 (s, 1H), 3.72 (s, 3H), 1.42 (s, 9H).

Step c.

To a stirred solution of methyl 2-((tert-butoxycarbonyl)amino)acrylate (11 g, 54.726 mmol) and N-(methoxymethyl)-N-(trimethylsilylmethyl)benzylamine (CAS Number 93102-05-7; 12.97 g, 54.7 mmol) in DCM (250 ml) was added TFA (0.3 ml) at 0° C. under nitrogen atmosphere. The reaction mixture was stirred at rt for 16 h. The resulting reaction mixture was diluted with DCM (200 ml) and washed with saturated $NaHCO_3$ solution (1500 ml). The organic layer separated and aqueous layer was re-extracted with DCM (2×200 ml). The combined organic phase was separated, dried over $Na_2SO_4$, filtered and concentrated under reduced pressure. The resulting residue was purified by flash chromatography (5-20% EtOAc in hexane) to afford methyl 1-benzyl-3-((tert-butoxycarbonyl)amino)pyrrolidine-3-carboxylate (9.0 g, 26.9 mmol). LCMS: Method 3, 4.69 min, MS: ES+ 335.1; $^1$H NMR (400 MHz, DMSO-$d_6$) δ ppm: 7.59 (s, 1H), 7.28 (m, 4H), 7.22-7.26 (m, 1H), 3.57-3.63 (m, 5H), 2.99 (d, J=10.0 Hz, 1H), 2.68 (d, J=10.0 Hz, 1H), 2.58-2.61 (m, 1H), 2.47-2.49 (m, 1H), 2.17-2.21 (m, 1H), 1.97-1.99 (m, 1H), 1.36 (s, 9H).

Step d.

To a stirred solution of methyl 1-benzyl-3-((tert-butoxycarbonyl)amino)pyrrolidine-3-carboxylate (0.8 g, 2.39 mmol) in DCM (15 ml) was added TFA (4 ml) at 0° C. The reaction mixture was stirred at rt for 16 h. The reaction mixture was concentrated under reduced pressure and azeotropically distilled using DCM (2×20 ml). The resulting residue was dissolved into EtOAc (50 ml) and washed with saturated $NaHCO_3$ solution (3×50 ml). The organic phase was separated, dried over $Na_2SO_4$, filtered and concentrated under reduced pressure yielding methyl 3-amino-1-benzylpyrrolidine-3-carboxylate (0.57 g, quantitative). This material was used directly for the next step without further purification. LCMS: Method 1, 0.90 min, MS: ES+ 235.3; $^1$H NMR (400 MHz, DMSO-$d_6$) δ ppm: 7.22-7.33 (m, 5H), 3.63 (s, 3H), 3.58 (s, 2H), 2.88 (d, J=9.2 Hz, 1H), 2.68 (q, J=7.2 Hz, 1H), 2.54-2.58 (m, 1H), 2.38 (d, J=9.6 Hz, 1H), 2.21-2.25 (m, 1H), 1.61-1.68 (m, 1H).

Intermediate B Tert-butyl 7'-bromo-2'-oxo-1',4'-dihydro-2'H-spiro[pyrrolidine-3,3'-quinoline]-1-carboxylate

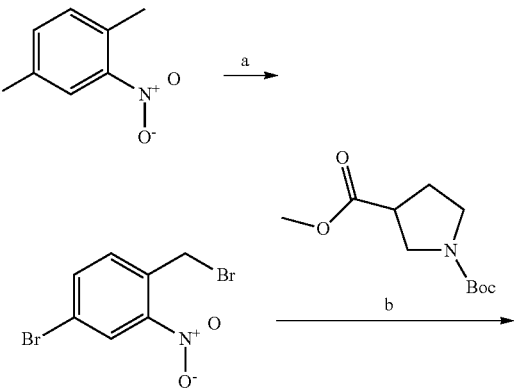

-continued

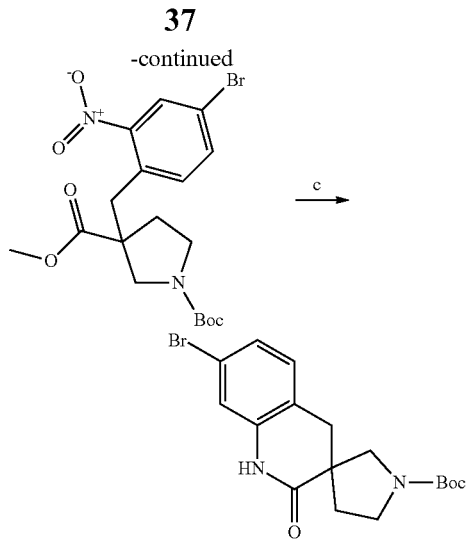

Reagents and conditions: a) NBS, AIBN, CCl$_4$, 76° C., 16 h b) LiHMDS, THF, −78° C., 1 h; rt, 16 h c) Fe, NH$_4$Cl, THF/water, 60° C., 16 h.

Step a.

To a mixture of 4-bromo-1-methyl-2-nitro-benzene (60 g, 277 mmol, 1.0 eq) and NBS (59.3 g, 333 mmol, 1.2 eq) in CCl$_4$ (600 mL) was added AIBN (5.47 g, 33.3 mmol, 0.12 eq) at rt under N$_2$. The mixture was stirred at 76° C. for 16 h. The reaction mixture was filtered and the filtrate was washed with 2M NaHCO$_3$ (2×250 ml) and brine (400 ml), dried over Na$_2$SO$_4$, filtered and concentrated under reduced pressure to give a residue. The residue was purified by silica gel chromatography (0-5% EtOAc/PE) to provide 4-bromo-1-(bromomethyl)-2-nitro-benzene (40 g, 135 mmol, 48.8% yield) as a yellow solid. $^1$H NMR (400 MHz, CDCl$_3$) δ ppm: 8.19 (d, J=1.6 Hz, 1H), 7.75 (dd, J=8.4, 2.0 Hz, 1H), 7.47 (d, J=8.4 Hz, 1H), 4.78 (s, 2H).

Step b.

To a mixture of 1-(tert-butyl) 3-methyl pyrrolidine-1,3-dicarboxylate (31.1 g, 135 mmol, 1.0 eq) in THF (450 ml) was added dropwise LiHMDS (1 M, 203 ml, 1.5 eq) at −78° C. under N$_2$. The mixture was stirred at −78° C. for 30 min, then a solution of 4-bromo-1-(bromomethyl)-2-nitro-benzene (40 g, 135 mmol, 1.0 eq) in THF (150 ml) was added dropwise at −78° C. The mixture was stirred at −78° C. for 1 h, then stirred at rt for 16 h. LCMS showed the desired compound was detected. The reaction mixture was quenched by addition saturated NH$_4$Cl solution (500 ml) at rt, and then extracted with EtOAc (5×500 ml). The combined organic layers were washed with brine (2×1000 ml), dried over Na$_2$SO$_4$, filtered and concentrated under reduced pressure. The residue was purified by silica gel chromatography (0~30% EtOAc/PE). 1-(Tert-butyl) 3-methyl 3-[(4-bromo-2-nitro-phenyl)methyl]-pyrrolidine-1,3-dicarboxylate (15 g, 33.8 mmol, 24.9% yield) was obtained as a yellow liquid. $^1$H NMR (400 MHz, CDCl$_3$) δ ppm: 8.04 (d, J=10.0 Hz, 1H), 7.61-7.68 (m, 1H), 7.13 (dd, J=8.0, 2.0 Hz, 1H), 3.70-3.76 (m, 1H), 3.64 (s, 3H), 3.23-3.49 (m, 5H), 2.25-2.37 (m, 1H), 1.78-1.92 (m, 1H), 1.46 (s, 9H).

Step c.

To a mixture of 1-(tert-butyl) 3-methyl 3-[(4-bromo-2-nitro-phenyl)methyl]pyrrolidine-1,3-dicarboxylate (15 g, 33.8 mmol, 1.0 eq) in THF (250 ml) and water (250 ml) was added Fe (18.9 g, 338 mmol, 10.0 eq) and NH$_4$Cl (18.1 g, 338 mmol, 11.8 ml, 10.0 eq) at 0° C. The mixture was stirred at 60° C. for 16 h. The reaction mixture was filtered, and the filtrate was diluted with water (50 ml) and extracted with EtOAc (5×50 ml). The combined organic layers were washed with brine (2×60 ml), dried over Na$_2$SO$_4$, filtered and concentrated under reduced pressure to give a residue. The residue was purified by silica gel chromatography (Eluent of 0-5% DCM/MeOH). Tert-butyl 7'-bromo-2'-oxo-1',4'-dihydro-2'H-spiro[pyrrolidine-3,3'-quinoline]-1-carboxylate (12 g, 31.4 mmol, 93.0% yield) was obtained as a yellow solid. $^1$H NMR (400 MHz, DMSO-d$_6$) δ ppm: 10.34 (s, 1H), 7.07-7.16 (m, 2H), 7.03 (s, 1H), 3.50-3.57 (m, 1H), 3.24-3.34 (m, 1H), 3.06 (dd, J=10.8, 2.8 Hz, 1H), 2.89 (q, J=11.6 Hz, 2H), 1.94-2.02 (m, 1H), 1.63-1.75 (m, 1H), 1.37 (s, 9H).

Intermediate C 1-(Tert-butyl) 3-methyl 3-hydroxypyrrolidine-1,3-dicarboxylate

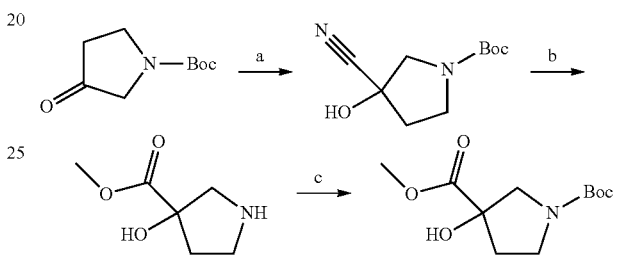

Reagents and conditions: a) NaCN, NaHCO$_3$, Et$_2$O, water; b) HCl, 1,4-dioxane, water; c) Boc$_2$O, EtOAc, NaHCO$_3$ (aq); d) Cs$_2$CO$_3$, DMF; e) Fe, NH$_4$Cl, THF, water; f) TFA, DCM; g) CNBr, K$_2$CO$_3$, THF Step a.

To a stirred solution of N-Boc-3-pyrrolidinone (CAS Number 101385-93-7; 4.0 g, 21.6 mmol) in diethyl ether (50 ml) and water (8 ml) was added NaHCO$_3$ (3.6 g, 43 mmol) in water (5 ml) at 0° C. NaCN (3.17 g, 64.8 mmol) was added to the reaction mixture at 0° C. The reaction mixture was stirred at rt for 24 h. The resulting reaction mixture was poured into water (500 ml) and extracted with diethyl ether (2×300 ml). The combined organic phase was dried over Na$_2$SO$_4$, filtered and concentrated under reduced pressure yielding tert-butyl 3-cyano-3-hydroxypyrrolidine-1-carboxylate (4.21 g, 19.9 mmol). This material was used directly for the next step without further purification. $^1$H NMR (400 MHz, DMSO-d6) δ ppm: 6.90 (s, 1H), 3.48-3.63 (m, 2H), 3.36-3.44 (m, 1H), 3.20-3.32 (m, 1H), 2.27-2.33 (m, 1H), 2.13-2.20 (m, 1H), 1.42 (s, 9H).

Step b.

To a stirred solution of tert-butyl 3-cyano-3-hydroxypyrrolidine-1-carboxylate (4.2 g, 19.8 mmol) in MeOH (10.5 ml) was added 4M HCl in 1,4-dioxane (42 ml) at 0° C. The reaction mixture was stirred at rt for 3 h. The excess of solvent was distilled under reduced pressure yielding methyl 3-hydroxypyrrolidine-3-carboxylate HCl salt (4.2 g, quantitative). This material was used directly for the next step without further purification. LCMS: Method 3, 1.140 min, MS: ES+ 146.07.

Step c.

To a stirred solution of methyl 3-hydroxypyrrolidine-3-carboxylate HCl salt (4.2 g, 23.204 mmol) in EtOAc (42 ml) was added saturated NaHCO$_3$ solution (42 ml) at rt. Boc anhydride (10.12 g, 46.4 mmol) was added to the reaction mixture at rt. The reaction mixture was stirred at rt for 16 h. The resulting reaction mixture was poured into saturated NaHCO₃ (200 ml) and extracted with EtOAc (2×100 ml). The combined organic phase was dried over Na₂SO₄, filtered and concentrated under reduced pressure. The resulting residue was purified by flash chromatography (30% EtOAc in hexane) yielding 1-(tert-butyl) 3-methyl 3-hydroxypyrrolidine-1,3-dicarboxylate (2.2 g, 8.979 mmol). LCMS: Method 1, 1.90 min, MS: ES+ 246.2; ¹H NMR (400 MHz, DMSO-d6) δ ppm: 5.87 (s, 1H), 3.68 (s, 3H), 3.41-3.52 (m, 2H), 3.28-3.32 (M, 2H), 2.09-2.18 (m, 1H), 1.91-1.94 (m, 1H), 1.39 (s, 9H).

Intermediate D Tert-butyl 7-bromo-2-oxo-1,2-dihydrospiro[pyrido[2,3-b][1,4]oxazine-3,3'-pyrrolidine]-1'-carboxylate

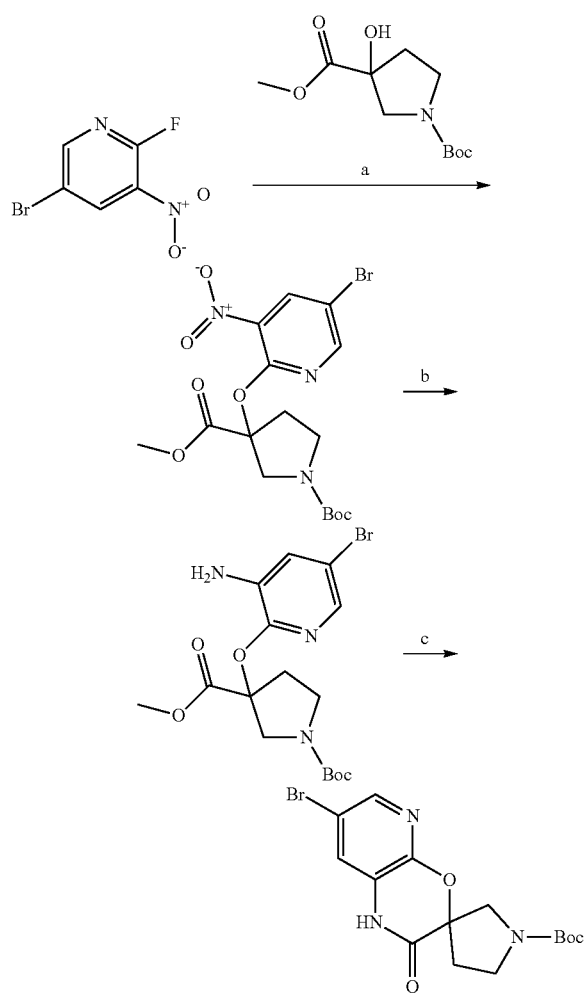

Step a.

To a stirred solution of 1-(tert-butyl) 3-methyl 3-hydroxypyrrolidine-1,3-dicarboxylate (Intermediate C; 0.5 g, 2.04 mmol) in THF (30 ml) was added sodium bis(trimethylsilyl) amide solution (1M in THF; 2.04 ml, 2.04 mmol) dropwise at −78° C. The reaction mixture was stirred at −78° C. for 5 min. A solution of 2-fluoro-3-nitro-5-bromopyridine (CAS Number 886372-98-1; 0.493 g, 2.24 mmol) in THF (1 ml) was added to the reaction mixture at −78° C. The reaction mixture was stirred at −78° C. to −40° C. for 5 h. The resulting reaction mixture was quenched by slow addition of saturated ammonium chloride solution (20 ml) at −40° C. The resulting reaction mixture was warmed to rt and combined with three other batches on the same scale prepared by an identical method. The reaction mixture was diluted with water (50 ml) and extracted with EtOAc (3×50 ml). The combined organic phase was separated and washed with brine (30 ml). The organic phase was separated, dried over Na₂SO₄, filtered and concentrated under reduced pressure. The resulting residue was purified by flash chromatography (12% EtOAc in hexane) yielded 1-(tert-butyl) 3-methyl 3-((5-bromo-3-nitropyridin-2-yl)oxy)pyrrolidine-1,3-dicarboxylate (1.65 g, 3.697 mmol). LCMS: Method 1, 2.539 min, MS: ES+ 390.2, 392.2 (M-2) (M-56); ¹H NMR (400 MHz, DMSO-d₆) δ ppm: 8.78 (s, 1H), 8.63 (s, 1H), 4.00 (d, J=12.0 Hz, 1H), 3.70 (d, J=12.8 Hz, 1H), 3.65 (s, 3H), 3.48-3.54 (m, 1H), 3.37-3.46 (m, 1H), 2.39-2.45 (m, 2H), 1.39 (d, J=6.4 Hz, 9H).

Step b.

To a stirred solution of 1-(tert-butyl) 3-methyl 3-((5-bromo-3-nitropyridin-2-yl)oxy)pyrrolidine-1,3-dicarboxylate (0.8 g, 1.793 mmol) in THF:water (1:1; 8 ml), was added iron powder (1.0 g, 17.927 mmol) and ammonium chloride (0.957 g, 17.93 mmol) at rt. The reaction mixture was heated at 70° C. for 18 h. The resulting reaction mixture was cooled to rt and combined with one other batch on the same scale prepared by an identical method. The reaction mixture was filtered through celite hyflow. The celite bed was washed with EtOAc (100 ml). The combined filtrate was poured into water (50 ml). The organic phase was separated and the aqueous phase was re-extracted with EtOAc (3×50 ml). The combined organic phase was washed with brine (50 ml). The combined organic phase was separated, dried over Na₂SO₄, filtered and concentrated under reduced pressure yielding an approximately 2:3 mixture of tert-butyl 7-bromo-2-oxo-1,2-dihydrospiro[pyrido[2,3-b][1,4]oxazine-3,3'-pyrrolidine]-1'-carboxylate and 1-(tert-butyl) 3-methyl 3-((3-amino-5-bromopyridin-2-yl)oxy)pyrrolidine-1,3-dicarboxylate (1.45 g, quantitative). The obtained mixture was used for the next step without further purification. LCMS: Method 1, 2.218 min, 2.429 min, MS: ES+ 328.0, 329.0 (M+2) (M-56), 416.1, 418.1 Step c. To a stirred solution of an approximately 2:3 mixture of tert-butyl 7-bromo-2-oxo-1,2-dihydrospiro[pyrido[2,3-b][1,4]oxazine-3,3'-pyrrolidine]-1'-carboxylate and 1-(tert-butyl) 3-methyl 3-((3-amino-5-bromopyridin-2-yl)oxy)pyrrolidine-1,3-dicarboxylate (0.7 g, 1.689 mmol) in THF (20 ml) was added 1,5,7-triazabicyclo[4.4.0]dec-5-ene (0.235 g, 1.689 mmol) at rt. The reaction mixture was stirred at rt for 3 h. The resulting reaction mixture was combined with one other batch prepared on the same scale by an identical method. The obtained reaction mixture was concentrated under vacuum and the residue was purified by flash chromatography (25% EtOAc in hexane) yielding tert-butyl 7-bromo-2-oxo-1,2-dihydrospiro[pyrido[2,3-b][1,4]oxazine-3,3'-pyrrolidine]-1'-carboxylate (1.3 g, 3.618 mmol). LCMS: Method 1, 2.125 min, MS: ES+ 328.0, 330.0 (M+2) (M-56); ¹H NMR (400 MHz, DMSO-d₆) δ ppm: 11.21 (s, 1H), 7.96 (d, J=2.0 Hz, 1H), 7.40 (d, J=2.4 Hz, 1H), 3.68-3.75 (m, 1H), 3.52-3.60 (m, 2H), 3.64-3.44 (m, 1H), 2.32-2.36 (m, 1H), 2.20-2.22 (m, 1H), 1.40 (d, J=10.0 Hz, 9H).

Intermediate E Methyl
3-amino-1-benzylpyrrolidine-3-carboxylate TFA
Salt

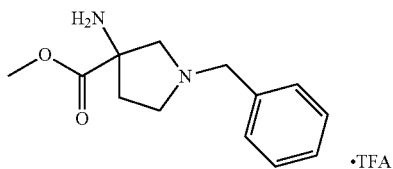 [SMILES: COC(=O)C1(N)CCN(Cc2ccccc2)C1]

Step a.

To a solution of Boc-L-serine methyl ester (CAS Number 2766-43-0; 30.0 g, 136.9 mmol) in DCM (300 ml) was added pyridine (28.8 ml, 342 mmol) at −50° C. and stirred for 15 minutes. Benzyl chloroformate (25.67 g, 150.5 mmol) was added dropwise to the reaction mixture at −50° C. The temperature of the reaction mixture was gradually increased to rt. The resulting reaction mixture was stirred at rt for 15 h. After 15 h more pyridine (22.0 ml, 274 mmol) and benzyl chloroformate (23.3 g, 136.9 mmol) was added at −50° C. and the reaction mixture was stirred at rt for 5 h. The resulting reaction mixture was quenched with 50% citric acid solution (500 ml) and extracted with EtOAc (3×100 ml). The combined organic phase was collected and washed with saturated NaHCO$_3$ solution (50 ml), dried over Na$_2$SO$_4$, filtered and concentrated under reduced pressure. The obtained residue was triturated with n-hexane (200 ml) yielding methyl O-((benzyloxy)carbonyl)-N-(tert-butoxycarbonyl)-L-serinate (33.25 g, 94.155 mmol). LCMS: Method 3, 4.94 min, MS: ES+ 354.1; $^1$H NMR (400 MHz, DMSO-d6) δ ppm: 7.48 (d, J=7.2 Hz, 1H), 7.32-7.41 (m, 5H), 5.14 (s, 2H), 4.36-4.40 (m, 2H), 4.23-4.26 (m, 1H), 3.63 (s, 3H), 1.37 (S, 9H).

Step b.

To a solution of methyl O-((benzyloxy)carbonyl)-N-(tert-butoxycarbonyl)-L-serinate (33.0 g, 93.48 mmol) in DMF (330 ml) was added K$_2$CO$_3$ (25.88 g, 186.97 mmol) at rt. The reaction mixture was heated at 65° C. for 1 h. The resulting reaction mixture was poured into water (1000 ml) and extracted with EtOAc (3×150 ml). The combined organic phase was washed with brine solution (3×50 ml), dried over Na$_2$SO$_4$, filtered and concentrated under reduced pressure. The resulting residue was purified by column chromatography (3% EtOAc in hexane) yielding methyl 2-((tert-butoxycarbonyl)amino)acrylate (10.39 g, 51.66 mmol). LCMS: Method 1, 2.25 min. $^1$H NMR (400 MHz, DMSO-d6) δ ppm: 8.37 (s, 1H), 5.64 (s, 1H), 5.49 (s, 1), 3.72 (s, 3H), 1.41 (s, 9H).

Step c.

To a solution of 2-((tert-butoxycarbonyl)amino)acrylate (10.3 g, 51.24 mmol) in DCM (103 ml) was added TFA (0.26 ml) at 0° C. N-(Methoxymethyl)-N-(trimethylsilylmethyl)-benzylamine (13.35 g, 56.37 mmol) was slowly added to the reaction mixture at 0° C. The reaction mixture was stirred at 0° C. for 15 min and then stirred at rt for 15 h. After 15 h unreacted starting material was observed so again N-(Methoxymethyl)-N-(trimethylsilylmethyl)-benzylamine (3.64 g, 15.373 mmol) was slowly added to the reaction mixture at 0° C. The reaction mixture was stirred at rt for a further 15 h. The resulting reaction mixture was poured into water (250 ml) and basified using Na$_2$CO$_3$. The resulting mixture was extracted with DCM (2×150 ml) and the combined organic phase was washed with brine solution (50 ml), dried over Na$_2$SO$_4$, filtered and concentrated under reduced pressure. The resulting residue was purified by column chromatography (20% EtOAc in hexane) yielding methyl 1-benzyl-3-((tert-butoxycarbonyl)amino)pyrrolidine-3-carboxylate (13.80 g, 41.294 mmol). LCMS: Method 3, 4.68 min, MS: ES+ 335.3; $^1$H NMR (400 MHz, DMSO-d6) δ ppm: 7.59 (s, 1H), 7.21-7.33 (m, 5H), 3.57-3.62 (m, 5H), 2.99 (d, J=10 Hz, 1H), 2.67 (d, J=10 Hz, 1H), 2.50-2.61 (m, 2H), 2.14-2.18 (m, 1H), 1.98-1.99 (m, 1H), 1.35 (s, 9H).

Step d.

To a solution of methyl 1-benzyl-3-((tert-butoxycarbonyl)amino)pyrrolidine-3-carboxylate (2.00 g, 5.99 mmol) in DCM (20 ml) was added TFA (2 ml) at rt. The reaction mixture was stirred at rt for 1 h. The resulting reaction mixture was concentrated under reduced pressure and the obtained residue was triturated with diethyl ether (2×10 ml) yielding methyl 3-amino-1-benzylpyrrolidine-3-carboxylate TFA salt (2.50 g. quantitative). This material was used directly for the next step without further purification. LCMS: Method 1, 0.70 min, MS: ES+ 235.4.

Intermediate F 2-(4-(4,4,5,5-tetramethyl-1,3,2-dioxaborolan-2-yl)-1H-indazol-1-yl)ethan-1-ol

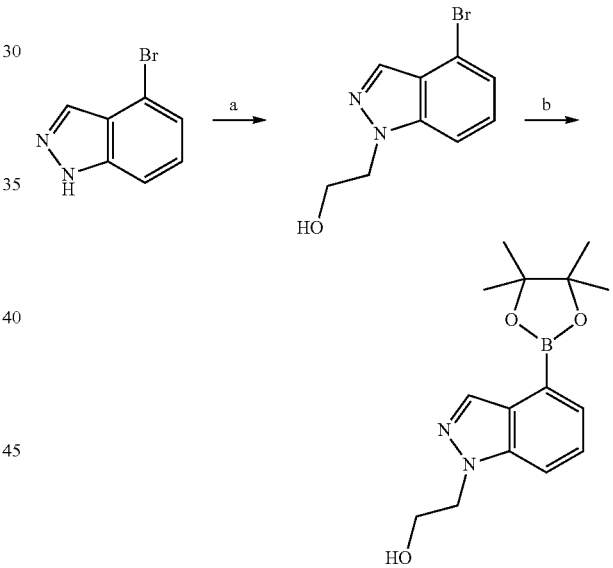

Step a.

To a solution of 4-bromo-1H-indazole (CAS Number 186407-74-9; 1.000 g, 5.076 mmol) in DMF (20 ml) were added 2-bromoethanol (0.43 ml, 6.091 mmol) and K$_2$CO$_3$ (1.400 g, 10.145 mmol) at rt. The reaction mixture was heated to 100° C. for 3 h. The resulting mixture was poured into ice cold water (50 ml). The resulting precipitate was collected by filtration, washed with hexane (50 ml) and dried under high vacuum. The obtained solid material contained a 2:1 regioisomeric ratio by LCMS. The desired product was isolated by column chromatography (23% EtOAc in hexane) yielding 2-(4-bromo-1H-indazol-1-yl)ethan-1-ol (0.700 g, 2.904 mmol). LCMS: Method 1, 1.629 min, MS: ES+ 241.20, 243.20; $^1$H NMR (400 MHz, DMSO-d6) δ ppm: 8.03 (s, 1H), 7.71 (d, J=8.0 Hz, 1H), 7.28-7.36 (m, 2H), 4.87 (t, J=5.6 Hz, 1H), 4.62 (t, J=5.2 Hz, 2H), 3.78-3.82 (m, 2H).

Step b.

To a solution of 2-(4-bromo-1H-indazol-1-yl) ethan-1-ol (0.700 g, 2.904 mmol) in 1,4-dioxane (10 ml) were added bis(pinacolato)diborane (1.102 g, 4.356 mmol) and KOAc (0.569 g, 5.808 mmol) at rt. The reaction mixture was degassed for 10 min at rt before addition of PdCl$_2$(dppf) (0.212 g, 0.290 mmol). The reaction mixture was heated at 100° C. for 1 h. The resulting mixture was cooled to rt and concentrated under reduced pressure. The obtained residue was washed with n-hexane (10 ml) yielding 2-(4-(4,4,5,5-tetramethyl-1,3,2-dioxaborolan-2-yl)-1H-indazol-1-yl) ethan-1-ol (1.0 g). LCMS: Method 1, 1.880 min, MS: ES+ 289.50 [M+1]. This material was directly used for next step without further purification.

Intermediate G Tert-butyl 6-bromo-2-oxo-1,2-dihydrospiro[pyrido[2,3-b][1,4]oxazine-3,3'-pyrrolidine]-1'-carboxylate

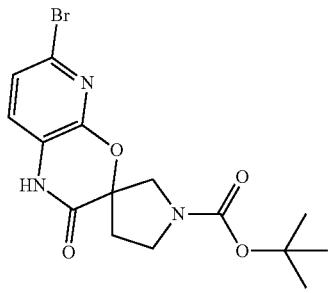 [SMILES: CC(C)(C)OC(=O)N1CCC2(C1)Oc1nc(Br)ccc1NC2=O]

This was prepared in a similar way to Intermediate D, using 2,6-dibromo-3-nitropyridine (CAS Number 55304-80-8). LCMS: Method 1, 1.892 min, MS: ES+ 384.40, 386.40, $^1$H NMR (400 MHz, DMSO-d6) δ ppm: 11.23 (br s, 1H), 7.31 (d, J=8.0 Hz, 1H), 7.23 (d, J=8.0 Hz, 1H), 3.69-3.74 (m, 1H), 3.52-3.62 (m, 3H), 2.33-2.39 (m, 1H), 2.21-2.24 (m, 1H), 1.42 (d, J=10.4 Hz, 9H).

Scheme 1

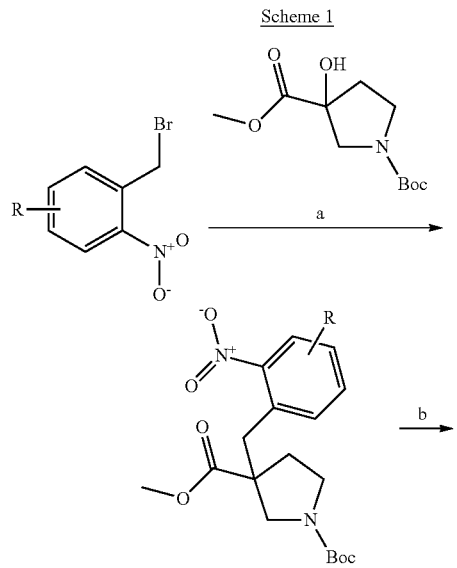

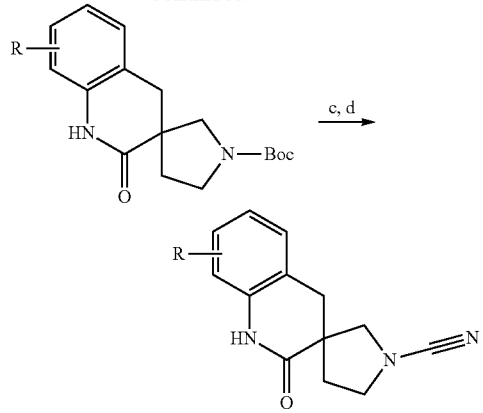

Reagents and conditions: a) i) LiHMDS, hexane, THF; b) 10% Pd/C, H$_2$, MeOH OR Fe, NH$_4$Cl, THF, water; c) TFA, DCM; d) CNBr, K$_2$CO$_3$, THF Example 1 2'-Oxo-1',4'-dihydro-2'H-spiro[pyrrolidine-3,3'-quinoline]-1-carbonitrile Synthesis According to Scheme 1

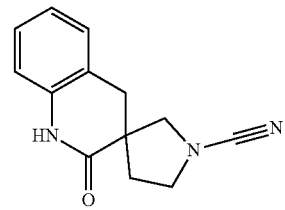 [SMILES: N#CN1CCC2(Cc3ccccc3NC2=O)C1]

Step a.

To a stirred solution of tert-butyl methyl pyrrolidine-1,3-dicarboxylate (CAS Number 122684-33-7; 1.0 g, 4.367 mmol) in dry THF (15 ml) was added 1M LiHMDS in hexane (1.08 g, 6.55 mmol) at −78° C. The reaction mixture was stirred at −78° C. for 0.5 h then 2-nitrobenzyl bromide (1.03 g, 4.803 mmol) was added at −78° C. The resulting reaction mixture was warmed to rt and stirred for 16 h. The mixture was then poured into saturated ammonium chloride solution (20 ml), diluted with water (100 ml) and extracted with EtOAc (5×50 ml). The combined organic phase was dried over Na$_2$SO$_4$, filtered and concentrated under reduced pressure. The resulting crude material was purified by flash chromatography (6% EtOAc in hexane) to afford 1-(tert-butyl) 3-methyl 3-(2-nitrobenzyl)pyrrolidine-1,3-dicarboxylate (0.48 g, 1.319 mmol). LCMS: Method 1, 2.41 min, MS: ES+ 365.4; $^1$H NMR (400 MHz, DMSO-d6) δ ppm: 7.93 (d, J=8.0 Hz, 1H), 7.68 (t, J=7.2 Hz, 1H), 7.53 (t, J=8.0 Hz, 1H), 7.36-7.41 (m, 1H), 3.57-3.64 (m, 1H), 3.34-3.42 (m, 6H), 3.11-3.20 (m, 2H), 2.15-2.19 (m, 1H), 1.88-1.93 (m, 1H), 1.39 (s, 9H).

Step b.

To a stirred solution of 1-(tert-butyl) 3-methyl 3-(2-nitrobenzyl)pyrrolidine-1,3-dicarboxylate (0.2 g, 0.549 mmol) in MeOH (10 ml) was added 10% dry Pd/C (0.2 g) at rt. The reaction mixture was purged with H$_2$ gas at rt for 0.5 h. The resulting reaction mixture was carefully filtered through celite hyflow and concentrated under reduced pressure to afford tert-butyl 2'-oxo-1',4'-dihydro-2'H-spiro[pyrrolidine-3,3'-quinoline]-1-carboxylate (0.14 g, 0.463 mmol).

LCMS: Method 1, 2.20 min, MS: ES+ 247.4 (M-56); $^1$H NMR (400 MHz, MeOD) δ ppm: 7.19-7.24 (m, 2H), 7.02 (t, J=7.2 Hz, 1H), 6.90 (d, J=8.0 Hz, 1H), 3.71-3.76 (m, 2H), 3.49-3.69 (m, 2H), 2.93-3.06 (m, 2H), 2.14-2.24 (m, 1H), 1.77-1.89 (m, 1H) 1.47 (s, 9H).

Step c.

To a stirred solution of tert-butyl 2'-oxo-1',4'-dihydro-2'H-spiro[pyrrolidine-3,3'-quinoline]-1-carboxylate (0.13 g, 0.43 mmol) in DCM (1 ml) was added TFA (1 ml) at rt. The reaction mixture was stirred at rt for 2 h. The resulting reaction mixture was concentrated under reduced pressure yielding 1',4'-dihydro-2'H-spiro[pyrrolidine-3,3'-quinolin]-2'-one TFA salt (0.09 g, 0.285 mmol). This material was used directly for the next step without further purification. LCMS: Method 1, 1.46 min, MS: ES+203.3.

Step d.

To a stirred solution of 1',4'-dihydro-2'H-spiro[pyrrolidine-3,3'-quinolin]-2'-one TFA salt (0.08 g, 0.253 mmol) in THF (10 ml) was added K$_2$CO$_3$ (0.174 g, 1.265 mmol) at rt. Cyanogen bromide (0.032 g, 0.304 mmol) was added to the reaction mixture at rt and the mixture was stirred at rt for 0.5 h. The resulting reaction mixture was filtered and excess THF was removed under reduced pressure. The resulting residue was purified by flash chromatography (30% EtOAc in hexane) yielding 2'-oxo-1',4'-dihydro-2'H-spiro[pyrrolidine-3,3'-quinoline]-1-carbonitrile (0.022 g, 0.096 mmol). LCMS: Method 2, 3.26 min, MS: ES+ 228.4; $^1$H NMR (400 MHz, DMSO-d6) δ ppm: 10.36 (s, 1H), 7.16-7.20 (m, 2H), 6.93-6.97 (m, 1H), 6.88 (d, J=7.6 Hz, 1H), 3.67 (d, J=9.6 Hz, 1H), 3.51-3.55 (m, 1H), 3.38-3.44 (m, 1H), 3.22 (d, J=9.6 Hz, 1H), 3.02 (d, J=16 Hz, 1H), 2.89 (s, J=15.6 Hz, 1H), 1.97-2.04 (m, 1H), 1.72-1.79 (m, 1H).

Compounds in Table 1 were synthesised using a procedure similar to that described for Example 1.

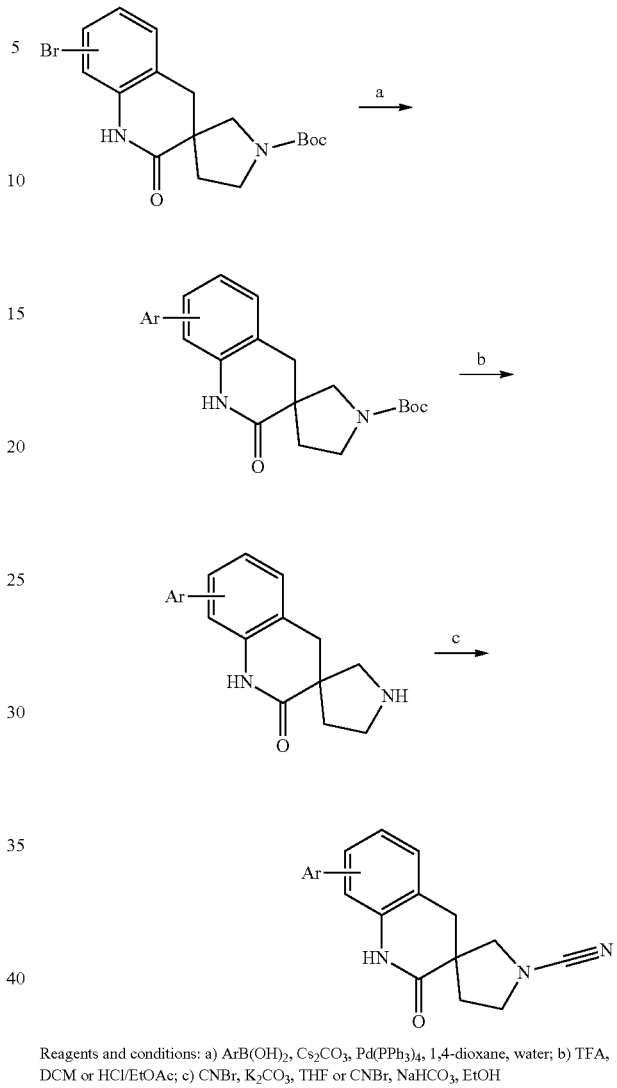

Scheme 2

Reagents and conditions: a) ArB(OH)$_2$, Cs$_2$CO$_3$, Pd(PPh$_3$)$_4$, 1,4-dioxane, water; b) TFA, DCM or HCl/EtOAc; c) CNBr, K$_2$CO$_3$, THF or CNBr, NaHCO$_3$, EtOH

TABLE 1

| Example | R— | Name | Benzyl halide CAS Number | LCMS method | LCMS RT (min) | MS ES+ | $^1$H NMR (400 MHz, DMSO-d6) δ ppm |
|---|---|---|---|---|---|---|---|
| 2 | Cl— | 7'-Chloro-2'-oxo-1',4'-dihydro-2'H-spiro[pyrrolidine-3,3'-quinoline]-1-carbonitrile | 52311-59-8 | 2 | 3.710 | 262.18 | 10.64 (s, 1 H), 7.22 (d, J = 7.2 Hz, 1 H), 6.99 (d, J = 6.8 Hz, 1 H), 6.90 (s, 1 H), 3.67 (d, J = 10.0 Hz, 1 H), 3.49-3.52 (m, 1 H), 3.39-3.42 (m, 1 H), 3.22 (d, J = 9.2 Hz, 1 H), 3.01 (d, J = 15.6 Hz, 1 H), 2.90 (d, J = 17.2 Hz, 1 H), 1.98-2.02 (m, 1 H), 1.73-1.78 (m, 1 H). |
| 3 | MeO— | 7'-Methoxy-2'-oxo-1',4'-dihydro-2'H-spiro[pyrrolidine-3,3'-quinoline]-1-carbonitrile | 57559-52-1 | 3 | 3.171 | ES-256.20 | 10.28 (s, 1 H), 7.09 (d, J = 8.4 Hz, 1 H), 6.51-6.54 (dd, J = 8.4, 2.4 Hz, 1 H), 6.46 (d, J = 2.4 Hz, 1 H), 3.69 (s, 3 H), 3.65 (d, J = 9.6 Hz, 1 H), 3.48-3.53 (m, 1 H), 3.37-3.43 (m, 1 H), 3.20 (d, J = 9.2 Hz, 1 H), 2.79-2.94 (m, 2 H), 1.96-2.03 (m, 1 H), 1.71-1.78 (m, 1 H). |

Example 4 2'-Oxo-7'-phenyl-1',4'-dihydro-2'H-spiro[pyrrolidine-3,3'-quinoline]-1-carbonitrile Synthesis According to Scheme 2

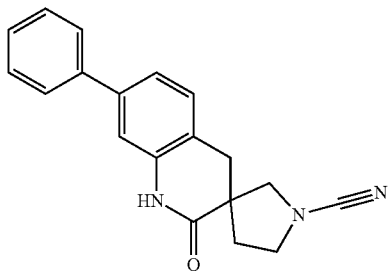 [SMILES: N#CN1CCC2(Cc3ccc(-c4ccccc4)cc3NC2=O)C1]

Step a.

To a stirred solution of tert-butyl 7'-bromo-2'-oxo-1',4'-dihydro-2'H-spiro[pyrrolidine-3,3'-quinoline]-1-carboxylate (Intermediate B; 0.25 g, 0.655 mmol) in 1,4-dioxane:water (8:2, 10 ml) was added phenylboronic acid (0.16 g, 1.311 mmol) and $Cs_2CO_3$ (0.427 g, 1.311 mmol) at rt. The reaction mixture was degassed for 20 min at rt before addition of $Pd(PPh_3)_4$ (0.075 g, 0.065 mmol). The reaction mixture was heated at 80° C. for 8 h. The resulting reaction mixture was cooled to rt, poured into water (30 ml) and extracted with EtOAc (5×25 ml). The combined organic phase was separated and washed with brine (2×20 ml). The organic phase was separated, dried over $Na_2SO_4$, filtered and concentrated under reduced pressure. The resulting residue was purified by flash chromatography (18% EtOAc in hexane) yielding tert-butyl 2'-oxo-7'-phenyl-1',4'-dihydro-2'H-spiro[pyrrolidine-3,3'-quinoline]-1-carboxylate (0.21 g, 0.552 mmol). LCMS: Method 1, 2.54 min, MS: ES+ 323.4 (M-56).

Steps b-c.

The title compound was synthesised using the above intermediate following a procedure similar to steps c-d of Example 1. LCMS: Method 2, 4.23 min, MS: ES+ 304.3; $^1$H NMR (400 MHz, DMSO-$d_6$) δ ppm 10.45 (s, 1H), 7.57-7.59 (m, 2H), 7.45-7.49 (m, 2H), 7.35-7.39 (m, 1H), 7.25-7.28 (m, 2H), 7.14 (d, J=1.6 Hz, 1H), 3.71 (d, J=9.6 Hz, 1H), 3.52-3.57 (m, 1H), 3.40-3.46 (m, 1H), 3.26 (d, J=10.0 Hz, 1H), 3.07 (d, J=16.0 Hz, 1H), 2.95 (d, J=16.0 Hz, 1H), 2.03-2.09 (m, 1H), 1.77-1.84 (m, 1H).

Example 5 7'-(5-Isopropyl-2-methoxyphenyl)-2'-oxo-1',4'-dihydro-2'H-spiro[pyrrolidine-3,3'-quinoline]-1-carbonitrile Synthesis According to Scheme 2

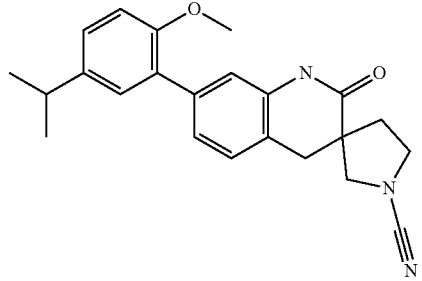 [SMILES: COc1ccc(C(C)C)cc1-c1ccc2c(c1)NC(=O)C1(CCN(C#N)C1)C2]

Step a.

To a solution of tert-butyl 7'-bromo-2'-oxo-1',4'-dihydro-2'H-spiro[pyrrolidine-3,3'-quinoline]-1-carboxylate (Intermediate B; 0.2 mmol), (5-isopropyl-2-methoxyphenyl)boronic acid (0.2 mmol) and $Cs_2CO_3$ (0.6 mmol, 3 eq) in 1,4-dioxane (1 ml) and water (0.2 ml) were added $Pd(PPh_3)_4$ (0.2 eq) at rt under nitrogen. The reaction mixture was stirred at 100° C. for 16 h. The resulting mixture was concentrated under reduced pressure. The resulting residue was purified by prep-TLC (PE/EtOAc=1:1) yielding tert-butyl 7'-(5-isopropyl-2-methoxyphenyl)-2'-oxo-2',4'-dihydro-1'H-spiro[pyrrolidine-3,3'-quinoline]-1-carboxylate.

Step b.

To a solution of tert-butyl 7'-(5-isopropyl-2-methoxyphenyl)-2'-oxo-2',4'-dihydro-1'H-spiro[pyrrolidine-3,3'-quinoline]-1-carboxylate in EtOAc (1 ml) was added HCl/EtOAc (4 M, 1 ml). The reaction mixture was stirred at rt for 2 h. The resulting mixture was concentrated under reduced pressure. The residue 7'-(5-isopropyl-2-methoxyphenyl)-1'H-spiro[pyrrolidine-3,3'-quinolin]-2'(4'H)-one was used for next step directly without further purification.

Step c.

To a solution of 7'-(5-isopropyl-2-methoxyphenyl)-1'H-spiro[pyrrolidine-3,3'-quinolin]-2'(4'H)-one in EtOH (2 ml) was added cyanogen bromide (0.2 mmol) and $NaHCO_3$ (0.6 mmol). The reaction mixture was stirred at rt for 16 h. The resulting mixture was concentrated under reduced pressure. The crude was purified by preparative reverse phase HPLC (A: 0.078% $CH_3COONH_4$ in water, B: MeCN) to get 7'-(5-isopropyl-2-methoxyphenyl)-2'-oxo-2',4'-dihydro-1 $^1$H-spiro[pyrrolidine-3,3'-quinoline]-1-carbonitrile (37.25 mg, 99.2 µmol). LCMS: Method 8, 3.353 min, MS: ES+ 376.1.

Compounds in Table 2 were synthesised using a procedure similar to that described for Example 5.

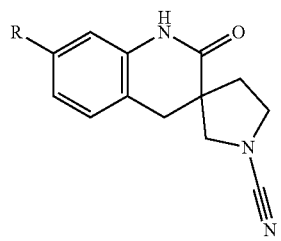

TABLE 2

| Example | R | Name | Boronic acid CAS Number | LCMS method | LCMS RT (min) | MS ES+ |
|---|---|---|---|---|---|---|
| 6 | Ph-C6H4- | 7'-([1,1'-Biphenyl]-4-yl)-2'-oxo-1',4'-dihydro-2'H-spiro[pyrrolidine-3,3'-quinoline]-1-carbonitrile | 5122-94-1 | 11 | 2.862 | 380.1 |
| 7 | PhCH2O-C6H4- | 7'-(4-(Benzyloxy)phenyl)-2'-oxo-1',4'-dihydro-2'H-spiro[pyrrolidine-3,3'-quinoline]-1-carbonitrile | 146631-00-7 | 11 | 2.835 | 410.1 |
| 8 | 2-F-5-Me-C6H3- | 7'-(2-Fluoro-5-methylphenyl)-2'-oxo-1',4'-dihydro-2'H-spiro[pyrrolidine-3,3'-quinoline]-1-carbonitrile | 166328-16-1 | 8 | 3.214 | 336.1 |
| 9 | 3-NC-C6H4- | 7'-(3-Cyanophenyl)-2'-oxo-1',4'-dihydro-2'H-spiro[pyrrolidine-3,3'-quinoline]-1-carbonitrile | 1072945-82-4 | 8 | 2.761 | 329 |
| 10 | 1-Methyl-1H-pyrazol-5-yl | 7'-(1-Methyl-1H-pyrazol-5-yl)-2'-oxo-1',4'-dihydro-2'H-spiro[pyrrolidine-3,3'-quinoline]-1-carbonitrile | 847818-74-0 | 10 | 2.59 | 308.1 |
| 11 | PhO-C6H4- | 2'-Oxo-7'-(4-phenoxyphenyl)-1',4'-dihydro-2'H-spiro[pyrrolidine-3,3'-quinoline]-1-carbonitrile | 51067-38-0 | 11 | 2.848 | 396.1 |
| 12 | 1-Methyl-1H-pyrazol-4-yl | 7'-(1-Methyl-1H-pyrazol-4-yl)-2'-oxo-1',4'-dihydro-2'H-spiro[pyrrolidine-3,3'-quinoline]-1-carbonitrile | 1022151-50-3 | 10 | 2.567 | 308.1 |
| 13 | 4-NC-C6H4- | 7'-(4-Cyanophenyl)-2'-oxo-1',4'-dihydro-2'H-spiro[pyrrolidine-3,3'-quinoline]-1-carbonitrile | 126747-14-6 | 8 | 2.974 | 329.1 |
| 14 | 2-Cl-5-(OCF3)-C6H3- | 7'-(2-Chloro-5-(trifluoromethoxy)phenyl)-2'-oxo-1',4'-dihydro-2'H-spiro[pyrrolidine-3,3'-quinoline]-1-carbonitrile | 1022922-16-2 | 11 | 3.133 | 422.1 |
| 15 | 5-(MeNHC(O))-pyridin-2-yl | 5-(1-Cyano-2'-oxo-1',4'-dihydro-2'H-spiro[pyrrolidine-3,3'-quinolin]-7'-yl)-N-methylpicolinamide | 1006876-27-2 | 10 | 2.615 | 362.1 |

TABLE 2-continued

| Example | R | Name | Boronic acid CAS Number | LCMS method | LCMS RT (min) | MS ES+ |
|---|---|---|---|---|---|---|
| 16 | 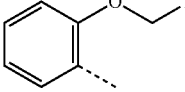 | 7'-(2-(Benzyloxy)phenyl)-2'-oxo-1',4'-dihydro-2'H-spiro[pyrrolidine-3,3'-quinoline]-1-carbonitrile | 190661-29-1 | 11 | 3.104 | 410.1 |
| 17 | 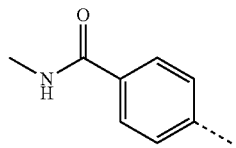 | 4-(1-Cyano-2'-oxo-1',4'-dihydro-2'H-spiro[pyrrolidine-3,3'-quinolin]-7'-yl)-N-methylbenzamide | 121177-82-0 | 8 | 2.702 | 361 |
| 18 | 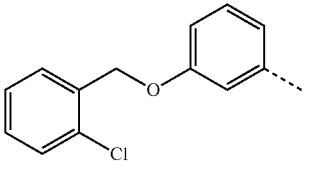 | 7'-(3-((2-Chlorobenzyl)oxy)phenyl)-2'-oxo-1',4'-dihydro-2'H-spiro[pyrrolidine-3,3'-quinoline]-1-carbonitrile | 845551-45-3 | 11 | 3.244 | 444.1 |
| 19 | 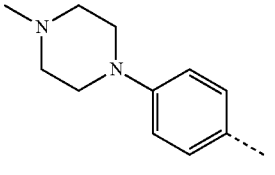 | 7'-(4-(4-Methylpiperazin-1-yl)phenyl)-2'-oxo-1',4'-dihydro-2'H-spiro[pyrrolidine-3,3'-quinoline]-1-carbonitrile | 229009-40-9 | 8 | 2.492 | 402.2 |
| 20 | 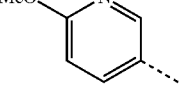 | 7'-(6-Methoxypyridin-3-yl)-2'-oxo-1',4'-dihydro-2'H-spiro[pyrrolidine-3,3'-quinoline]-1-carbonitrile | 13472-61-2 | 8 | 2.875 | 335.1 |
| 21 | 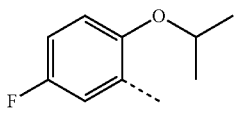 | 7'-(5-Fluoro-2-isopropoxyphenyl)-2'-oxo-1',4'-dihydro-2'H-spiro[pyrrolidine-3,3'-quinoline]-1-carbonitrile | 480438-63-9 | 8 | 3.271 | 380.1 |
| 22 | 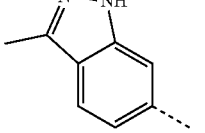 | 7'-(3-Methyl-1H-indazol-6-yl)-2'-oxo-1',4'-dihydro-2'H-spiro[pyrrolidine-3,3'-quinoline]-1-carbonitrile | 1245816-26-5 | 8 | 2.853 | 358.1 |
| 23 | 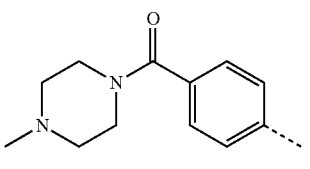 | 7'-(4-(4-Methylpiperazine-1-carbonyl)phenyl)-2'-oxo-1',4'-dihydro-2'H-spiro[pyrrolidine-3,3'-quinoline]-1-carbonitrile | 832114-06-4 | 8 | 2.148 | 430 |
| 24 | 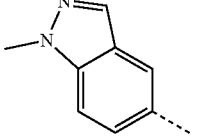 | 7'-(1-Methyl-1H-indazol-5-yl)-2'-oxo-1',4'-dihydro-2'H-spiro[pyrrolidine-3,3'-quinoline]-1-carbonitrile | 590418-08-9 | 8 | 2.688 | 358 |
| 25 | 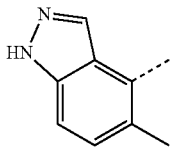 | 7'-(5-Methyl-1H-indazol-4-yl)-2'-oxo-1',4'-dihydro-2'H-spiro[pyrrolidine-3,3'-quinoline]-1-carbonitrile | 1245816-10-7 | 8 | 2.87 | 358.1 |

TABLE 2-continued

| Example | R | Name | Boronic acid CAS Number | LCMS method | LCMS RT (min) | MS ES+ |
|---|---|---|---|---|---|---|
| 26 | 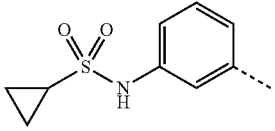 | N-(3-(1-Cyano-2'-oxo-1',4'-dihydro-2'H-spiro[pyrrolidine-3,3'-quinolin]-7'-yl)phenyl)cyclopropane-sulfonamide | 1072945-67-5 | 8 | 2.486 | 423 |
| 27 | 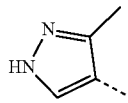 | 7'-(3-Methyl-1H-pyrazol-4-yl)-2'-oxo-1',4'-dihydro-2'H-spiro[pyrrolidine-3,3'-quinoline]-1-carbonitrile | 936250-20-3 | 10 | 2.045 | 308 |
| 28 | 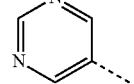 | 2'-Oxo-7'-(pyrimidin-5-yl)-1',4'-dihydro-2'H-spiro[pyrrolidine-3,3'-quinoline]-1-carbonitrile | 109299-78-7 | 10 | 1.921 | 306 |
| 29 | 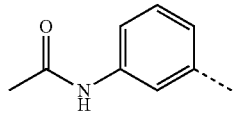 | N-(3-(1-Cyano-2'-oxo-1',4'-dihydro-2'H-spiro[pyrrolidine-3,3'-quinolin]-7'-yl)phenyl)acetamide | 521069-03-4 | 8 | 2.278 | 361 |
| 30 | 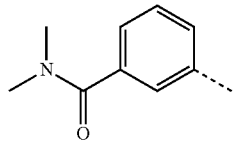 | 3-(1-Cyano-2'-oxo-1',4'-dihydro-2'H-spiro[pyrrolidine-3,3'-quinolin]-7'-yl)-N,N-dimethylbenzamide | 373384-14-6 | 10 | 2.291 | 375 |
| 31 | 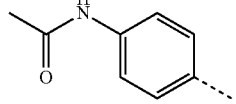 | N-(4-(1-Cyano-2'-oxo-1',4'-dihydro-2'H-spiro[pyrrolidine-3,3'-quinolin]-7'-yl)phenyl)acetamide | 101251-09-6 | 8 | 2.459 | 361 |
| 32 | 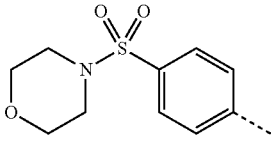 | 7'-(4-(Morpholinosulfonyl)phenyl)-2'-oxo-1',4'-dihydro-2'H-spiro[pyrrolidine-3,3'-quinoline]-1-carbonitrile | 486422-68-8 | 8 | 2.701 | 453 |
| 33 | 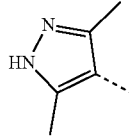 | 7'-(3,5-Dimethyl-1H-pyrazol-4-yl)-2'-oxo-1',4'-dihydro-2'H-spiro[pyrrolidine-3,3'-quinoline]-1-carbonitrile | 857530-80-4 | 10 | 2.57 | 322.1 |
| 34 | 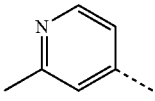 | 7'-(2-Methylpyridin-4-yl)-2'-oxo-1',4'-dihydro-2'H-spiro[pyrrolidine-3,3'-quinoline]-1-carbonitrile | 579476-63-4 | 8 | 2.321 | 319.1 |
| 35 | 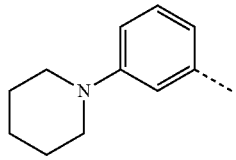 | 2'-Oxo-7'-(3-(piperidin-1-yl)phenyl)-1',4'-dihydro-2'H-spiro[pyrrolidine-3,3'-quinoline]-1-carbonitrile | 852227-97-5 | 11 | 1.828 | 387.1 |
| 36 | 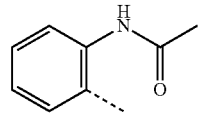 | N-(2-(1-Cyano-2'-oxo-1',4'-dihydro-2'H-spiro[pyrrolidine-3,3'-quinolin]-7'-yl)phenyl)acetamide | 169760-16-1 | 8 | 2.292 | 361.1 |

TABLE 2-continued

| Example | R | Name | Boronic acid CAS Number | LCMS method | LCMS RT (min) | MS ES+ |
|---|---|---|---|---|---|---|
| 37 | | 7'-(4-(Morpholine-4-carbonyl)phenyl)-2'-oxo-1',4'-dihydro-2'H-spiro[pyrrolidine-3,3'-quinoline]-1-carbonitrile | 656239-38-2 | 8 | 2.304 | 417.1 |
| 38 | | 7'-(3-(Morpholinosulfonyl)phenyl)-2'-oxo-1',4'-dihydro-2'H-spiro[pyrrolidine-3,3'-quinoline]-1-carbonitrile | 871329-60-1 | 8 | 2.952 | 453.1 |
| 39 | | 7'-(1-Methyl-6-oxo-1,6-dihydropyridin-3-yl)-2'-oxo-1',4'-dihydro-2'H-spiro[pyrrolidine-3,3'-quinoline]-1-carbonitrile | 1002309-52-5 | 10 | 1.852 | 335.1 |
| 40 | | 7'-(2-Methylbenzo[d]thiazol-5-yl)-2'-oxo-1',4'-dihydro-2'H-spiro[pyrrolidine-3,3'-quinoline]-1-carbonitrile | 590417-67-7 | 8 | 2.677 | 375.1 |
| 88 | | 2'-Oxo-7'-(3-(trifluoromethoxy)phenyl)-1',4'-dihydro-2'H-spiro[pyrrolidine-3,3'-quinoline]-1-carbonitrile | 179113-90-7 | 11 | 3.222 | 388.0 |
| 89 | | 4-(1-Cyano-2'-oxo-1',4'-dihydro-2'H-spiro[pyrrolidine-3,3'-quinolin]-7'-yl)-N,N-dimethylbenzamide | 405520-68-5 | 10 | 2.813 | 375.2 |
| 90 | | 7'-(3-(4-Methylpiperazine-1-carbonyl)phenyl)-2'-oxo-1',4'-dihydro-2'H-spiro[pyrrolidine-3,3'-quinoline]-1-carbonitrile | 957060-92-3 | 8 | 2.842 | 430.3 |
| 91 | | 7'-(1-Methyl-1H-pyrrol-2-yl)-2'-oxo-1',4'-dihydro-2'H-spiro[pyrrolidine-3,3'-quinoline]-1-carbonitrile | 911318-81-5 | 8 | 2.907 | 307.0 |

Compounds in Tables 3.1 and 3.2 were synthesised using a procedure similar to that described for Intermediate B/Example 4 using 4-bromo-2-(bromomethyl)-1-nitrobenzene.

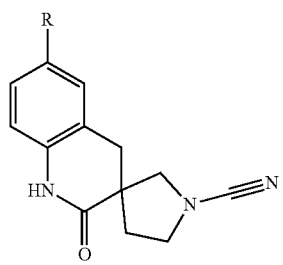

TABLE 3.1

| Example | R | Name | Boronic acid CAS Number | LCMS method | LCMS RT (min) | MS ES+ | ¹H NMR (400 MHz, DMSO-d6) δ ppm |
|---|---|---|---|---|---|---|---|
| 41 | Ph— | 2'-Oxo-6'-phenyl-1',4'-dehydro-2'H-spiro[pyrrolidine-3,3'-quinoline]-1-carbonitrile | 98-80-6 | 3 | 4.39 | 304.1 | 10.45 (s, 1 H), 7.62-7.64 (m, 2 H), 7.49-7.52 (m, 2 H), 7.42-7.46 (m, 2 H), 7.30-7.34 (m, 1 H), 6.99 (d, J = 8.4 Hz, 1 H), 3.69-3.71 (m, 1 H), 3.48-3.57 (m, 1 H), 3.42-3.46 (m, 1 H), 3.25-3.29 (m, 1 H), 3.10 (d, J = 16.0 Hz, 1 H), 2.98 (d, J = 16.0 Hz, 1 H), 2.02-2.07 (m, 1 H), 1.77-1.84 (m, 1 H). |
| 42 | 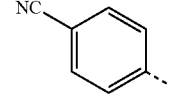 | 6'-(4-Cyanophenyl)-2'-oxo-1',4'-dihydro-2'H-spiro[pyrrolidine-3,3'-quinoline]-1-carbonitrile | 126747-14-6 | 2 | 3.97 | 329.24 | 10.54 (s, 1 H), 7.84-7.91 (m, 4 H), 7.61-7.65 (m, 2 H), 7.00 (d, J = 8.4 Hz, 1 H), 3.71 (d, J = 10.0 Hz, 1 H), 3.51-3.54 (m, 1H), 3.40-3.46 (m, 1 H), 3.27 (d, J = 9.6 Hz, 1H), 3.11 (d, J = 16 Hz, 1 H), 3.00 (d, J = 16 Hz, 1 H), 2.01-2.07 (m, 1 H), 1.77-1.84 (m, 1H). |
| 43 | 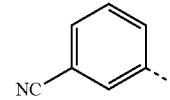 | 6'-(3-Cyanophenyl)-2'-oxo-1',4'-dihydro-2'H-spiro[pyrrolidine-3,3'-quinoline]-1-carbonitrile | 150255-96-2 | 2 | 3.95 | 329.24 | 10.51 (s, 1 H), 8.12 (s, 1 H), 7.99 (d, J = 7.6 Hz, 1 H), 7.78 (d, J = 7.2 Hz, 1 H), 7.59-7.65 (m, 3 H), 6.99 (d, J = 8.0 Hz, 1 H), 3.71 (d, J = 10.0 Hz, 1 H), 3.53-3.57 (m, 1 H), 3.40-3.46 (m, 1 H), 3.28 (m, 1 H), 3.10 (d, J = 16.4 Hz, 1 H), 3.00 (d, J = 16.4 Hz, 1 H), 2.01-2.08 (m, 1 H), 1.77-1.82 (m, 1 H). |
| 44 | 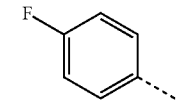 | 6'-(4-Fluorophenyl)-2'-oxo-1',4'-dihydro-2'H-spiro[pyrrolidine-3,3'-quinoline]-1-carbonitrile | 1765-93-1 | 2 | 4.03 | 322.24 | 10.45 (s, 1 H), 7.64-7.68 (m, 2 H), 7.47-7.51 (m, 2 H), 7.27 (t, J = 8.8 Hz, 2 H), 6.96 (d, J = 8 Hz, 1 H), 3.70 (d, J = 9.6 Hz, 1 H), 3.51-3.56 (m, 1 H), 3.41-3.46 (m, 1 H), 3.26 (d, J = 9.6 Hz, 1 H), 3.09 (d, J = 15.6 Hz, 1 H), 2.97 (d, J = 16.0 Hz, 1 H), 1.99-2.07 (m, 1 H), 1.76-1.81 (m, 1 H). |
| 45 | 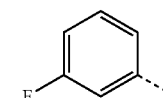 | 6'-(3-Fluorophenyl)-2'-oxo-1',4'-dihydro-2'H-spiro[pyrrolidine-3,3'-quinoline]-1-carbonitrile | 768-35-4 | 2 | 4.04 | 322.34 | 10.49 (s, 1 H), 7.54-7.58 (m, 2 H), 7.44-7.49 (m, 3 H), 7.13-7.17 (m, 1 H), 6.97 (d, J = 8.4 Hz, 1 H), 3.71 (d, J = 8 Hz, 1 H), 3.51-3.57 (m, 1 H), 3.40-3.46 (m, 1 H), 3.27 (d, J = 9.6 Hz, 1 H), 3.10 (d, J = 16 Hz, 1 H), 2.98 (d, J = 16 Hz, 1 H), 1.99-2.07 (m, 1H), 1.76-1.83 (m, 1 H). |

TABLE 3.2

| Example | R | Name | LCMS method | LCMS RT (min) | MS ES+ |
|---|---|---|---|---|---|
| 92 | 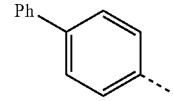 | 6'-([1,1'-Biphenyl]-4-yl)-2'-oxo-1',4'-dihydro-2'H-spiro[pyrrolidine-3,3'-quinoline]-1-carbonitrile | 11 | 3.029 | 380.1 |
| 93 | 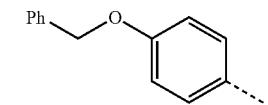 | 6'-(4-(Benzyloxy)phenyl)-2'-oxo-1',4'-dihydro-2'H-spiro[pyrrolidine-3,3'-quinoline]-1-carbonitrile | 10 | 3.243 | 410.1 |
| 94 | 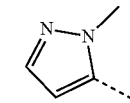 | 6'-(1-Methyl-1H-pyrazol-5-yl)-2'-oxo-1',4'-dihydro-2'H-spiro[pyrrolidine-3,3'-quinoline]-1-carbonitrile | 10 | 1.827 | 308.1 |
| 95 | 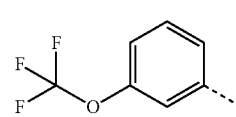 | 2'-Oxo-6'-(3-(trifluoromethoxy)phenyl)-1',4'-dihydro-2'H-spiro[pyrrolidine-3,3'-quinoline]-1-carbonitrile | 10 | 3.172 | 388.1 |

TABLE 3.2-continued

| Example | R | Name | LCMS method | LCMS RT (min) | MS ES+ |
|---|---|---|---|---|---|
| 96 | 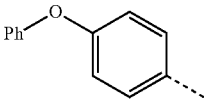 | 2'-Oxo-6'-(4-phenoxyphenyl)-1',4'-dihydro-2'H-spiro[pyrrolidine-3,3'-quinoline]-1-carbonitrile | 8 | 3.428 | 396.1 |
| 97 | 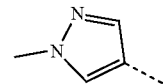 | 6'-(1-Methyl-1H-pyrazol-4-yl)-2'-oxo-1',4'-dihydro-2'H-spiro[pyrrolidine-3,3'-quinoline]-1-carbonitrile | 10 | 1.768 | 308.1 |
| 98 | 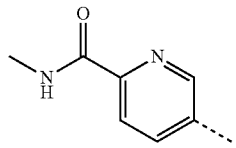 | 5-(1-Cyano-2'-oxo-1',4'-dihydro-2'H-spiro[pyrrolidine-3,3'-quinolin]-6'-yl)-N-methylpicolinamide | 10 | 1.857 | 362.1 |
| 99 | 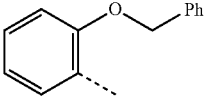 | 6'-(2-(Benzyloxy)phenyl)-2'-oxo-1',4'-dihydro-2'H-spiro[pyrrolidine-3,3'-quinoline]-1-carbonitrile | 10 | 3.197 | 410.1 |
| 100 | 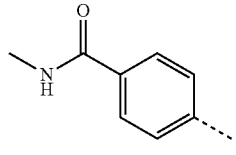 | 4-(1-Cyano-2'-oxo-1',4'-dihydro-2'H-spiro[pyrrolidine-3,3'-quinolin]-6'-yl)-N-methylbenzamide | 8 | 2.306 | 361.2 |
| 101 | 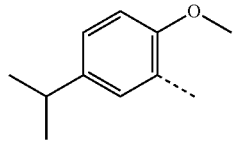 | 6'-(5-Isopropyl-2-methoxyphenyl)-2'-oxo-1',4'-dihydro-2'H-spiro[pyrrolidine-3,3'-quinoline]-1-carbonitrile | 8 | 3.302 | 376.2 |
| 102 | 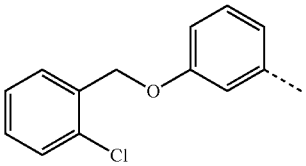 | 6'-(3-((2-Chlorobenzyl)oxy)phenyl)-2'-oxo-1',4'-dihydro-2'H-spiro[pyrrolidine-3,3'-quinoline]-1-carbonitrile | 11 | 3.134 | 444.1 |
| 103 | 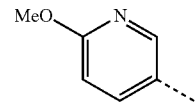 | 6'-(6-Methoxypyridin-3-yl)-2'-oxo-1',4'-dihydro-2'H-spiro[pyrrolidine-3,3'-quinoline]-1-carbonitrile | 8 | 2.570 | 335.1 |
| 104 | 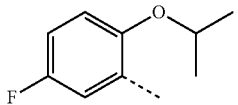 | 6'-(5-Fluoro-2-isopropoxyphenyl)-2'-oxo-1',4'-dihydro-2'H-spiro[pyrrolidine-3,3'-quinoline]-1-carbonitrile | 8 | 3.185 | 380.2 |
| 105 | 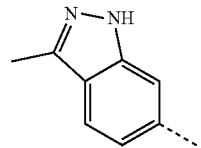 | 6'-(3-Methyl-1H-indazol-6-yl)-2'-oxo-1',4'-dihydro-2'H-spiro[pyrrolidine-3,3'-quinoline]-1-carbonitrile | 8 | 2.564 | 358.2 |
| 106 | 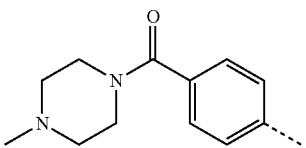 | 6'-(4-(4-Methylpiperazine-1-carbonyl)phenyl)-2'-oxo-1',4'-dihydro-2'H-spiro[pyrrolidine-3,3'-quinoline]-1-carbonitrile | 8 | 2.032 | 430.2 |

TABLE 3.2-continued

| Example | R | Name | LCMS method | LCMS RT (min) | MS ES+ |
|---|---|---|---|---|---|
| 107 | 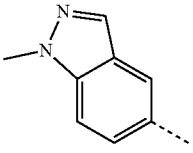 | 6'-(1-Methyl-1H-indazol-5-yl)-2'-oxo-1',4'-dihydro-2'H-spiro[pyrrolidine-3,3'-quinoline]-1-carbonitrile | 8 | 2.551 | 358.2 |
| 108 | 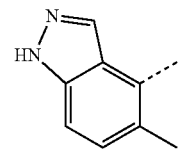 | 6'-(5-Methyl-1H-indazol-4-yl)-2'-oxo-1',4'-dihydro-2'H-spiro[pyrrolidine-3,3'-quinoline]-1-carbonitrile | 8 | 2.586 | 358.2 |
| 109 | 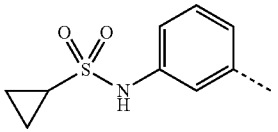 | N-(3-(1-Cyano-2'-oxo-1',4'-dihydro-2'H-spiro[pyrrolidine-3,3'-quinolin]-6'-yl)phenyl)cyclopropanesulfonamide | 8 | 2.651 | 423.1 |
| 110 | 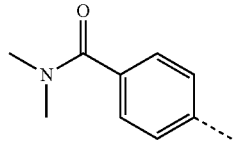 | 4-(1-Cyano-2'-oxo-1',4'-dihydro-2'H-spiro[pyrrolidine-3,3'-quinolin]-6'-yl)-N,N-dimethylbenzamide | 10 | 1.976 | 375.1 |
| 111 | 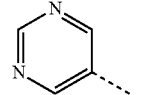 | 2'-Oxo-6'-(pyrimidin-5-yl)-1',4'-dihydro-2'H-spiro[pyrrolidine-3,3'-quinoline]-1-carbonitrile | 10 | 1.573 | 306.1 |
| 112 | 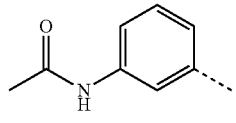 | N-(3-(1-Cyano-2'-oxo-1',4'-dihydro-2'H-spiro[pyrrolidine-3,3'-quinolin]-6'-yl)phenyl)acetamide | 8 | 2.382 | 361.1 |
| 113 | 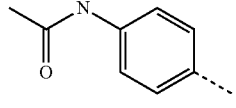 | N-(4-(1-Cyano-2'-oxo-1',4'-dihydro-2'H-spiro[pyrrolidine-3,3'-quinolin]-6'-yl)phenyl)acetamide | 8 | 2.315 | 361.2 |
| 114 | 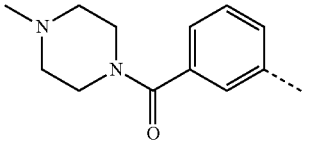 | 6'-(3-(4-Methylpiperazine-1-carbonyl)phenyl)-2'-oxo-1',4'-dihydro-2'H-spiro[pyrrolidine-3,3'-quinoline]-1-carbonitrile | 8 | 2.049 | 430.2 |
| 115 | 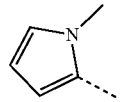 | 6'-(1-Methyl-1H-pyrrol-2-yl)-2'-oxo-1',4'-dihydro-2'H-spiro[pyrrolidine-3,3'-quinoline]-1-carbonitrile | 8 | 2.671 | 307.1 |
| 116 | 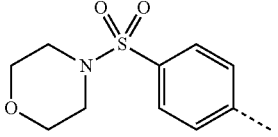 | 6'-(4-(Morpholinosulfonyl)phenyl)-2'-oxo-1',4'-dihydro-2'H-spiro[pyrrolidine-3,3'-quinoline]-1-carbonitrile | 8 | 2.612 | 453.1 |

TABLE 3.2-continued

| Example | R | Name | LCMS method | LCMS RT (min) | MS ES+ |
|---|---|---|---|---|---|
| 117 | 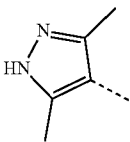 | 6'-(3,5-Dimethyl-1H-pyrazol-4-yl)-2'-oxo-1',4'-dihydro-2'H-spiro[pyrrolidine-3,3'-quinoline]-1-carbonitrile | 10 | 1.660 | 322.1 |
| 118 | 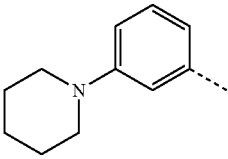 | 2'-Oxo-6'-(3-(piperidin-1-yl)phenyl)-1',4'-dihydro-2'H-spiro[pyrrolidine-3,3'-quinoline]-1-carbonitrile | 11 | 1.886 | 387.2 |
| 119 | 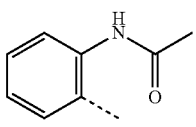 | N-(2-(1-Cyano-2'-oxo-1',4'-dihydro-2'H-spiro[pyrrolidine-3,3'-quinolin]-6'-yl)phenyl)acetamide | 10 | 1.874 | 361.1 |
| 120 | 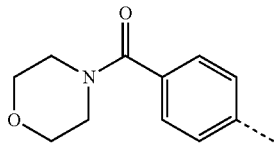 | 6'-(4-(Morpholine-4-carbonyl)phenyl)-2'-oxo-1',4'-dihydro-2'H-spiro[pyrrolidine-3,3'-quinoline]-1-carbonitrile | 8 | 2.347 | 417.2 |
| 121 | 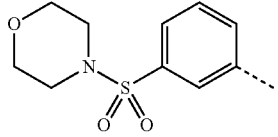 | 6'-(3-(Morpholinosulfonyl)phenyl)-2'-oxo-1',4'-dihydro-2'H-spiro[pyrrolidine-3,3'-quinoline]-1-carbonitrile | 10 | 2.207 | 470.2 |
| 122 | 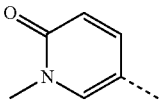 | 6'-(1-Methyl-6-oxo-1,6-dihydropyridin-3-yl)-2'-oxo-1',4'-dihydro-2'H-spiro[pyrrolidine-3,3'-quinoline]-1-carbonitrile | 10 | 1.538 | 335.1 |
| 123 | 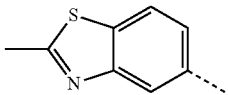 | 6'-(2-Methylbenzo[d]thiazol-5-yl)-2'-oxo-1',4'-dihydro-2'H-spiro[pyrrolidine-3,3'-quinoline]-1-carbonitrile | 8 | 2.750 | 375.1 |
| 124 | 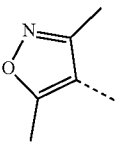 | 6'-(3,5-Dimethylisoxazol-4-yl)-2'-oxo-1',4'-dihydro-2'H-spiro[pyrrolidine-3,3'-quinoline]-1-carbonitrile | 10 | 2.324 | 323.2 |
| 125 | 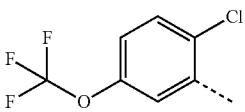 | 6'-(2-Chloro-5-(trifluoromethoxy)phenyl)-2'-oxo-1',4'-dihydro-2'H-spiro[pyrrolidine-3,3'-quinoline]-1-carbonitrile | 10 | 3.215 | 422.1 |
| 126 | 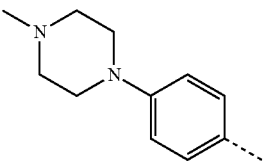 | 6'-(4-(4-Methylpiperazin-1-yl)phenyl)-2'-oxo-1',4'-dihydro-2'H-spiro[pyrrolidine-3,3'-quinoline]-1-carbonitrile | 8 | 1.966 | 402.3 |

TABLE 3.2-continued

| Example | R | Name | LCMS method | LCMS RT (min) | MS ES+ |
|---|---|---|---|---|---|
| 127 | *N-Benzyl amide structure* | N-Benzyl-4-(1-cyano-2'-oxo-1',4'-dihydro-2'H-spiro[pyrrolidine-3,3'-quinolin]-6'-yl)benzamide | 10 | 2.769 | 437.2 |
| 128 | *3-Methylpyrazole* | 6'-(3-Methyl-1H-pyrazol-4-yl)-2'-oxo-1',4'-dihydro-2'H-spiro[pyrrolidine-3,3'-quinoline]-1-carbonitrile | 10 | 1.984 | 308.2 |
| 129 | *Morpholinomethylphenyl* | 6'-(4-(Morpholinomethyl)phenyl)-2'-oxo-1',4'-dihydro-2'H-spiro[pyrrolidine-3,3'-quinoline]-1-carbonitrile | 8 | 1.906 | 403.3 |
| 130 | *N,N-dimethylbenzamide* | 3-(1-Cyano-2'-oxo-1',4'-dihydro-2'H-spiro[pyrrolidine-3,3'-quinolin]-6'-yl)-N,N-dimethylbenzamide | 10 | 2.275 | 375.1 |
| 131 | *2-Methylpyridin-4-yl* | 6'-(2-Methylpyridin-4-yl)-2'-oxo-1',4'-dihydro-2'H-spiro[pyrrolidine-3,3'-quinoline]-1-carbonitrile | 8 | 1.706 | 319.2 |

Example 46 1-Cyano-N,N-dimethyl-2'-oxo-1',4'-dihydro-2'H-spiro[pyrrolidine-3,3'-quinoline]-7'-carboxamide

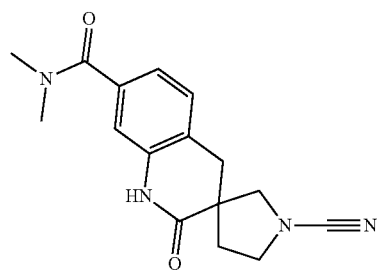 [SMILES: CN(C)C(=O)c1ccc2c(c1)NC(=O)C1(CCN(C#N)C1)C2]

Step a.

To a stirred solution of tert-butyl 7'-bromo-2'-oxo-1',4'-dihydro-2'H-spiro[pyrrolidine-3,3'-quinoline]-1-carboxylate (Intermediate B; 0.75 g, 1.967 mmol) in MeOH (20 ml) were added sodium acetate (0.81 g, 9.837 mmol) and PdCl$_2$(dppf) DCM complex (0.32 g) at rt in an autoclave. The reaction mixture was heated at 120° C. under 30 kg carbon monoxide pressure for 4 days. The reaction mixture was cool to rt, filtered through celite hyflow and washed with MeOH (5×30 ml). The filtrate was concentrated under vacuum and the resulting residue was purified by flash chromatography (38% EtOAc in hexane) yielding 1-(tert-butyl) 7'-methyl 2'-oxo-1',4'-dihydro-2'H-spiro[pyrrolidine-3,3'-quinoline]-1,7'-dicarboxylate (0.37 g, 1.025 mmol). LCMS: Method 1, 2.159 min, MS: ES+ 305.08 (M-56); $^1$H NMR (400 MHz, DMSO-d$_6$) 10.44 (s, 1H), 7.50-7.56 (m, 2H), 7.34 (d, J=8.0 Hz, 1H), 3.83 (s, 3H), 3.57 (t, J=9.6 Hz, 1H), 3.35-3.36 (m, 2H), 2.96-3.11 (m, 3H), 1.91-2.01 (m, 1H), 1.68-1.74 (m, 1H), 1.39 (d, J=4.8 Hz, 9H).

Step b.

To a stirred solution of 1-(tert-butyl) 7'-methyl 2'-oxo-1',4'-dihydro-2'H-spiro[pyrrolidine-3,3'-quinoline]-1,7'-dicarboxylate (0.35 g, 0.969 mmol) in THF:water (1:1; 20 ml) was added NaOH (0.077 g, 1.939 mmol) at rt. The reaction mixture was stirred at rt for 16 h. The resulting reaction mixture was acidified with dilute HCl (30 ml) and extracted with EtOAc (10×50 ml). The combined organic phase was separated, dried over Na$_2$SO$_4$, filtered and concentrated under reduced pressure yielding 1-(tert-butoxycarbonyl)-2'-oxo-1',4'-dihydro-2'H-spiro[pyrrolidine-3,3'-quinoline]-7'-carboxylic acid (0.26 g, 0.749 mmol). LCMS: Method 1, 1.929 min, MS: ES+ 291.1 (M-56); H NMR (400 MHz, DMSO-d$_6$) δ ppm 12.92 (br s, 1H), 10.43 (s, 1H), 7.48-7.57 (m, 2H), 7.30 (d, J=8.0 Hz, 1H), 3.54-3.59 (m, 1H), 3.22-3.34 (m, 2H), 2.95-3.10 (m, 3H), 1.99-2.01 (m, 1H), 1.68-1.73 (m, 1H), 1.38 (d, J=4.4 Hz, 9H).

Step c.

To a stirred solution of 1-(tert-butoxycarbonyl)-2'-oxo-1',4'-dihydro-2'H-spiro[pyrrolidine-3,3'-quinoline]-7'-carboxylic acid (0.25 g, 0.72 mmol) in THF (10 ml) were added HATU (0.41 g, 1.08 mmol) and DIPEA (0.185 g, 1.44 mmol) at 0° C. The reaction mixture was stirred at 0° C. for 25 min. A solution of dimethylamine (2M in THF; 0.72 ml, 1.44 mmol) was added to the reaction mixture at rt. The reaction mixture was stirred at rt for 16 h. The resulting reaction mixture was poured into water (50 ml) and extracted with EtOAc (5×50 ml). The combined organic phase was separated and washed with saturated NaHCO$_3$ solution (25 ml). The organic phase was separated, dried over Na$_2$SO$_4$, filtered and concentrated under reduced pressure. The residue was purified by flash chromatography (80% EtOAc in hexane) yielding tert-butyl 7'-(dimethylcarbamoyl)-2'-oxo-1',4'-dihydro-2'H-spiro-[pyrrolidine-3,3'-quinoline]-1-carboxylate (0.26 g, 0.696 mmol). LCMS: Method 1, 1.909 min, MS: ES+ 318.18 (M-56); H NMR (400 MHz, DMSO-$d_6$) δ ppm 10.36 (s, 1H), 7.23 (d, J=7.6 Hz, 1H), 6.95-6.97 (m, 1H), 6.87 (d, J=1.2 Hz, 1H), 3.54-3.60 (m, 1H), 3.36-3.69 (m, 1H), 3.21-3.28 (m, 1H), 3.07-3.11 (m, 1H), 2.88-3.03 (m, 8H), 1.96-2.06 (m, 1H), 1.67-1.75 (m, 1H), 1.39 (s, 9H).

Step d.

To a stirred solution of tert-butyl 7'-(dimethylcarbamoyl)-2'-oxo-1',4'-dihydro-2'H-spiro[pyrrolidine-3,3'-quinoline]-1-carboxylate (0.25 g, 0.669 mmol) in THF (3 ml) was added TFA (0.25 ml) dropwise at rt. The reaction mixture was stirred at rt for 1 h. The resulting reaction mixture was concentrated under vacuum. The resulting crude material was washed with hexane and dried under vacuum yielding N,N-dimethyl-2'-oxo-1',4'-dihydro-2'H-spiro[pyrrolidine-3,3'-quinoline]-7'-carboxamide TFA salt (0.21 g, 0.542 mmol). LCMS: Method 1, 1.289 min, MS: ES+ 274.21; $^1$H NMR (400 MHz, DMSO-$d_6$) δ ppm 10.6 (s, 1H), 9.04 (s, 1H), 8.99 (s, 1H), 7.25 (d, J=7.6 Hz, 1H), 6.99 (d, 1.2 Hz, 1H), 6.91 (s, 1H), 3.66 (t, J=4.8 Hz, 1H), 3.32-3.41 (m, 1H), 3.16 (t, J=7.6 Hz, 2H), 3.00-3.06 (m, 1H), 2.91-2.97 (m, 6H), 2.01-2.07 (m, 1H), 1.82-1.87 (m, 1H).

Step e.

To a stirred solution of N,N-dimethyl-2'-oxo-1',4'-dihydro-2'H-spiro[pyrrolidine-3,3'-quinoline]-7'-carboxamide TFA salt (0.2 g, 0.516 mmol) in THF (12 ml) were added $K_2CO_3$ (0.356 g, 2.584 mmol) at 0° C. The reaction mixture was stirred at rt for 2 h. The resulting reaction mixture was filtered, washed with THF (30 ml) and the filtrate was concentrated under vacuum. The resulting residue was purified by flash chromatography (column was packed in hexane; the gradient of EtOAc was gradually increased to 100%) yielding 1-cyano-N,N-dimethyl-2'-oxo-1',4'-dihydro-2'H-spiro[pyrrolidine-3,3'-quinoline]-7'-carboxamide (0.13 g, 0.435 mmol). LCMS: Method 2, 2.833 min, MS: ES+ 299.21; $^1$H NMR (400 MHz, DMSO-$d_6$) δ ppm 10.46 (s, 1H), 7.24 (d, J=7.6 Hz, 1H), 6.97 (dd, J=1.6 Hz, 7.6 Hz, 1H), 6.89 (s, 1H), 3.69 (d, J=9.6 Hz, 1H), 3.51-3.56 (m, 1H), 3.39-3.45 (m, 2H), 3.24 (d, J=9.6 Hz, 1H), 3.05 (d, J=16.0 Hz, 1H), 2.91-2.97 (m, 6H), 2.00-2.07 (m, 1H), 1.74-1.81 (m, 1H).

Example 47 1-Cyano-N-methyl-2'-oxo-1',4'-dihydro-2'H-spiro[pyrrolidine-3,3'-quinoline]-7'-carboxamide

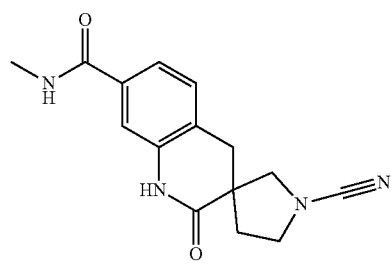 [SMILES: CNC(=O)c1ccc2c(c1)NC(=O)C1(CCN(C#N)C1)C2]

Steps a-e.

The title compound was synthesised following a procedure similar to Example 46 using methylamine (2M in THF) in step c. LCMS: Method 2 RT 2.493 min, MS: ES+ 285.27; $^1$H NMR (400 MHz, DMSO-d6) δ ppm: 10.47 (s, 1H), 8.35 (d, J=4.8 Hz, 1H), 7.35-7.39 (m, 2H), 7.26 (d, J=8 Hz, 1H), 3.68 (d, J=9.6 Hz, 1H), 3.49-3.55 (m, 1H), 3.38-3.44 (m, 1H), 3.22 (d, J=9.6 Hz, 1 H), 3.06 (d, J=16.0 Hz, 1H), 2.95 (d, J=16.4 Hz, 1H), 2.75 (d, J=4.4 Hz, 3H), 1.97-2.03 (m, 1H), 1.74-1.78 (m, 1H).

Example 132 (R)-7'-(5-Methyl-H-indazol-4-yl)-2'-oxo-1',4'-dihydro-2'H-spiro[pyrrolidine-3,3'-quinoline]-1-carbonitrile

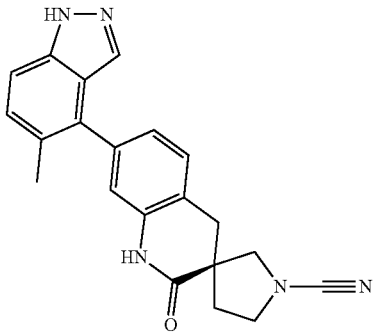 [SMILES: Cc1ccc2[nH]ncc2c1-c1ccc2c(c1)NC(=O)[C@@]1(CCN(C#N)C1)C2]

Step a.

To a solution of 4-bromo-2-nitrobenzaldehyde (CAS Number 5551-12-2; 10.000 g, 43.478 mmol) in MeOH (120 ml) were added isopropylidene malonate (CAS Number 2033-24-1; 6.260 g, 43.478 mmol), diethyl 1,4-dihydro-2,6-dimethyl-3,5-pyridinedicarboxylate (CAS Number 1149-23-1; 11.000 g, 43.478 mmol) and L-Proline (CAS Number 147-85-3; 0.99 g, 8.690 mmol) at rt. The reaction mixture was stirred at rt for 16 h. The resulting reaction mixture was concentrated under reduced pressure. The obtained residue was purified by flash chromatography (15% EtOAc in n-hexane) yielding 5-(4-bromo-2-nitrobenzyl)-2,2-dimethyl-1,3-dioxane-4,6-dione (14.500 g, 40.503 mmol). LCMS: Method 1, 3.269 min, MS: ES+ 358.0, 359.0

Step b.

To a solution of 5-(4-bromo-2-nitrobenzyl)-2,2-dimethyl-1,3-dioxane-4,6-dione (14.00 g, 39.106 mmol) in MeOH (120 ml) was added N,N-dimethylmetheleneiminium iodide (CAS Number 33797-51-2; 18.08 g, 97.297 mmol) at rt. The reaction mixture was heated to 70° C. for 16 h. The resulting reaction mixture was cooled to rt and distilled under reduced pressure. The resulting mixture was dissolved in diethyl ether (500 ml) and washed with saturated $NaHCO_3$ solution (3×100 ml). The combined organic phase was dried over $Na_2SO_4$, filtered and concentrated under reduced pressure. The resulting residue was purified by flash chromatography (15% EtOAc in n-hexane) yielding ethyl 2-(4-bromo-2-nitrobenzyl) acrylate (10.00 g, 31.847 mmol). This material was used in the following step without further purification.

Step c.

To a solution of ethyl 2-(4-bromo-2-nitrobenzyl) acrylate (10.00 g, 31.847 mmol) in MeCN (80 ml) was added a solution of N-(methoxymethyl)-N-(trimethylsilylmethyl) benzamine (CAS Number 93102-05-7; 9.829 g, 41.471 mmol) in MeCN (20 ml) at 0° C. AgF (4.444 g, 35.030 mmol) was portion wise added to the reaction mixture at 0° C. The reaction mixture was stirred at rt for 16 h. The resulting mixture was filtered through celite and washed with EtOAc (100 ml). The filtrate was diluted with water (100 ml) and extracted with EtOAc (10×100 ml). The combined organic phase was dried over $Na_2SO_4$, filtered and concentrated under reduced pressure. The residue was purified by column chromatography (11% EtOAc in n-hexane) yielding methyl 1-benzyl-3-(4-bromo-2-nitrobenzyl) pyrrolidine-3-carboxylate (11.500 g, 26.558 mmol). LCMS: Method 1, 1.904, MS: ES+433.1, 435.1

Step d.

To a solution of methyl 1-benzyl-3-(4-bromo-2-nitrobenzyl) pyrrolidine-3-carboxylate (11.50 g, 26.558 mmol) in THF (100 ml) was added a solution of NH$_4$Cl (14.20 g, 265.47 mmol) in water (100 ml) followed by Fe Powder (14.81 g, 265.41 mmol) at rt. The reaction mixture was heated to 80° C. for 16 h. The resulting mixture was cooled to rt, filtered through celite and washed with EtOAc (5×100 ml). The resulting filtrate was diluted with water (200 ml) and extracted in EtOAc (10×100 ml). The combined organic phase was dried over Na$_2$SO$_4$, filtered and concentrated under reduced pressure. The resulting residue was purified by column chromatography (80-100% EtOAc in n-exane) yielding 1-benzyl-7'-bromo-1',4'-dihydro-2'H-spiro[pyrrolidine-3,3'-quinolin]-2'-one pyridine (7.140 g, 19.245 mmol). LCMS: Method 1, 1.781, MS: ES+ 371.1, 373.1

Step e.

To a stirred solution of 1-benzyl-7'-bromo-1',4'-dihydro-2'H-spiro[pyrrolidine-3,3'-quinolin]-2'-one pyridine (0.300 g, 0.801 mmol) and 5-methyl-1h-indazol-4-ylboronic acid (CAS Number 1245816-10-7; 0.214 g, 1.216 mmol) in 1,4-dioxane:water (4:1, 12 ml) was added Cs$_2$CO$_3$ (0.528 g, 1.624 mmol) at rt. The reaction mixture was degassed for 15 min before addition of Pd(PPh$_3$)$_4$ (0.046 g, 0.039 mmol) at rt. The reaction mixture was heated at 80° C. for 16 h. The resulting mixture was cooled to rt, diluted with water (20 ml) and extracted with EtOAc (5×50 ml). The combined organic phase was dried over Na$_2$SO$_4$, filtered and concentrated under reduced pressure. The obtained residue was purified by flash chromatography (40-80% EtOAc in n-hexane) yielding 1-benzyl-7'-(5-methyl-1H-indazol-4-yl)-1',4'-dihydro-2'H-spiro[pyrrolidine-3,3'-quinolin]-2'-one (0.200 g, 0.473 mmol). LCMS: Method 1, 1.783 min, MS: ES+ 423.52.

Step f.

To a solution of 1-benzyl-7'-(5-methyl-1H-indazol-4-yl)-1',4'-dihydro-2'H-spiro[pyrrolidine-3,3'-quinolin]-2'-one (0.180 g, 0.426 mmol) in THF (10 ml) were added K$_2$CO$_3$ (0.058 g, 0.420 mmol) and CNBr (0.045 g, 0.426 mmol) at 0° C. The reaction mixture was warmed to rt and stirred at rt for 6 h. The resulting mixture was poured into water (50 ml) and extracted with EtOAc (5×50 ml). The combined organic phase was dried over Na$_2$SO$_4$, filtered and concentrated under reduced pressure.

The resulting residue was purified by flash chromatography (3% MeOH in DCM), further purified by prep TLC using (3% MeOH in DCM) yielding the racemate of the desired compound (0.037 g, 0.104 mmol). LCMS: Method 1, 1.776 min, MS: ES+ 358.40, $^1$H NMR (400 MHz, DMSO-d6) δ ppm: 13.05 (s, 1H), 10.40 (s, 1H), 7.64 (s, 1H), 7.43-7.45 (m, 1H), 7.28-7.34 (m, 2H), 7.00-7.02 (m, 1H), 6.95 (s, 1H), 3.75 (d, J=9.6 Hz, 1H), 3.56-3.58 (m, 1H), 3.45-3.47 (m, 1H), 3.30 (d, J=9.6 Hz, 1H), 3.09-3.13 (m, 1H), 2.98-3.02 (m, 1H), 2.28 (s, 3H), 2.09-2.14 (m, 1H), 1.82-1.87 (m, 1H).

The enantiomers were separated by chiral SFC purification using 25% IPA in liquid CO$_2$ over 13 minutes on a Chiralpak IB 250×20.0 mm, 5 micron column with flow rate 70.0 ml/min and ABPR of 100 bar to yield the title compound. Absolute stereochemistry was assigned by analogy to Example 63. LCMS: Method 1 RT 1.888 min, MS: ES+ 358.32; Chiral HPLC: Column Chiralpak IB 250×4.6 mm, 5 micron, flow rate 1 ml/min, 6.82 min, 40% IPA in n-hexane RT 9.26 min; $^1$H NMR (400 MHz, DMSO-d6) δ ppm: 13.05 (s, 1H), 10.40 (s, 1H), 7.64 (s, 1H), 7.43-7.45 (m, 1H), 7.28-7.34 (m, 2H), 7.00-7.02 (m, 1H), 6.95 (s, 1H), 3.75 (d, J=9.6 Hz, 1H), 3.56-3.58 (m, 1H), 3.45-3.47 (m, 1H), 3.30 (d, J=9.6 Hz, 1H), 3.09-3.13 (m, 1H), 2.98-3.02 (m, 1H), 2.28 (s, 3H), 2.09-2.14 (m, 1H), 1.82-1.87 (m, 1H).

Example 133 7'-(1H-Indazol-4-yl)-2'-oxo-1',4'-dihydro-2'H-spiro[pyrrolidine-3,3'-quinoline]-1-carbonitrile

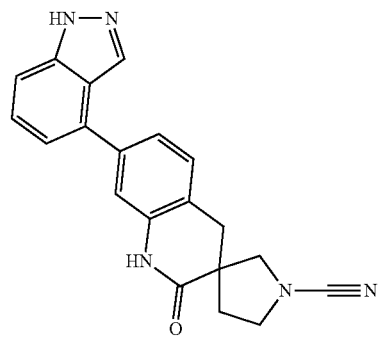 [SMILES: N#CN1CCC2(Cc3ccc(-c4cccc5[nH]ncc45)cc3NC2=O)C1]

This was prepared using a similar method to steps a-f of Example 132 using indazole-4-boronic acid (CAS Number 1023595-17-6) in step e. LCMS: Method 3 RT 3.815 min, MS: ES+ 343.99; $^1$H NMR (400 MHz, DMSO-d6) δ ppm: 13.24 (s, 1H), 10.44 (s, 1H), 8.18 (s, 1H), 7.54 (d, J=8.4 Hz, 1H), 7.40-7.44 (m, 1H), 7.31-7.36 (m, 3H), 7.20 (d, J=7.2 Hz, 1H), 3.73 (d, J=9.6 Hz, 1H), 3.53-3.58 (m, 1H), 3.41-3.50 (m, 1H), 3.28 (d, J=9.6 Hz, 1H), 3.08-3.12 (m, 1H), 2.88-2.97 (m, 1H), 2.06-2.12 (m, 1H), 1.79-1.86 (m, 1H).

Example 134 6'-(1H-Indazol-4-yl)-2'-oxo-1',4'-dihydro-2'H-spiro[pyrrolidine-3,3'-quinoline]-1-carbonitrile

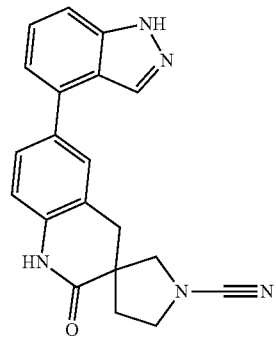 [SMILES: N#CN1CCC2(Cc3cc(-c4cccc5[nH]ncc45)ccc3NC2=O)C1]

This was prepared in a similar method to Example 133 using 5-bromo-2-nitrobenzaldehyde (CAS Number 20357-20-4) in the first step. LCMS: Method 3 RT 3.517 min, MS: ES+ 344.06; $^1$H NMR (400 MHz, DMSO-d6) δ ppm: 13.19 (s, 1H), 10.50 (s, 1H), 8.23 (s, 1H), 7.56-7.59 (m, 2H), 7.50 (d, J=8.4 Hz, 1H), 7.40 (t, J=8.4 Hz, 1H), 7.20 (d, J=6.4 Hz, 1H), 7.04 (d, J=8.0 Hz, 1H), 3.73 (d, J=9.6 Hz, 1H), 3.54-3.62 (m, 1H), 3.39-3.47 (m, 1H), 3.30 (d, J=9.6 Hz, 1H), 3.02-3.17 (m, 2H), 2.03-2.09 (m, 1H), 1.78-1.88 (m, 1H).

Scheme 3

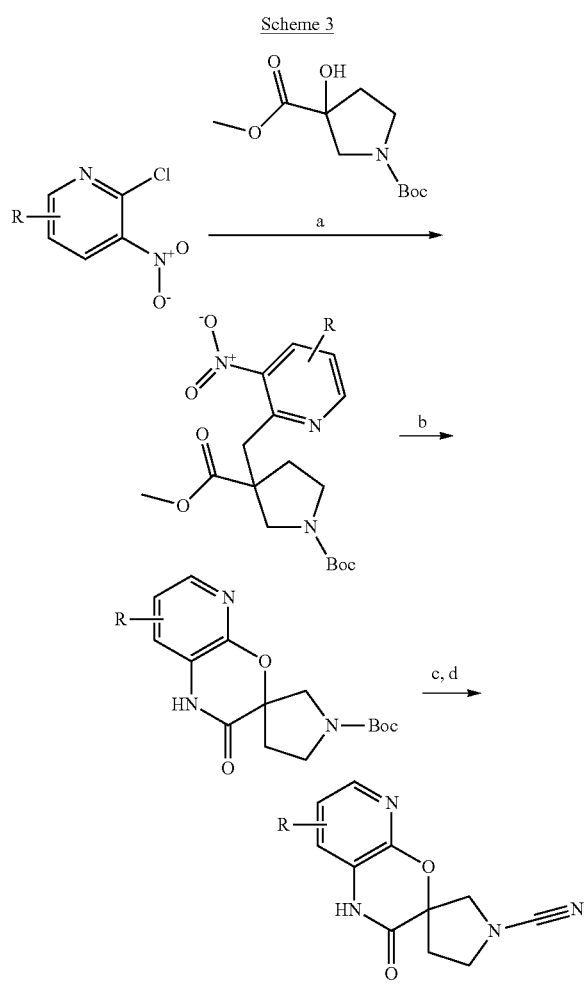

Reagents and conditions: a) Cs₂CO₃, DMF, 60° C.; b) Fe, NH₄Cl, THF, water, 60° C.; c) TFA, DCM, 0° C.; d) CNBr, K₂CO₃, THF, 0° C Example 48 2-Oxo-1,2-dihydrospiro[pyrido[2,3-b][1,4]oxazine-3,3'-pyrrolidine]-1'-carbonitrile Synthesis According to Scheme 3

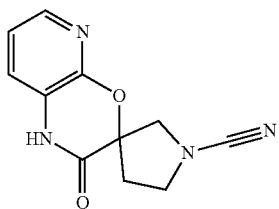 [SMILES: N#CN1CCC2(C1)Oc1ncccc1NC2=O]

Step a.

To a stirred solution of 2-chloro-3-nitropyridine (CAS Number 5470-18-8; 0.5 g, 3.154 mmol) in DMF (10 ml) was added 1-(tert-butyl) 3-methyl 3-hydroxypyrrolidine-1,3-dicarboxylate (Intermediate C; 0.62 g, 2.524 mmol) and Cs₂CO₃ (3.08 g, 9.463 mmol) at rt. The reaction mixture was stirred at 60° C. for 16 h. The resulting reaction mixture was poured into ice cold water (100 ml) and extracted with EtOAc (2×70 ml). The combined organic phase was dried over Na₂SO₄, filtered and concentrated under reduced pressure. The resulting residue was purified by flash chromatography using neutral alumina (25% EtOAc in hexane) yielding 1-(tert-butyl) 3-methyl 3-((3-nitropyridin-2-yl)oxy) pyrrolidine-1,3-dicarboxylate (0.12 g, 0.327 mmol). LCMS: Method 1, 2.20 min, MS: ES+368.5; ¹H NMR (400 MHz, DMSO-d6) δ ppm: 8.51 (d, J=8.0 Hz, 1H), 8.44 (dd, J=1.6 Hz, 4.8 Hz, 1H), 7.30-7.34 (m, 1H), 3.97-4.04 (m, 1H), 3.68-3.71 (m, 1H), 3.63 (s, 3H), 3.44-3.48 (m, 2H), 2.41-2.45 (m, 2H), 1.38 (s, 9H).

Step b.

To a stirred solution of 1-(tert-butyl) 3-methyl 3-((3-nitropyridin-2-yl)oxy)pyrrolidine-1,3-dicarboxylate (0.1 g, 0.272 mmol) in THF:water (1:1; 10 ml) was added iron powder (0.15 g, 2.724 mmol) and NH₄Cl (0.15 g, 2.724 mmol) at rt. The reaction mixture was stirred at 60° C. for 16 h. The resulting reaction mixture was filtered through celite bed. The filtrate was poured in water (50 ml) and extracted with EtOAc (2×30 ml). The combined organic phase was dried over Na₂SO₄, filtered and concentrated under reduced pressure. The resulting residue was purified by flash chromatography using neutral alumina (5% MeOH in DCM) yielding tert-butyl 2-oxo-1,2-dihydrospiro[pyrido [2,3-b][1,4]oxazine-3,3'-pyrrolidine]-1'-carboxylate (0.065 g, 0.213 mmol). LCMS: Method 1, 1.95 min, MS: ES+ 306.3; ¹H NMR (400 MHz, DMSO-d6) δ ppm: 11.09 (s, 1H), 7.85 (d, J=4.4 Hz, 1H), 7.29 (dd, J=1.6 Hz, 7.6 Hz, 1H), 7.09 (dd, J=4.8 Hz, 7.6 Hz, 1H), 3.68-3.76 (m, 1H), 3.50-3.57 (m, 2H), 3.39-3.45 (m, 1H), 2.32-2.40 (m, 1H), 2.14-2.17 (m, 1H), 1.39 (s, 9H).

Step c.

To a stirred solution of tert-butyl 2-oxo-1,2-dihydrospiro [pyrido[2,3-b][1,4]oxazine-3,3'-pyrrolidine]-1'-carboxylate (0.06 g, 0.197 mmol) in DCM (5 ml) was added TFA (0.3 ml) at 0° C. The reaction mixture was stirred at 0° C. for 1 h. The resulting reaction mixture was concentrated under reduced pressure. The resulting residue was azeotropically distilled using DCM (3×5 ml) and triturated with hexane (2×3 ml) yielding spiro[pyrido[2,3-b][1,4]oxazine-3,3'-pyrrolidin]-2(1H)-one TFA salt (0.08 g, quantitative). This material was used directly for the next step without further purification. LCMS: Method 1, 0.44 min, MS: ES+ 206.2; ¹H NMR (400 MHz, DMSO-d6) δ ppm: 11.29 (s, 1H), 9.48 (br, s, 1H), 7.80 (d, J=4.0 Hz, 1H), 7.33 (d, J=7.2 Hz, 1H), 7.13 (t, J=6.0 Hz, 1H), 3.77-3.81 (m, 1H), 3.63-3.66 (m, 1H), 3.39-3.45 (m, 2H), 2.31-2.36 (m, 2H).

Step d.

To a stirred solution of spiro[pyrido[2,3-b][1,4]oxazine-3,3'-pyrrolidin]-2(1H)-one TFA salt (0.08 g, 0.25 mmol) in THF (5 ml) was added K₂CO₃ (0.17 g, 1.253 mmol) at 0° C. The reaction mixture stirred at 0° C. for 5 min. Cyanogen bromide (0.032 g, 0.301 mmol) was added to the reaction mixture at 0° C. The reaction mixture at 0° C. for 15 min. The resulting reaction mixture filtered and excess of THF was distilled under reduced pressure. The resulting residue was purified by flash chromatography using neutral alumina (5% MeOH in DCM) yielding 2-oxo-1,2-dihydrospiro-[pyrido[2,3-b][1,4]oxazine-3,3'-pyrrolidine]-1'-carbonitrile (0.04 g, 0.174 mmol). LCMS: Method 3, 2.40 min, MS: ES+ 231.1; H NMR (400 MHz, DMSO-d6) δ ppm: 11.18 (s, 1H), 7.87 (d, J=8.0 Hz, 1H), 7.30 (d, J=6.8 Hz, 1H), 7.10 (dd, J=4.8 Hz, 7.2 Hz, 1H), 3.86 (d, J=11.2 Hz, 1H), 3.71 (d, J=11.6 Hz, 1H), 3.57-3.67 (m, 2H), 2.35-2.43 (m, 1H), 2.21-2.25 (m, 1H).

Scheme 4

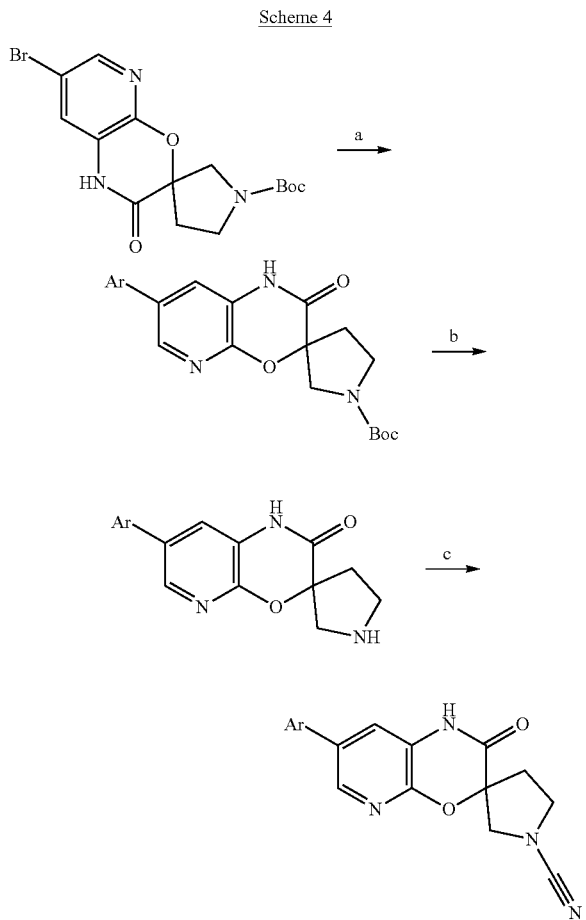

Reagents and conditions: a) Pd(PPh₃)₄, CsCO₃, 1,4-dioxane, water; b) TFA, DCM; c) cyanogen bromide, K₂CO₃, THF

Example 49 2-Oxo-7-phenyl-1,2-dihydrospiro[pyrido[2,3-b][1,4]oxazine-3,3'-pyrrolidine]-1'-carbonitrile

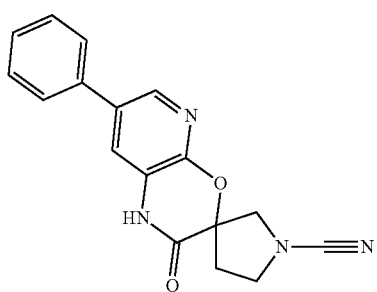 [SMILES: N#CN1CCC2(C1)Oc1ncc(-c3ccccc3)cc1NC2=O]

Step a.

To a stirred solution of tert-butyl 7-bromo-2-oxo-1,2-dihydrospiro[pyrido[2,3-b][1,4]oxazine-3,3'-pyrrolidine]-1'-carboxylate (Intermediate D; 0.25 g, 0.651 mmol) in 1,4-dioxane:water (4:1; 10 ml) was added $Cs_2CO_3$ (0.423 g, 1.301 mmol). The reaction mixture was degassed for 20 min before addition of Pd(PPh₃)₄ (0.075 g, 0.065 mmol) and phenylboronic acid (0.158 g, 1.301 mmol) at rt. The reaction mixture was heated at 90° C. for 18 h. The resulting reaction mixture was cooled to rt, poured into water (20 ml) and extracted with EtOAc (3×30 ml). The combined organic phase was separated and washed with brine (20 ml). The combined organic phase was separated, dried over $Na_2SO_4$, filtered and concentrated under reduced pressure. The residue was purified by flash chromatography (30% EtOAc in hexane) yielding tert-butyl 2-oxo-7-phenyl-1,2-dihydrospiro[pyrido[2,3-b][1,4]oxazine-3,3'-pyrrolidine]-1'-carboxylate (0.22 g, 0.783 mmol). LCMS: Method 1, 2.328 min, MS: ES+ 382.3; ¹H NMR (400 MHz, DMSO-d₆) δ ppm 11.19 (s, 1H), 8.16 (s, 1H), 7.62 (d, J=7.2 Hz, 2H), 7.50 (t, J=7.6 Hz, 3H), 7.41 (d, J=7.2 Hz, 1H), 3.72-3.80 (m, 1H), 3.54-3.62 (m, 2H), 3.44-3.51 (m, 1H), 2.18-2.24 (m, 1H), 2.33-2.41 (m, 1H), 1.42 (d, J=10.0 Hz, 9H).

Step b.

To a stirred solution of tert-butyl 2-oxo-7-phenyl-1,2-dihydrospiro[pyrido[2,3-b][1,4]oxazine-3,3'-pyrrolidine]-1'-carboxylate (0.21 g, 0.551 mmol) in DCM (10 ml) was added TFA (1.05 ml) at rt. The reaction mixture was stirred at rt for 5 h. The resulting reaction mixture was concentrated under vacuum. The obtained residue was azeotropically distilled with DCM (2×20 ml). The obtained material was washed with diethyl ether (2×20 ml) and dried under vacuum yielding 7-phenylspiro[pyrido[2,3-b][1,4]oxazine-3,3'-pyrrolidin]-2(1H)-one TFA salt (0.21 g, 0.531 mmol). LCMS: Method 1, 1.578 min, MS: ES+ 282.18.

Step c.

To a stirred solution of 7-phenylspiro[pyrido[2,3-b][1,4]oxazine-3,3'-pyrrolidin]-2(1H)-one TFA salt (0.2 g, 0.506 mmol) in THF (10 ml) was added $K_2CO_3$ (0.208, 1.517 mmol) at 0° C. The reaction mixture was stirred at 0° C. for 10 min. Cyanogen bromide (0.063 g, 0.607 mmol) at 0° C. The reaction mixture was stirred at rt for 30 min. The resulting reaction mixture was poured into water (10 ml) and extracted with EtOAc (3×30 ml). The combined organic phase was separated and washed with brine (20 ml). The combined organic phase was dried over $Na_2SO_4$, filtered and concentrated under reduced pressure. The resulting residue was purified by flash chromatography (1.4% MeOH in DCM) yielding 2-oxo-7-phenyl-1,2-dihydrospiro[pyrido[2,3-b][1,4]oxazine-3,3'-pyrrolidine]-1'-carbonitrile (0.085 g, 0.278 mmol). LCMS: Method 1, 1.855 min, MS: ES+ 307.37; ¹H NMR (400 MHz, DMSO-d₆) δ ppm 11.28 (s, 1H), 8.17 (d, J=2.0 Hz, 1H), 7.62 (d, J=1.2 Hz, 2H), 7.50 (t, J=7.2 Hz, 3H), 7.41 (J=7.6 Hz, 1H), 3.88 (d, J=11.6 Hz, 1H), 3.77 (dd, J=1.2 Hz, 11.2 Hz, 1H), 3.60-3.72 (m, 2H), 2.38-2.44 (m, 1H), 2.27-2.32 (m, 1H).

Compounds in Table 4 were prepared in a similar manner to Example 49.

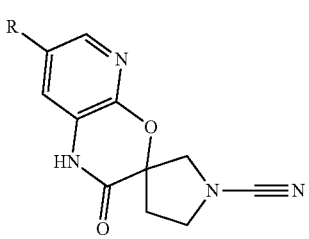

TABLE 4

| Example | R | Name | Boronic Acid CAS Number | LCMS method | LCMS RT (min) | MS ES+ | 1H NMR (400 MHz, DMSO-d6) δ ppm |
|---|---|---|---|---|---|---|---|
| 50 | 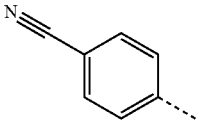 | 7-(4-Cyanophenyl)-2-oxo-1,2-dihydrospiro[pyrido[2,3-b][1,4]oxazine-3,3'-pyrrolidine]-1'-carbonitrile | 126747-14-6 | 2 | 3.38 | 332.13 | 11.33 (s, 1 H), 8.28 (d, J = 2 Hz, 1 H), 7.96 (d, J = 8.4 Hz, 2 H), 7.84 (d, J = 8.4 Hz, 2 H), 7.54 (d, J = 2.4 Hz, 1 H), 3.89 (d, J = 11.2 Hz, 1 H), 3.76-3.79 (dd, J = 11.2, 1.2 Hz, 1 H), 3.59-3.71 (m, 2 H), 2.39-2.41 (m, 1 H), 2.28-2.33 (m, 1 H). |
| 51 | 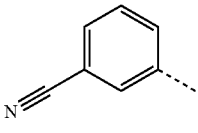 | 7-(3-Cyanophenyl)-2-oxo-1,2-dihydrospiro[pyrido[2,3-b][1,4]oxazine-3,3'-pyrrolidine]-1'-carbonitrile | 150255-96-2 | 2 | 3.39 | 332.08 | 11.34 (s, 1 H), 8.27 (d, J = 2 Hz, 1 H), 8.16 (s, 1 H), 7.97 (d, J = 8 Hz, 1 H), 7.88 (d, J = 8.8 Hz, 1 H), 7.70 (t, J = 7.6 Hz, 1 H), 7.53-7.54 (m, 1 H), 3.89 (d, J = 10.8 Hz, 1H), 3.77 (d, J = 11.2 Hz, 1 H), 3.60-3.72 (m, 2 H), 2.39-2.45 (m, 1 H), 2.27-2.33 (m, 1 H). |
| 52 | 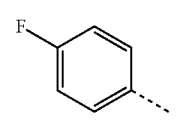 | 7-(4-Fluorophenyl)-2-oxo-1,2-dihydrospiro[pyrido[2,3-b][1,4]oxazine-3,3'-pyrrolidine]-1'-carbonitrile | 1765-93-1 | 2 | 3.53 | 325.14 | 11.28 (s, 1 H), 8.16 (d, J = 2 Hz, 1 H), 7.55-7.68 (m, 2 H), 7.45-7.46 (m, 1 H), 7.30-7.35 (m, 2 H), 3.88 (d, J = 11.2 Hz, 1 H), 3.76 (d, J = 11.6 Hz, 1 H), 3.59-3.71 (m, 2 H), 2.37-2.45 (m, 1 H), 2.26-2.32 (m, 1 H). |
| 53 | 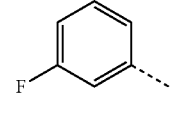 | 7-(3-Fluorophenyl)-2-oxo-1,2-dihydrospiro[pyrido[2,3-b][1,4]oxazine-3,3'-pyrrolidine]-1'-carbonitrile | 768-35-4 | 2 | 3.64 | 325.09 | 11.29 (s, 1 H), 8.23 (d, J = 2.4 Hz, 1 H), 7.46-7.57 (m, 4 H), 7.23-7.27 (m, 1 H), 3.89 (d, J = 11.2 Hz, 1 H), 3.77 (d, J = 11.6 Hz, 1 H), 3.60-3.72 (m, 2 H), 2.39-2.44 (m, 1 H), 2.27-2.33 (m, 1 H). |
| 135 | 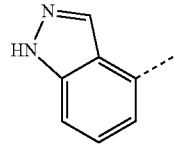 | 7-(1H-Indazol-4-yl)-2-oxo-1,2-dihydrospiro[pyrido[2,3-b][1,4]oxazine-3,3'-pyrrolidine]-1'-carbonitrile | 1023595-17-6 | 3 | 2.826 | 346.98 | 13.33 (s, 1 H), 11.24 (s, 1 H), 8.23 (d, J = 2.0 Hz, 1 H), 8.19 (s, 1 H), 7.66 (d, J = 2.4 Hz, 1 H), 7.59 (d, J = 8.4 Hz, 1 H), 7.45 (t, J = 8.4 Hz, 1 H), 7.24 (d, J = 6.8 Hz, 1 H), 3.89-3.92 (m, 1 H), 3.78-3.81 (m, 1 H), 3.61-3.73 (m, 2 H), 2.38-2.43 (m, 1 H), 2.32-2.36 (m, 1 H). |
| 136 | 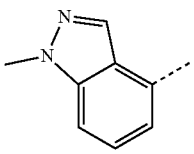 | 7-(1-Methyl-1H-indazol-4-yl)-2-oxo-1,2-dihydrospiro[pyrido[2,3-b][1,4]oxazine-3,3'-pyrrolidine]-1'-carbonitrile | 1001907-60-3 | 3 | 2.988 | 361.10 | 11.23 (s, 1 H), 8.23 (d, J = 2.0 Hz, 1 H), 8.16 (s, 1 H), 7.63-7.69 (m, 2 H), 7.51 (t, J = 8.0 Hz, 1 H), 7.28 (d, J = 7.2 Hz, 1 H), 4.10 (s, 3 H), 3.89-3.92 (m, 1 H), 3.79-3.82 (m, 1 H), 3.64-3.71 (m, 2 H), 2.41-2.45 (m, 1 H), 2.33-2.36 (m, 1 H). |
| 137 | 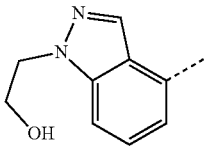 | 7-(1-(2-Hydroxyethyl)-1H-indazol-4-yl)-2-oxo-1,2-dihydrospiro[pyrido[2,3-b][1,4]oxazine-3,3'-pyrrolidine]-1'-carbonitrile | Intermediate F | 3 | 2.596 | 391.15 | 11.24 (s, 1 H), 8.20 (d, J = 2.0 Hz, 1 H), 8.16 (s, 1 H), 7.70 (d, J = 8.4 Hz, 1 H), 7.62 (d, J = 2.0 Hz, 1 H), 7.46 (t, J = 8.4 Hz, 1 H), 7.23 (d, J = 7.2 Hz, 1 H), 4.86-4.88 (m, 1 H), 4.46-4.49 (m, 2 H), 3.87-3.90 (m, 1 H), 3.77-3.83 (m, 3 H), 3.60-3.70 (m, 2 H), 2.39-2.42 (m, 1 H), 2.31-2.34 (m, 1 H). |
| 138 | 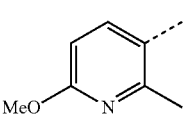 | 7-(6-Methoxy-2-methylpyridin-3-yl)-2-oxo-1,2-dihydrospiro[pyrido[2,3-b][1,4]oxazine-3,3'-pyrrolidine]-1'-carbonitrile | 459856-12-3 | 3 | 3.107 | 352.10 | 11.24 (s, 1 H), 7.86 (d, J = 2.0 Hz, 1 H), 7.58 (d, J = 8.4 Hz, 1 H), 7.24 (d, J = 2.0 Hz, 1 H), 6.74 (d, J = 8.4 Hz, 1 H), 3.88-3.90 (m, 1 H), 3.87 (s, 3 H), 3.76-3.79 (m, 1 H), 3.62-3.70 (m, 2 H), 2.41-2.44 (m, 1 H), 3.37 (s, 3 H), 2.32-2.36 (m, 1 H). |

Example 54 2-Oxo-6-phenyl-1,2-dihydrospiro[pyrido[2,3-b][1,4]oxazine-3,3'-pyrrolidine]-1'-carbonitrile

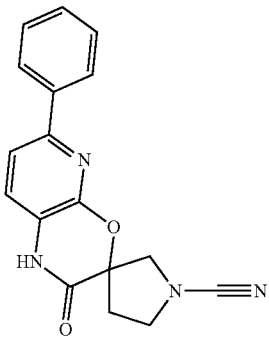 [SMILES: N#CN1CCC2(C1)Oc1nc(-c3ccccc3)ccc1NC2=O]

This was prepared by a similar method to Example 49 using Intermediate G and 2,6-dichloro-3-nitropyridine. LCMS: Method 2 RT 3.624 min, MS: ES+ 307.21; $^1$H NMR (400 MHz, DMSO-d6) δ ppm: 11.25 (s, 1H), 7.97 (d, J=7.6 Hz, 2H), 7.69 (d, J=8 Hz, 1H), 7.36-7.48 (m, 4H), 3.89 (d, J=11.2 Hz, 1H), 3.78 (d, J=11.2 Hz, 1H), 3.64-3.68 (m, 2H), 2.39-2.41 (m, 1H), 2.30-2.32 (m, 1H).

Example 139 6-(1H-Indazol-4-yl)-2-oxo-1,2-dihydrospiro[pyrido[2,3-b][1,4]oxazine-3,3'-pyrrolidine]-1'-carbonitrile

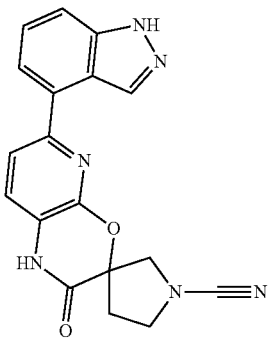 [SMILES: N#CN1CCC2(C1)Oc1nc(-c3cccc4[nH]ncc34)ccc1NC2=O]

This was prepared by a similar method to Example 135 using Intermediate G and 2,6-dichloro-3-nitro-pyridine. LCMS: Method 3 RT 2.947 min, MS ES+ 347.05; $^1$H NMR (400 MHz, DMSO-d6) δ ppm: 13.20 (s, 1H), 11.31 (s, 1H), 8.59 (s, 1H), 7.80 (d, J=8.0 Hz, 1H), 7.63 (d, J=7.2 Hz, 1H), 7.58 (d, J=8.4 Hz, 1H), 7.41-7.44 (m, 2H), 3.88-3.91 (m, 1H), 3.80-3.83 (m, 1H), 3.67-3.71 (m, 2H), 2.38-2.43 (m, 1H), 2.32-2.36 (m, 1H).

Example 140 7-(1-(2-Methoxyethyl)-1H-indazol-4-yl)-2-oxo-1,2-dihydrospiro[pyrido[2,3-b][1,4]oxazine-3,3'-pyrrolidine]-1'-carbonitrile

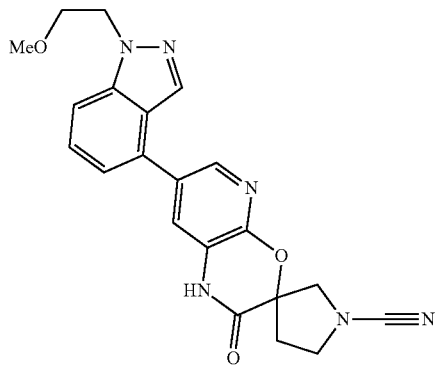 [SMILES: COCCn1ncc2c(-c3cnc4c(c3)NC(=O)C3(CCN(C#N)C3)O4)cccc21]

This was prepared in a similar method to Intermediate F/Example 137 using 2-bromoethyl methyl ether (CAS Number 6482-24-2). LCMS: Method 3 RT 3.072 min, MS: ES+ 405.15; $^1$H NMR (400 MHz, DMSO-d6) δ ppm: 11.26 (s, 1H), 8.23 (d, J=2.0 Hz, 1H), 8.19 (s, 1H), 7.73 (d, J=8.8 Hz, 1H), 7.64 (d, J=2.0 Hz, 1H), 7.48 (t, J=8.4 Hz, 1H), 7.26 (d, J=6.8 Hz, 1H), 4.61-4.63 (m, 2H), 4.00-4.03 (m, 1H), 3.77-3.90 (m, 3H), 3.61-3.71 (m, 2H), 3.20 (s, 3H), 2.41-2.44 (m, 1H), 2.32-2.36 (m, 1H).

Example 141 1'-Cyano-N-(4-fluorophenyl)-2-oxo-1,2-dihydrospiro[pyrido[2,3-b][1,4]oxazine-3,3'-pyrrolidine]-6-carboxamide

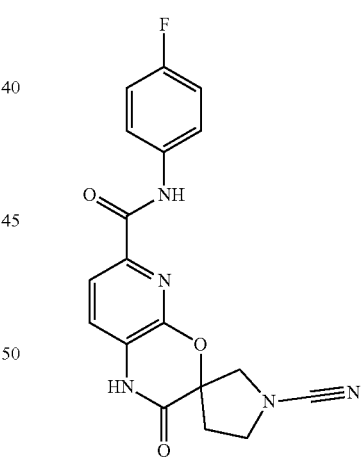

Step a.

To a solution of tert-butyl 6-bromo-2-oxo-1,2-dihydrospiro[pyrido[2,3-b][1,4]oxazine-3,3'-pyrrolidine]-1'-carboxylate (Intermediate G; 0.300 g, 0.783 mmol) in dry MeOH (5 ml) was added NaOAc (0.322 g, 3.912 mmol) at rt prepared in auto clave. The reaction mixture was degassed for 30 min before addition of PdCl$_2$(dppf) DCM complex (0.046 g, 0.039 mmol) at rt and 25 kg/cm$^2$H$_2$ pressure was applied in the autoclave. The reaction mixture was heated to 100° C. for 48 h. The resulting reaction mixture was combined with one other batch prepared on the same scale by an identical method. The resulting reaction mixture was cooled to rt and filtered through celite. The resulting filtrate was concentrated under reduced pressure. The resulting residue was purified by flash chromatography (1.7% MeOH in DCM) yielding 1'-(tert-butyl) 6-methyl 2-oxo-1,2-dihydrospiro[pyrido[2,3-b][1,4]oxazine-3,3'-pyrrolidine]-1',6-dicarboxylate (0.400 g, 1.102 mmol). LCMS: Method 1, 1.658 min, MS: ES+ 364.58 [M+1].

Step b.

To a solution of 1'-(tert-butyl) 6-methyl 2-oxo-1,2-dihydrospiro[pyrido[2,3-b][1,4]oxazine-3,3'-pyrrolidine]-1',6-dicarboxylate (0.400 g, 1.102 mmol) in THF:water (1:1, 5 ml) was added NaOH (0.088 g, 2.203 mmol) at rt. The reaction mixture was stirred at rt for 16 h. The resulting reaction mixture was poured in to water (50 ml) and acidified using saturated citric acid solution. The resulting mixture was extracted in EtOAc (3×50 ml). The combined organic phase was dried over Na$_2$SO$_4$, filtered and concentrated under reduced pressure yielding 1'-(tert-butoxycarbonyl)-2-oxo-1,2-dihydrospiro[pyrido[2,3-b][1,4]oxazine-3,3'-pyrrolidine]-6-carboxylic acid (0.350 g, 1.003 mmol). This material was used directly for the next step without further purification. LCMS: Method 1, 1.507 min. MS: ES+ 350.60 [M+1]

Step c.

To a solution of 1'-(tert-butoxycarbonyl)-2-oxo-1,2-dihydrospiro[pyrido[2,3-b][1,4]oxazine-3,3'-pyrrolidine]-6-carboxylic acid (0.330 g, 0.945 mmol) in THF (5 ml) were added HATU (0.538 g, 1.418 mmol) and DIPEA (0.244 g, 1.890 mmol) at rt. The reaction mixture was stirred at rt for 30 min. 4-fluoro aniline (CAS Number 371-40-4; 0.126 g, 1.134 mmol) was added to the reaction mixture at rt. The reaction mixture was stirred at rt for 3 h. The resulting mixture was poured into water (50 ml) and extracted with EtOAc (3×50 ml). The combined organic phase was dried over Na$_2$SO$_4$, filtered and concentrated under reduced pressure. The resulting residue was purified by flash chromatography (2.2% MeOH in DCM) yielding tert-butyl 6-((4-fluorophenyl)carbamoyl)-2-oxo-1,2-dihydrospiro[pyrido[2,3-b][1,4]oxazine-3,3'-pyrrolidine]-1'-carboxylate (0.250 g, 0.565 mmol). LCMS: Method 1, 2.059 min, MS: ES+ 443.70 [M+1]

Step d.

To a solution of tert-butyl 6-((4-fluorophenyl)carbamoyl)-2-oxo-1,2-dihydrospiro[pyrido[2,3-b][1,4]oxazine-3,3'-pyrrolidine]-1'-carboxylate (0.250 g, 0.565 mmol) in DCM (10 ml) was added TFA (1.25 ml, 5 V) at 0° C. The reaction mixture was stirred at rt for 1 h. The resulting reaction mixture was concentrated under reduced pressure. The obtained residue was co-distilled using MTBE (3×5 ml). The resulting residue was triturated with MTBE (2×5 ml). The obtained residue was dried under high vacuum yielding N-(4-fluorophenyl)-2-oxo-1,2-dihydrospiro[pyrido[2,3-b][1,4]oxazine-3,3'-pyrrolidine]-6-carboxamide TFA salt (0.250 g). This material was used directly for the next step without further purification. LCMS: Method 1, 1.406 min., MS: ES+ 343.50 [M+1]

Step e.

To a solution of N-(4-fluorophenyl)-2-oxo-1,2-dihydrospiro[pyrido[2,3-b][1,4]oxazine-3,3'-pyrrolidine]-6-carboxamide TFA salt (0.250 g, 0.548 mmol) in THF (5 ml) was added K$_2$CO$_3$ (0.234 g, 1.695 mmol) at rt. The reaction mixture was stirred at rt 15 min. The reaction mixture was cooled to 0° C. and treated with CNBr (0.058 g, 0.547 mmol). The reaction mixture was stirred for 1 h then poured into water (50 ml). The resulting precipitate was collected by filtration and dried under high vacuum yielding title compound (0.150 g, 0.408 mmol). LCMS: Method 3 RT 3.558 min, MS ES-366.05; $^1$H NMR (400 MHz, DMSO-d6) δ ppm: 11.52 (s, 1H), 10.38 (s, 1H), 7.85-7.86 (m, 3H), 7.43-7.45 (m, 1H), 7.13-7.18 (m, 2H), 3.90-3.93 (m, 1H), 3.80-3.83 (m, 1H), 3.62-3.68 (m, 2H), 2.38-2.43 (m, 1H), 2.29-2.33 (m, 1H).

Example 142 2-Oxo-6-(piperidine-1-carbonyl)-1,2-dihydrospiro[pyrido[2,3-b][1,4]oxazine-3,3'-pyrrolidine]-1'-carbonitrile

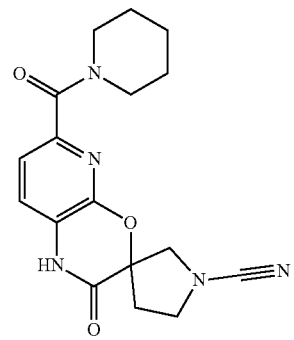 [SMILES: N#CN1CCC2(C1)Oc1nc(C(=O)N3CCCCC3)ccc1NC2=O]

This was prepared by a similar method to Example 141 using piperidine in step c. LCMS: Method 2 RT 2.859 min, MS ES+ 342.42; $^1$H NMR (400 MHz, DMSO-d6) δ ppm: 11.34 (s, 1H), 7.36 (d, J=8.0 Hz, 1H), 7.26 (d, J=7.6 Hz, 1H), 3.84-3.87 (m, 1H), 3.75-3.77 (m, 1H), 3.50-3.70 (m, 6H), 2.36-2.42 (m, 1H), 2.26-2.33 (m, 1H), 1.45-1.61 (m, 6H).

Example 143 1'-Cyano-2-oxo-N-phenyl-1,2-dihydrospiro[pyrido[2,3-b][1,4]oxazine-3,3'-pyrrolidine]-6-carboxamide

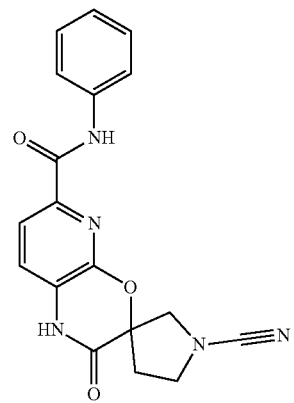

This was prepared by a similar method to Example 141 using aniline in step c. LCMS: Method 3 RT 3.337 min, MH+ ES− 348.05; $^1$H NMR (400 MHz, DMSO-d6) δ ppm: 11.55 (s, 1H), 10.29 (s, 1H), 7.85-7.90 (m, 3H), 7.47 (d, J=8.0 Hz, 1H), 7.34 (t, J=8.0 Hz, 2H), 7.10 (t, J=7.2 Hz, 1H), 3.93-3.96 (m, 1H), 3.83-3.86 (m, 1H), 3.63-3.73 (m, 2H), 2.41-2.45 (m, 1H), 2.33-2.36 (m, 1H).

Example 144 1'-Cyano-N-(2-fluorophenyl)-2-oxo-1,2-dihydrospiro[pyrido[2,3-b][1,4]oxazine-3,3'-pyrrolidine]-6-carboxamide

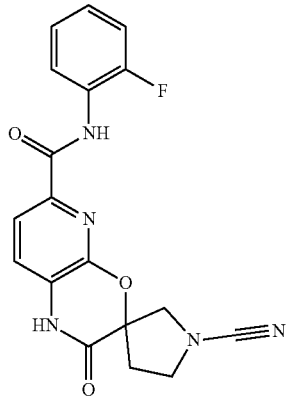 [SMILES: N#CN1CCC2(C1)Oc1nc(C(=O)Nc3ccccc3F)ccc1NC2=O]

This was prepared by a similar method to Example 141 using 2-fluoroaniline in step c. LCMS: Method 3, RT 3.392 min, MS ES− 366.05; $^1$H NMR (400 MHz, DMSO-d6) δ ppm: 11.58 (s, 1H), 10.07 (s, 1H), 7.93-7.95 (m, 1H), 7.89 (d, J=8.0 Hz, 1H), 7.48 (d, J=7.6 Hz, 2H), 7.29-7.32 (m, 1H), 7.22-7.24 (m, 2H), 3.91-3.93 (m, 1H), 3.85-3.88 (m, 1H), 3.65-3.71 (m, 2H), 2.41-2.45 (m, 1H), 2.33-2.36 (m, 1H).

Scheme 5

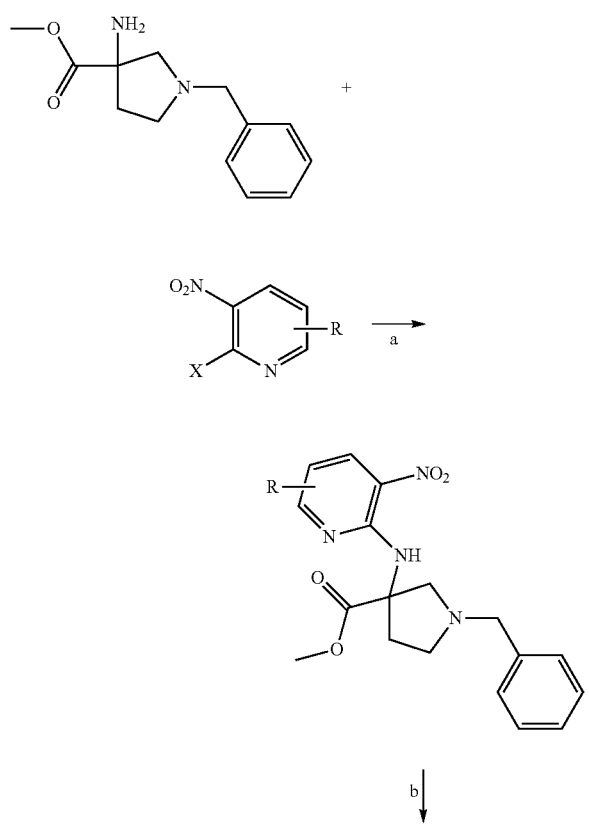

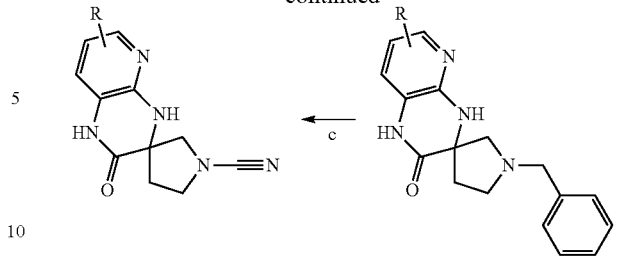

Reagents and conditions: a) K$_2$CO$_3$, toluene; b) Fe, NH$_4$Cl, THF, water; c) CNBr, K$_2$CO$_3$, THF

Example 55 2-Oxo-1,4-dihydro-2H-spiro[pyrido[2,3-b]pyrazine-3,3'-pyrrolidine]-1'-carbonitrile Synthesis According to Scheme 5

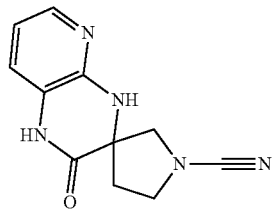 [SMILES: N#CN1CCC2(C1)Nc1ncccc1NC2=O]

Step a.

To a stirred solution of methyl 3-amino-1-benzylpyrrolidine-3-carboxylate (Intermediate A; 0.3 g, 1.280 mmol) and 2-fluoro-3-nitropyridine (CAS Number 1480-87-1; 0.236 g, 1.665 mmol) in toluene (15 ml) was added K$_2$CO$_3$ (0.265 g, 1.921 mmol) at rt. The reaction mixture was heated at 120° C. for 16 h. The reaction mixture was cooled to rt, poured into water (50 ml) and extracted with EtOAc (3×50 ml). The combined organic phase was separated, dried over Na$_2$SO$_4$, filtered and concentrated under reduced pressure. The resulting residue was purified by column chromatography (10-15% EtOAc in hexane) yielding methyl 1-benzyl-3-((3-nitropyridin-2-yl)amino)pyrrolidine-3-carboxylate (0.17 g, 0.477 mmol). LCMS: Method 1, 1.82 min, MS: ES+ 357.3; $^1$H NMR (400 MHz, DMSO-d$_6$) δ ppm: 8.45-8.47 (m, 1H), 8.37-8.40 (m, 1H), 7.90 (br, s, 1H), 7.33 (d, J=4.4 Hz, 4H), 7.23-7.28 (m, 1H), 6.83-6.87 (m, 1H), 6.74-6.77 (m, 1H), 3.60-3.70 (m, 2H), 3.54 (s, 3H), 3.07 (d, J=10.4 Hz, 1H), 2.90 (d, J=10.0 Hz, 1H), 2.83-2.89 (m, 1H), 2.55-2.62 (m, 1H), 2.12-2.16 (m, 1H).

Step b.

To a stirred solution of methyl 1-benzyl-3-((3-nitropyridin-2-yl)amino)pyrrolidine-3-carboxylate (0.19 g, 0.534 mmol) in THF (5 ml) was added a solution of ammonium chloride (0.285 g, 5.331 mmol) in water (5 ml) at rt. Iron powder (0.29 g, 5.337 mmol) was added at rt and the reaction mixture was heated at 60° C. for 2 h. The mixture was cooled to rt, poured into water (50 ml) and extracted with EtOAc (2×50 ml). The combined organic phase was separated, dried over Na$_2$SO$_4$, filtered and concentrated under reduced pressure. The resulting residue was purified by column chromatography (2% MeOH in DCM) yielding 1'-benzyl-1,4-dihydro-2H-spiro[pyrido[2,3-b]pyrazine-3,3'-pyrrolidin]-2-one (0.08 g, 0.272 mmol). LCMS: Method 1, 1.39 min, MS: ES+ 295.5; $^1$H NMR (400 MHz, DMSO-d$_6$)

δ ppm: 10.46 (s, 1H), 7.65 (dd, J=1.6 Hz, 5.2 Hz, 1H), 7.30-7.31 (m, 4H), 7.21-7.24 (m, 1H), 7.01 (s, 1H), 6.97 (d, J=6.8 Hz, 1H), 6.60-6.63 (m, 1H), 3.58 (s, 2H), 2.84-2.87 (m, 1H), 2.63 (q, J=9.6 Hz, 2H), 2.38-2.43 (m, 2H), 1.81-1.84 (m, 1H).

Step c.

To a stirred solution of 1'-benzyl-1,4-dihydro-2H-spiro[pyrido[2,3-b]pyrazine-3,3'-pyrrolidin]-2-one (0.07 g, 0.238 mmol) in THF (10 ml) was added $K_2CO_3$ (0.066 g, 0.476 mmol) at 0° C. The reaction was stirred at 0° C. for 5 min. Cyanogen bromide (0.025 g, 0.238 mmol) was added to the reaction mixture at 0° C. and the reaction mixture was stirred at rt for 16 h. The resulting mixture was poured in water (50 ml) and extracted with EtOAc (3×50 ml). The combined organic phase was separated, dried over $Na_2SO_4$, filtered and concentrated under reduced pressure. The resulting residue was purified by column chromatography (2% MeOH in DCM) yielding 2-oxo-1,4-dihydro-2H-spiro[pyrido[2,3-b]pyrazine-3,3'-pyrrolidine]-1'-carbonitrile (0.03 g, 0.131 mmol). LCMS: Method 3, 2.44 min, MS: ES+ 230.0; H NMR (400 MHz, DMSO-$d_6$) δ ppm: 10.71 (s, 1H), 7.70 (dd, J=1.6 Hz, 5.2 Hz, 1H), 7.39 (s, 1H), 7.02 (d, J=7.6 Hz, 1H), 6.65-6.69 (m, 1H), 3.78 (d, J=10.0 Hz, 1H), 3.65-3.71 (m, 1H), 3.46 (q, J=8.0 Hz, 1H), 3.26-3.29 (m, 1H), 2.27-2.33 (m, 1H), 1.90-1.97 (m, 1H).

Example 56 2-Oxo-6-(trifluoromethyl)-1,4-dihydro-2H-spiro[pyrido[2,3-b]pyrazine-3,3'-pyrrolidine]-1'-carbonitrile

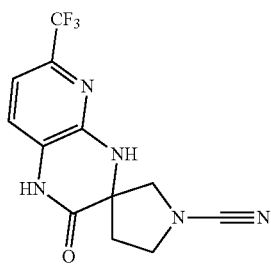 [SMILES: N#CN1CCC2(C1)Nc1nc(C(F)(F)F)ccc1NC2=O]

This was prepared using a similar procedure to Example 55 using 2-chloro-3-nitro-6-trifluoromethylpyridine (CAS Number 117519-08-1) in step a. LCMS: Method 2, 3.439 min, MS: ES+ 298.18; $^1$H NMR (400 MHz, DMSO-$d_6$) δ ppm: 11.08 (s, 1H), 8.13 (s, 1H), 7.10-7.15 (m, 2H), 3.80 (d, J=10.4 Hz, 1H), 3.67-3.73 (m, 1H), 3.46-3.52 (m, 1H), 3.37 (d, J=10.0 Hz, 1H), 2.33-2.42 (m, 1H), 1.96-2.02 (m, 1H).

Scheme 6

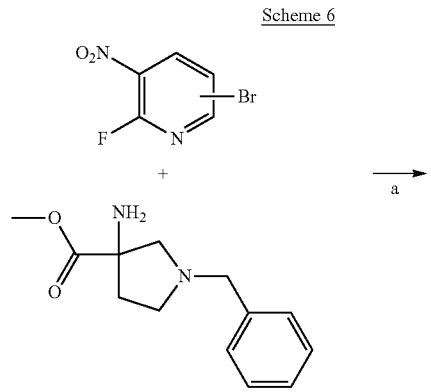

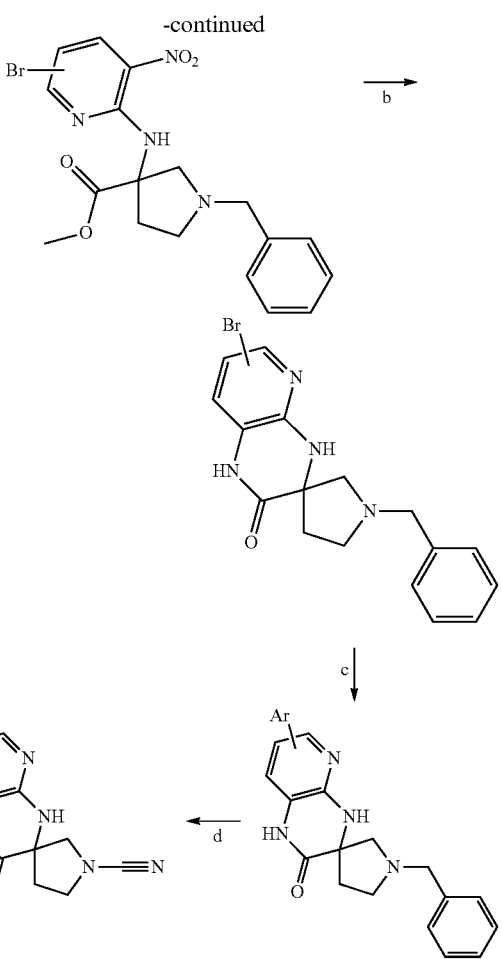

Reagents and conditions: a) $K_2CO_3$, toluene; b) Fe, $NH_4Cl$, THF, water; c) ArB(OH)$_2$, Pd(PPh$_3$)$_4$, $Cs_2CO_3$, 1,4-dioxane, water; d) CNBr, $K_2CO_3$, THF Example 57 2-Oxo-7-phenyl-1,4-dihydro-2H-spiro[pyrido[2,3-b]pyrazine-3,3'-pyrrolidine]-1'-carbonitrile Prepared According to Scheme 6

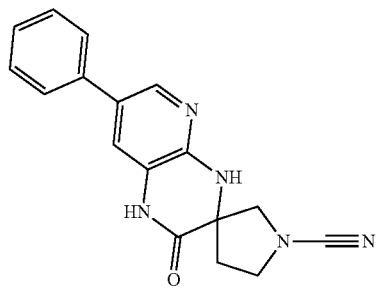 [SMILES: N#CN1CCC2(C1)Nc1ncc(-c3ccccc3)cc1NC2=O]

Steps a-b.

These were carried out using a similar procedure to steps a and b of Example 55 using 5-bromo-2-fluoro-3-nitropyridine (CAS Number 886372-98-1) in step a.

Step c.

This was carried out using a similar procedure to step a of Example 4 using phenylboronic acid.

Step d.

The title compound was formed by using a similar procedure to step c of Example 55.

LCMS: Method 3, 3.616 min, MS: ES+ 306.0; $^1$H NMR (400 MHz, DMSO-d$_6$) δ ppm: 10.83 (s, 1H), 8.03 (s, 1H), 7.37-7.57 (m, 5H), 7.29-7.37 (m, 2H), 3.80-3.82 (m, 1H), 3.69-3.70 (m, 1H), 3.48-3.49 (m, 1H), 3.38-3.41 (m, 1H), 2.33-2.35 (m, 1H), 1.99-2.00 (m, 1H).

Compounds in Table 5 were prepared in a similar manner to Example 57.

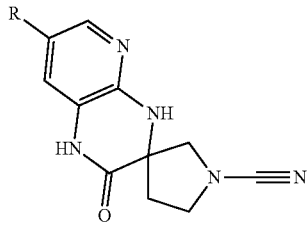

Example 61 3-Oxo-3,4-dihydro-1H-spiro[pyrido[2,3-b]pyrazine-2,3'-pyrrolidine]-1'-carbonitrile

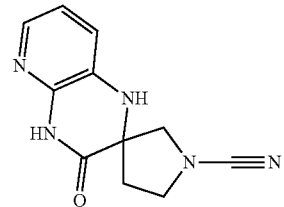 [SMILES: N#CN1CCC2(C1)Nc1cccnc1NC2=O]

Synthesised using a procedure similar to that described for Example 57 using 3-fluoro-2-nitropyridine in step a.
LCMS: Method 2 RT 2.247 min, MS: ES+ 230.25; $^1$H NMR (400 MHz, DMSO-d6) δ ppm: 11.02 (s, 1H), 7.65 (d, J=5.2 Hz, 1H), 7.06 (d, J=7.6 Hz, 1H), 6.84-6.87 (m, 1H), 6.76 (s, 1H), 3.78 (d, J=10.4 Hz, 1H), 3.61-3.67 (m, 1H), 3.47-3.53 (m, 1H), 3.29 (d, J=10.0 Hz, 1H), 2.21-2.36 (m, 1H), 1.84-1.90 (m, 1H).

TABLE 5

| Example | R | Name | Boronic Acid CAS Number | LCMS method | LCMS RT (min) | MS ES+ | $^1$H NMR (400 MHz, DMSO-d6) δ ppm |
|---|---|---|---|---|---|---|---|
| 58 | 4-cyanophenyl | 7-(4-Cyanophenyl)-2-oxo-1,4-dihydro-2H-spiro[pyrido[2,3-b]pyrazine-3,3'-pyrrolidine]-1'-carbonitrile | 126747-14-6 | 2 | 3.223 | ES− 329.08 | 10.89 (s, 1 H), 8.15 (d, J = 2.4 Hz, 1 H), 7.89 (d, J = 8.4 Hz, 2 H), 7.81 (s, 1 H), 7.75 (d, J = 8.4 Hz, 2 H), 7.31 (d, J = 2 Hz, 1 H), 3.82 (d, J = 10.0 Hz, 1 H), 3.67-3.72 (m, 1 H), 3.46-3.52 (m, 1 H), 3.38-3.40 (m, 1 H), 2.32-2.39 (m, 1 H), 1.97-2.01 (m, 1 H). |
| 59 | 4-fluorophenyl | 7-(4-Fluorophenyl)-2-oxo-1,4-dihydro-2H-spiro[pyrido[2,3-b]pyrazine-3,3'-pyrrolidine]-1'-carbonitrile | 1765-93-1 | 3 | 3.693 | 324.03 | 10.82 (s, 1 H), 8.00 (s, 1 H), 7.55-7.58 (m, 3 H), 7.23-7.29 (m, 3 H), 3.80 (d, J = 10.4 Hz, 1 H), 3.66-3.72 (m, 1 H), 3.45-3.49 (m, 1 H), 3.37 (d, J = 10.0 Hz, 1 H), 2.30-2.36 (m, 1 H), 1.94-2.00 (m, 1 H). |
| 60 | 3-fluorophenyl | 7-(3-Fluorophenyl)-2-oxo-1,4-dihydro-2H-spiro[pyrido[2,3-b]pyrazine-3,3'-pyrrolidine]-1'-carbonitrile | 768-35-4 | 3 | 3.751 | 323.96 | 10.83 (s, 1 H), 8.08 (d, J = 2 Hz, 1 H), 7.67 (s, 1 H), 7.45-7.51 (m, 1 H), 7.37-7.40 (m, 2 H), 7.27 (d, J = 2 Hz, 1 H), 7.13-7.17 (m, 1 H), 3.81 (d, J = 10.0 Hz, 1 H), 3.67-3.72 (m, 1 H), 3.45-3.51 (m, 1 H), 3.35 (d, J = 14.4 Hz, 1 H), 2.31-2.37 (m, 1 H), 1.95-2.01 (m, 1 H). |
| 145 | 5-methyl-1H-indazol-4-yl | 7-(5-Methyl-1H-indazol-4-yl)-2-oxo-1,4-dihydro-2H-spiro[pyrido[2,3-b]pyrazine-3,3'-pyrrolidine]-1'-carbonitrile | 1245816-10-7 | 3 | 2.665 | ES− 358.10 | 13.04 (s, 1 H), 10.77 (s, 1 H), 7.77 (d, J = 2.0 Hz, 1 H), 7.71 (s, 1 H), 7.58 (s, 1 H), 7.43 (d, J = 8.4 Hz, 1 H), 7.29 (d, J = 8.8 Hz, 1 H), 7.11 (s, 1 H), 3.86 (d, J = 10.0 Hz, 1 H), 3.72-3.73 (m, 1 H), 3.50-3.52 (m, 1 H), 3.43 (d, J = 10.0 Hz, 1 H), 2.39-2.42 (m, 1 H), 2.30 (s, 3 H), 1.96-2.05 (m, 1 H). |
| 146 | 1,4-dimethyl-1H-pyrazol-5-yl | 7-(1,4-Dimethyl-1H-pyrazol-5-yl)-2-oxo-1,4-dihydro-2H-spiro[pyrido[2,3-b]pyrazine-3,3'-pyrrolidine]-1'-carbonitrile | 1047644-76-7 | 3 | 2.367 | ES− 322.10 | 10.73 (s, 1 H), 7.64-7.66 (m, 2 H), 7.23 (s, 1 H), 6.91 (s, 1 H), 3.75 (d, J = 10.4 Hz, 1 H), 3.61-3.65 (m, 1 H), 3.59 (s, 3 H), 3.32-3.44 (m, 1 H), 3.29 (d, J = 10.4 Hz, 1 H), 2.24-2.36 (m, 1 H), 1.87-1.99 (m, 1 H), 1.85 (s, 3 H). |

Example 147 2-Oxo-6-phenyl-1,4-dihydro-2H-spiro[pyrido[2,3-b]pyrazine-3,3'-pyrrolidine]-1'-carbonitrile

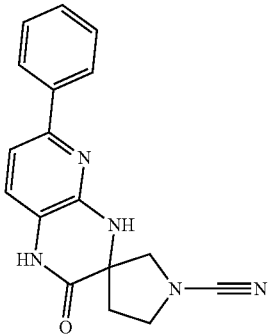 [SMILES: N#CN1CCC2(C1)Nc1nc(-c3ccccc3)ccc1NC2=O]

This was prepared out using a similar procedure to Example 57 using 6-bromo-2-chloro-3-nitropyridine (CAS Number 1430341-84-6) in step a. LCMS: Method 2, MS: 3.675 min, ES+ 306.32; $^1$H NMR (400 MHz, DMSO-d$_6$) δ ppm: 10.81 (s, 1H), 7.92-7.94 (m, 2H), 7.53 (s, 1H), 7.40-7.44 (m, 2H), 7.32-7.36 (m, 1H), 7.26 (d, J=8.0 Hz, 1H), 7.10 (d, J=7.6 Hz, 1H), 3.80 (d, J=10.4 Hz, 1H), 3.68-3.73 (m, 1H), 3.45-3.51 (m, 1H), 3.39 (d, J=10.4 Hz, 1H), 2.31-2.37 (m, 1H), 1.96-2.03 (m, 1H).

Example 62 6-Oxo-2,7-diazaspiro[4.4]nonane-2-carbonitrile

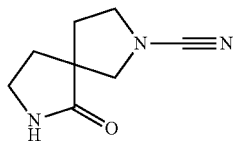 [SMILES: N#CN1CCC2(CCNC2=O)C1]

Step a.

To a solution of tert-butyl 6-oxo-2,7-diazaspiro[4.4]nonane-2-carboxylate (CAS Number 1194376-44-7; 0.2 g, 0.83 mmol) in DCM (15 ml) was added TFA (0.19 ml, 2.4 mmol) at 0° C. The reaction mixture was stirred at rt for 1 h. The resulting reaction mixture was concentrated under reduced pressure. The obtained residue was azeotropically distilled using DCM (2×5 ml). The obtained residue was triturated with diethyl ether (2×5 ml) yielding 2,7-diazaspiro[4.4]nonan-1-one TFA salt (0.31 g, quantitative). This material was directly used for the next step without further purification. LCMS: Method 4, 2.26 min, MS: ES+ 140.9; $^1$H NMR (400 MHz, DMSO-d$_6$) δ ppm 5.01 (br s, 1H), 3.34-3.41 (m, 2H), 3.20-3.32 (m, 4H), 3.12-3.18 (m, 1H), 2.04-2.14 (m, 2H), 1.94-2.02 (m, 2H).

Step b.

To a solution of 2,7-diazaspiro[4.4]nonan-1-one TFA salt (0.30 g, 1.10 mmol) in DMF (10 ml) was added K$_2$CO$_3$ (0.48 g, 3.50 mmol) at rt. The reaction mixture was stirred at rt for 10 min. The reaction mixture was cooled to 0° C. Cyanogen bromide (0.15 g, 1.40 mmol) was added to the reaction mixture at 0° C. The reaction mixture was stirred at rt for 1 h. The resulting reaction mixture was poured into water (40 ml) and extracted with 25% IPA:CHCl$_3$ mixture (5×40 ml). The combined organic phase was collected, dried over Na$_2$SO$_4$, filtered and concentrated under reduced pressure to get crude material (0.186 g) which was purified by preparative HPLC; mobile phase: (A) 10 mM Ammonium Acetate in water (B) 100% MeCN, column: Phenomenex Luna C8 (250×21.2) mm, 5 μm, flow rate: 17 ml/min yielded the title compound (0.088 g, 0.53 mmol). LCMS: Method 7, 3.192 min, MS: ES+ 166.00; Chiral HPLC: Method 5, RT 4.81 min, 6.01 min; $^1$H NMR (400 MHz, DMSO-d$_6$) δ ppm 7.87 (s, 1H), 3.51-3.55 (m, 1H), 3.38-3.45 (m, 1H), 3.31-3.36 (m, 2H), 3.17-3.21 (m, 2H), 1.92-2.06 (m, 3H), 1.80-1.85 (m, 1H).

Example 63 (R)-6-Oxo-2,7-diazaspiro[4.4]nonane-2-carbonitrile

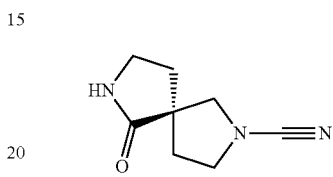

Example 62 was subjected to enantiomeric separation using preparative HPLC; mobile phase: (A) 0.1% Formic Acid in n-hexane (B) 0.1% Formic Acid in IPA, column: CHIRALPAK IC SFC (250×21) mm, 5 μm, flow rate: 15 ml/min, giving two enantiomeric products, Chiral HPLC: Method E, 4.53 min, 6.00 min. Absolute stereochemistry was assigned by X-ray crystallography. LCMS: Method 7, 3.16 min, MS: ES+ 166.0; Chiral HPLC: Method 5, 4.53 min; $^1$H NMR (400 MHz, DMSO-d$_6$) δ ppm 7.87 (s, 1H), 3.51-3.55 (m, 1H), 3.38-3.45 (m, 1H), 3.31-3.36 (m, 2H), 3.17-3.21 (m, 2H), 1.92-2.06 (m, 3H), 1.80-1.85 (m, 1H).

Example 64 (S)-2-Oxo-7-phenyl-1,2-dihydrospiro[pyrido[2,3-b][1,4]oxazine-3,3'-pyrrolidine]-1'-carbonitrile

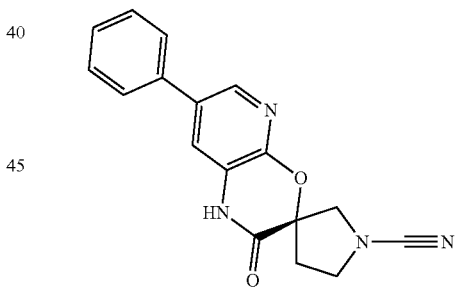

Example 49 was subjected to enantiomeric separation using Chiral SFC; mobile phase: (A) Liquid Carbon dioxide (Liq. CO$_2$) and (B) IPA:MeCN (50:50), column: CHIRALCEL OJ-H 250×21.0 mm, 5 micron, column flow was 75.0 ml/min and ABPR was 100 bar, giving two enantiomeric products, Chiral HPLC: Column CHIRALART SA 250×4.6 mm 5 μm, 100% MeOH, 6.82 and 8.37 min. Absolute stereochemistry was assigned by analogy to Example 63. LCMS: Method 2, 3.570 min, MS: ES− 305.07; Chiral HPLC: Column CHIRALART SA 250×4.6 mm 5 um, 6.82 min, 100% MeOH; H NMR (400 MHz, DMSO-d$_6$) δ ppm 11.27 (s, 1H), 8.17 (d, J=2.4 Hz, 1H), 7.62 (d, J=7.2 Hz, 2H), 7.48-7.52 (m, 3H), 7.41 (t, J=7.2 Hz, 1H), 3.88 (d, J=11.2 Hz, 1H), 3.76 (d, J=11.2 Hz, 1H), 3.62-3.69 (m, 2H), 2.38-2.44 (m, 1H), 2.28-2.32 (m, 1H).

Single enantiomers in Table 6 were separated from their racemates in a similar manner to Example 64.

TABLE 6

| Example | Structure | Name | Racemic example number | Chiral HPLC method | Chiral HPLC RT (min) | MS ES+ | ¹H NMR (400 MHz, DMSO-d6) δ ppm |
|---|---|---|---|---|---|---|---|
| 65 | 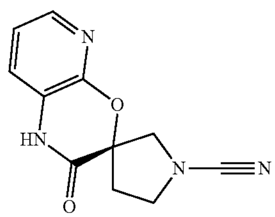 [SMILES: N#CN1CC[C@@]2(C1)Oc1ncccc1NC2=O] | (S)-2-Oxo-1,2-dihydrospiro[pyrido[2,3-b][1,4]oxazine-3,3'-pyrrolidine]-1'-carbonitrile | 48 | CHIRALART SA 250 × 4.6 mm 5 μm Mobile phase: IPA: MeCN (50:50) | 9.92 | 230.93 | 11.17 (s, 1 H), 7.87 (dd, J = 4.8, 1.6 Hz, 1 H), 7.30 (dd, J = 7.6, 1.6 Hz, 1 H), 7.08-7.12 (m, 1 H), 3.86 (d, J = 11.2 Hz, 1 H), 3.57-3.72 (m, 3 H), 2.33-2.43 (m, 1 H), 2.20-2.25 (m, 1 H). |
| 66 | 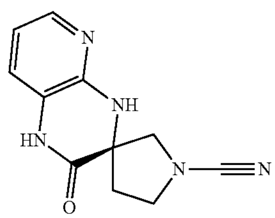 [SMILES: N#CN1CC[C@@]2(C1)Nc1ncccc1NC2=O] | (S)-2-Oxo-1,4-dihydro-2H-spiro[pyrido[2,3-b]pyrazine-3,3'-pyrrolidine]-1'-carbonitrile | 55 | CHIRALPAK IC 250 × 4.6 mm 5 μm Mobile phase: IPA: MeCN (50:50) | 4.12 | 229.93 | 10.71 (s, 1 H), 7.70 (dd, J = 5.1, 1.2 Hz, 1 H), 7.39 (s, 1 H), 7.02 (d, J = 6.8 Hz, 1 H), 6.65-6.68 (m, 1 H), 3.77 (d, J = 10.0 Hz, 1 H), 3.65-3.70 (m, 1 H), 3.39-3.52 (m, 1 H), 3.29-3.32 (m, 1 H), 2.26-2.33 (m, 1 H), 1.90-1.97 (m, 1 H). |
| 67 | 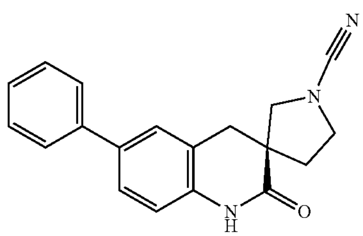 [SMILES: N#CN1CC[C@]2(Cc3cc(-c4ccccc4)ccc3NC2=O)C1] | (R)-2'-Oxo-6'-phenyl-1',4'-dihydro-2'H-spiro[pyrrolidine-3,3'-quinoline]-1-carbonitrile | 41 | CHIRALART SA 250 × 4.6 mm 5 μm Mobile phase: IPA | 7.75 | 304.41 | 10.45 (s, 1 H), 7.62-7.64 (m, 2 H), 7.49-7.52 (m, 2 H), 7.42-7.46 (m, 2 H), 7.30-7.34 (m, 1 H), 6.96 (d, J = 8.0 Hz, 1 H), 3.69-3.71 (m, 1 H), 3.48-3.57 (m, 1 H), 3.42-3.46 (m, 1 H), 3.25-3.29 (m, 1 H), 3.10 (d, J = 16.0 Hz, 1 H), 2.98 (d, J = 16.0 Hz, 1 H), 2.02-2.07 (m, 1 H), 1.77-1.84 (m, 1 H). |
| 68 | 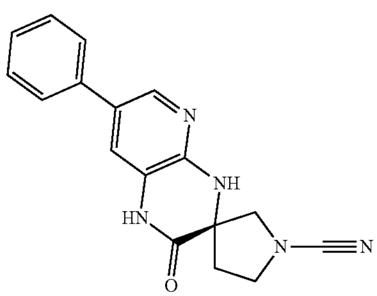 [SMILES: N#CN1CC[C@@]2(C1)Nc1ncc(-c3ccccc3)cc1NC2=O] | (S)-2-Oxo-7-phenyl-1,4-dihydro-2H-spiro[pyrido[2,3-b]pyrazine-3,3'-pyrrolidine]-1'-carbonitrile | 57 | CHIRALART SA 250 × 4.6 mm 5 μm Mobile phase: IPA | 6.6 | 306.07 | 10.83 (s, 1 H), 8.03 (s, 1 H), 7.52-7.57 (m, 3 H), 7.42-7.45 (m, 2 H), 7.27-7.34 (m, 2 H), 3.80-3.82 (m, 1 H), 3.69-3.70 (m, 1 H), 3.48-3.49 (m, 1 H), 3.38-3.41 (m, 1 H), 2.23-2.34 (m, 1 H), 1.94-2.01 (m, 1 H). |
| 69 | 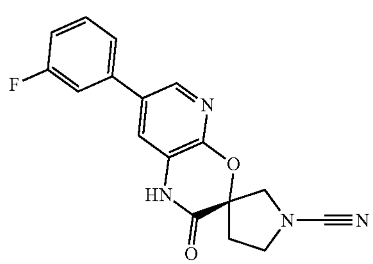 [SMILES: N#CN1CC[C@@]2(C1)Oc1ncc(-c3cccc(F)c3)cc1NC2=O] | (S)-7-(3-Fluorophenyl)-2-oxo-1,2-dihydrospiro[pyrido[2,3-b][1,4]oxazine-3,3'-pyrrolidine]-1'-carbonitrile | 53 | CHIRALPAK IC 250 × 4.6 mm 5 μm Mobile phase: IPA | 16.85 | 325.09 | 11.28 (s, 1 H), 8.23 (d, J = 2.4 Hz, 1H), 7.46-7.57 (m, 4 H), 7.23-7.27 (m, 1 H), 3.89 (d, J = 11.2 Hz, 1 H), 3.77 (d, J = 11.6 Hz, 1 H), 3.60-3.72 (m, 2 H), 2.39-2.44 (m, 1 H), 2.27-2.33 (m, 1 H). |

TABLE 6-continued

| Example | Structure | Name | Racemic example number | Chiral HPLC method | Chiral HPLC RT (min) | MS ES+ | 1H NMR (400 MHz, DMSO-d6) δ ppm |
|---|---|---|---|---|---|---|---|
| 70 | 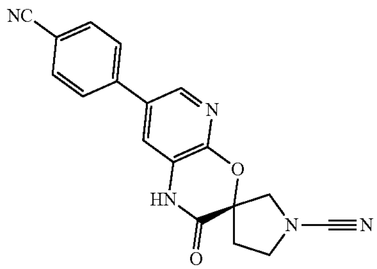 [SMILES: N#Cc1ccc(-c2cnc3c(c2)NC(=O)[C@@]2(CCN(C#N)C2)O3)cc1] | (S)-7-(4-Cyanophenyl)-2-oxo-1,2-dihydrospiro[pyrido[2,3-b][1,4]oxazine-3,3'-pyrrolidine]-1'-carbonitrile | 50 | CHIRALPAK OJ-H 250 × 4.6 mm 5 μm Mobile phase: 0.3% Diethyl amine in IPA:MeCN (80:20) | 11.88 | 332.28 | 11.33 (s, 1 H), 8.28 (d, J = 2 Hz, 1 H), 7.96 (d, J = 8.4 Hz, 2 H), 7.84 (d, J = 8.4 Hz, 2 H), 7.54 (d, J = 2.4 Hz, 1 H), 3.89 (d, J = 11.2 Hz, 1 H), 3.76-3.79 (dd, J = 11.2, 1.2 Hz, 1 H), 3.59-3.71 (m, 2 H), 2.39-2.41 (m, 1 H), 2.28-2.33 (m, 1 H). |
| 71 | 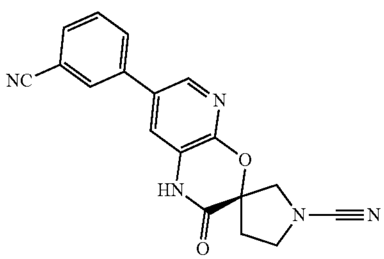 [SMILES: N#Cc1cccc(-c2cnc3c(c2)NC(=O)[C@@]2(CCN(C#N)C2)O3)c1] | (S)-7-(3-Cyanophenyl)-2-oxo-1,2-dihydrospiro[pyrido[2,3-b][1,4]oxazine-3,3'-pyrrolidine]-1'-carbonitrile | 51 | CHIRALPAK OJ-H 250 × 4.6 mm 5 μm Mobile phase: IPA | 5.04 | 332.18 | 11.37 (s, 1 H), 8.27 (d, J = 2 Hz, 1 H), 8.16 (s, 1 H), 7.97 (d, J = 8 Hz, 1 H), 7.88 (d, J = 8.8 Hz, 1 H), 7.70 (t, J = 7.6 Hz, 1 H), 7.53-7.54 (m, 1 H), 3.89 (d, J = 10.8 Hz, 1H), 3.77 (d, J = 11.2 Hz, 1 H), 3.60-3.72 (m, 2 H), 2.39-2.45 (m, 1 H), 2.27-2.33 (m, 1 H). |
| 72 | 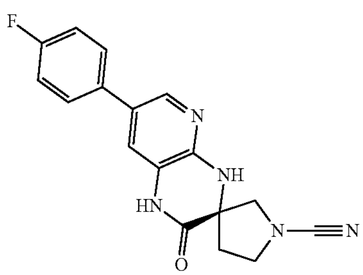 [SMILES: N#CN1CC[C@@]2(C1)Nc1ncc(-c3ccc(F)cc3)cc1NC2=O] | (S)-7-(4-Fluorophenyl)-2-oxo-1,4-dihydro-2H-spiro[pyrido[2,3-b]pyrazine-3,3'-pyrrolidine]-1'-carbonitrile | 59 | CHIRALPAK OJ-H 250 × 4.6 mm 5 μm Mobile phase: IPA | 10.63 | 323.84 | 10.82 (s, 1 H), 8.00 (s, 1 H), 7.55-7.58 (m, 3 H), 7.23-7.29 (m, 3 H), 3.80 (d, J = 10.4 Hz, 1 H), 3.66-3.72 (m, 1 H), 3.45-3.49 (m, 1 H), 3.37 (d, J = 10.0 Hz, 1 H), 2.30-2.36 (m, 1H), 1.94-2.00 (m, 1 H). |
| 73 | 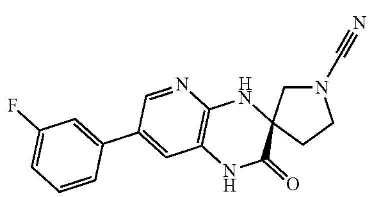 [SMILES: N#CN1CC[C@@]2(C1)Nc1ncc(-c3cccc(F)c3)cc1NC2=O] | (S)-7-(3-Fluorophenyl)-2-oxo-1,4-dihydro-2H-spiro[pyrido[2,3-b]pyrazine-3,3'-pyrrolidine]-1'-carbonitrile | 60 | CHIRALPAK OJ-H 250 × 4.6 mm 5 μm Mobile phase: IPA | 7.4 | 324.20 | 10.85 (s, 1 H ), 8.08 (d, J = 2.0 Hz, 1 H), 7.67 (s, 1 H), 7.45-7.51 (m, 1 H), 7.37-7.40 (m, 2 H), 7.27 (d, J = 2.0 Hz, 1 H), 7.13-7.17 (m, 1 H), 3.81 (d, J = 10.0 Hz, 1 H), 3.67-3.72 (m, 1 H), 3.45-3.51 (m, 1 H), 3.35 (d, J = 14.4 Hz, 1 H), 2.31-2.37 (m, 1 H), 1.95-2.01 (m, 1 H). |
| 74 | 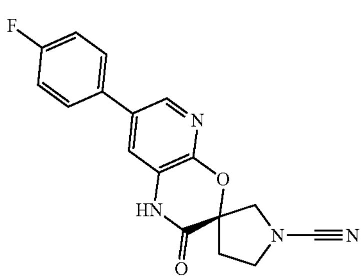 [SMILES: N#CN1CC[C@@]2(C1)Oc1ncc(-c3ccc(F)cc3)cc1NC2=O] | (S)-7-(4-Fluorophenyl)-2-oxo-1,2-dihydrospiro[pyrido[2,3-b][1,4]oxazine-3,3'-pyrrolidine]-1'-carbonitrile | 52 | CHIRALPAK OJ-H 250 × 4.6 mm 5 μm Mobile phase: IPA | 10.92 | 325.24 | 11.28 (s, 1 H), 8.16 (d, J = 2 Hz, 1 H), 7.55-7.68 (m, 2 H), 7.45-7.46 (m, 1 H), 7.30-7.35 (m, 2 H), 3.88 (d, J = 11.2 Hz, 1 H), 3.76 (d, J = 11.6 Hz, 1H), 3.59-3.71 (m, 2 H), 2.37-2.45 (m, 1 H), 2.26-2.32 (m, 1 H). |

Example 75 (S)-7-(3-Cyanophenyl)-2-oxo-1,4-dihydro-2H-spiro[pyrido[2,3-b]pyrazine-3,3'-pyrrolidine]-1'-carbonitrile

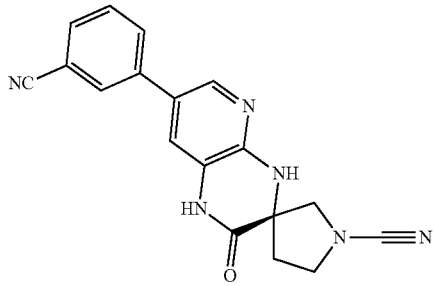 [SMILES: N#Cc1cccc(-c2cnc3c(c2)NC(=O)[C@@]2(CCN(C#N)C2)N3)c1]

Synthesised using a procedure similar to that described for Example 70 using 3-cyanophenylboronic acid (CAS Number 150255-96-2). LCMS: Method 3, 3.598 min, MS: ES+ 330.89; Chiral HPLC, column CHIRALPAK IC 250× 4.6 mm 5 µm Mobile phase: IPA:MeCN (50:50) RT 4.72; $^1$H NMR (400 MHz, DMSO-d6) δ ppm 10.86 (s, 1H), 8.12 (s, 1H), 8.03 (s, 1H), 7.87 (d, J=6.8 Hz, 1H), 7.72-7.82 (m, 2H), 7.61-7.65 (m, 1H), 7.29 (s, 1H), 3.79-3.82 (m, 1H), 3.65-3.76 (m, 1H), 3.47-3.49 (m, 1H), 3.48-3.43 (m, 1H), 2.28-2.35 (m, 1H), 1.91-2.03 (m, 1H).

Example 76 (8R)-8-Methyl-7,10-dioxo-2,6,9-triazaspiro[4.5]decane-2-carbonitrile

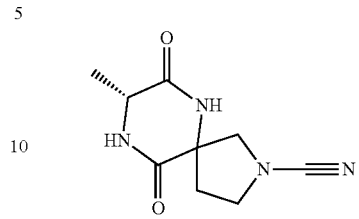

Step a.

To a solution of Boc-D-alanine (CAS Number 7764-95-6; 1.63 g, 8.615 mmol) in THF (32.6 ml) was added HATU (4.09 g, 10.775 mmol) and DIPEA (3.75 ml, 21.55 mmol) at rt. The reaction mixture was stirred at rt for 1 h. Methyl 3-amino-1-benzylpyrrolidine-3-carboxylate TFA salt (Intermediate E; 2.50 g, 7.181 mmol) was added to the reaction mixture. The reaction mixture was stirred at rt for 1 h. The resulting reaction mixture was poured into saturated NaHCO$_3$ solution (200 ml). The resulting mixture was extracted with EtOAc (2×200 ml). The combined organic phase was collected, dried over Na$_2$SO$_4$, filtered and concentrated under reduced pressure. The resulting residue was purified by flash chromatography (65% EtOAc in hexane)

Scheme 7

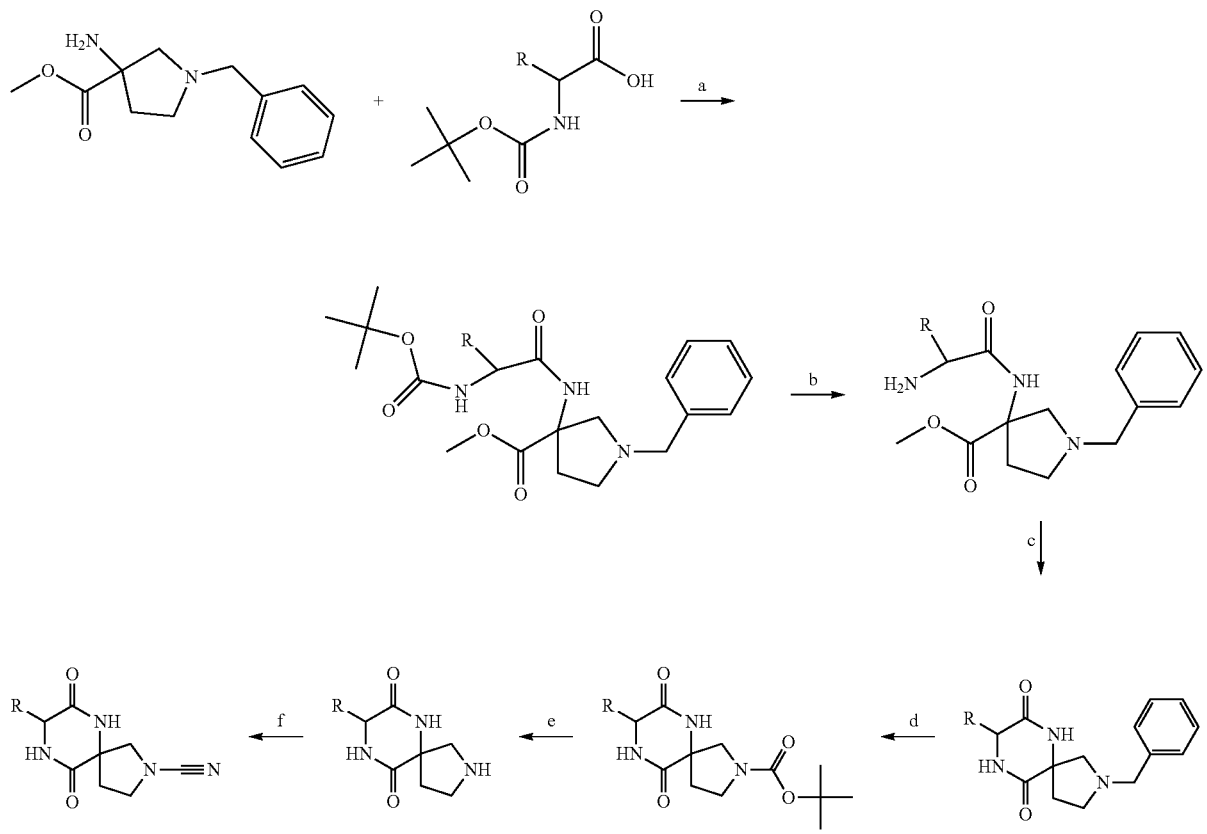

Reagents and conditions: a) HATU, DIPEA, THF; b) TFA, DCM; c) TBD, THF; d) Pd(OH)$_2$, polymethyl hydroxysilane, (Boc)$_2$O, EtOH; e) TFA, DCM; f) CNBr, K$_2$CO$_3$, THF yielding methyl 1-benzyl-3-((R)-2-((tert-butoxycarbonyl)amino)propanamido)pyrrolidine-3-carboxylate (2.30 g, 5.675 mmol). LCMS: Method 1, 1.67 min, MS: ES+ 406.7.

Step b.

To a solution of methyl 1-benzyl-3-((R)-2-((tert-butoxycarbonyl)amino)propanamido) pyrrolidine-3-carboxylate (2.30 g, 5.675 mmol) in DCM (23 ml) was added TFA (4.6 ml) at rt. The reaction mixture was stirred at rt for 1 h. The resulting reaction mixture was concentrated under reduced pressure. The obtained residue was triturated with diethyl ether (2×10 ml) yielding methyl 3-((R)-2-aminopropanamido)-1-benzylpyrrolidine-3-carboxylate TFA salt (2.5 g, quantitative). This material was used directly for the next step without further purification. LCMS: Method 4, 3.542 min, MS: ES+ 306.07.

Step c.

To a solution of methyl 3-((R)-2-aminopropanamido)-1-benzylpyrrolidine-3-carboxylate TFA salt (2.5 g, 5.966 mmol) in THF (25 ml) was added TBD (1.66 g, 11.933 mmol) at rt. The reaction mixture was stirred at rt for 1.5 h. The resulting reaction mixture was poured into water (150 ml) and extracted with EtOAc (3×150 ml). The combined organic phase was dried over Na₂SO₄, filtered and concentrated under reduced pressure. The resulting residue was purified by flash chromatography (60% EtOAc in hexane) yielding (8R)-2-benzyl-8-methyl-2,6,9-triazaspiro[4.5]decane-7,10-dione (0.90 g, 3.296 mmol). LCMS: Method 3, 3.04 min, MS: ES+ 274.5.

Step d.

To a solution of (8R)-2-benzyl-8-methyl-2,6,9-triazaspiro[4.5]decane-7,10-dione (0.40 g, 1.464 mmol) in ethanol (8 ml) was added 20% Pd(OH)₂ (50% moisture) (0.40 g) at rt. Poly(methylhydrosiloxane) (0.40 g) was added dropwise to the reaction mixture at rt followed by addition of (Boc)₂O (0.672 ml, 2.928 mmol) at rt. The reaction mixture was stirred at rt for 1 h. The resulting reaction mixture was combined with one other batch on the same scale prepared by an identical method and the reaction mixture was filtered through a celite pad and washed with MeOH (3×100 ml). The resulting filtrate was concentrated under reduced pressure. The resulting mixture was poured into saturated NaHCO₃ (100 ml) and extracted with EtOAc (2×100 ml). The combined organic phase was dried over Na₂SO₄, filtered and concentrated under reduced pressure. The resulting residue was purified by flash chromatography (4% MeOH in DCM) yielding tert-butyl (8R)-8-methyl-7,10-dioxo-2,6,9-triazaspiro[4.5]decane-2-carboxylate (0.50 g, 1.765 mmol). LCMS: Method 1, 1.70 min, MS: ES+ 284.2.

Step e.

To a solution of tert-butyl (8R)-8-methyl-7,10-dioxo-2,6,9-triazaspiro[4.5]decane-2-carboxylate (0.20 g, 0.706 mmol) in DCM (8 ml) was added TFA (0.4 ml) at rt. The reaction mixture was stirred at rt for 1 h. The resulting reaction mixture was concentrated under reduced pressure. The obtained residue was triturated with diethyl ether (2×2 ml) yielding (8R)-8-methyl-2,6,9-triazaspiro[4.5]decane-7,10-dione TFA salt (0.25 g, quantitative). This material was used directly for the next step without further purification. LCMS: Method 3, 0.803 min, MS: ES+ 184.1, 0.88 min.

Step f.

To a solution of (8R)-8-methyl-2,6,9-triazaspiro[4.5]decane-7,10-dione TFA salt (0.25 g, 0.841 mmol) in THF:DMF (9:1) (10 ml) was added K₂CO₃ (0.35 g, 2.525 mmol) at rt. Cyanogen bromide (0.107 g, 1.009 mmol) was added to the reaction mixture at rt. The reaction mixture was stirred at rt for 1 h. The resulting reaction mixture was concentrated under reduced pressure. The resulting residue was purified by flash chromatography (4.3% MeOH in DCM) yielding the title compound as a mixture of diastereomers (0.10 g, 0.480 mmol). LCMS: Method 3, 1.306 min, MS: ES+ 209.06, 1.52 min, MS: ES+ 209.1; ¹H NMR (400 MHz, DMSO-d6) δ ppm 8.61 (s, 2H), 8.40 (s, 2H), 4.01-4.04 (m, 2H), 3.77 (d, J=10 Hz, 1H), 3.32-3.79 (m, 7H), 2.37-2.50 (m, 1H), 2.26-2.33 (m, 1H), 1.92-2.06 (m, 2H), 1.23-1.28 (m, 6H).

Example 77 7,10-Dioxo-2,6,9-triazaspiro[4.5]decane-2-carbonitrile

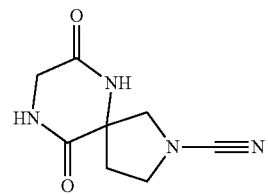 [SMILES: N#CN1CCC2(C1)NC(=O)CNC2=O]

Synthesised using a procedure similar to that described for Example 76, using Boc-L-glycine in step a. LCMS: Method 7, 2.89 min, MS: ES+ 195.2; ¹H NMR (400 MHz, DMSO-d₆) δ ppm: 8.69 (s, 1H), 8.30 (s, 1H), 3.83 (s, 2H), 0.71 (d, J=10.4 Hz, 1H), 3.60 (q, J=7.2 Hz, 1H), 3.51-3.55 (m, 1H), 3.47 (d, J=14.8 Hz, 1H), 2.32-2.41 (m, 1H), 1.96-2.03 (m, 1H).

Example 78 (8S)-8-Methyl-7,10-dioxo-2,6,9-triazaspiro[4.5]decane-2-carbonitrile

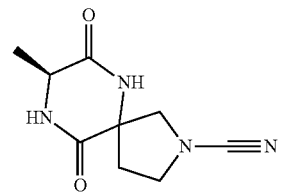

Synthesised as a mixture of diastereomers using a procedure similar to that described for Example 76, using Boc-L-alanine in step a. LCMS: Method 9, 9.39, 9.53 min, MS: ES− 207.0; ¹H NMR (400 MHz, DMSO-d₆) δ ppm: 8.63 (d, J=3.6 Hz, 2H), 8.42 (s, 2H), 4.00-4.39 (m, 2H), 3.78 (d, J=10 Hz, 1H), 3.45-3.66 (m, 6H), 3.37 (d, J=10 Hz, 1H), 2.37-2.44 (m, 1H), 2.26-2.33 (m, 1H), 1.93-2.06 (m, 2H), 1.24-1.28 (m, 6H).

Example 79 7,10-Dioxo-8-phenyl-2,6,9-triazaspiro[4.5]decane-2-carbonitrile

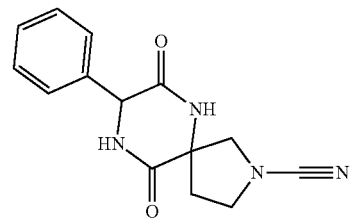 [SMILES: N#CN1CCC2(C1)NC(=O)C(c1ccccc1)NC2=O]

Synthesised as a mixture of diastereomers using a procedure similar to that described for Example 76, using 2-((tert-butoxycarbonyl)amino)-2-phenylacetic acid in step a. LCMS: Method 2, 2.51, 2.63 min, MS: ES− 269.4; $^1$H NMR (400 MHz, DMSO-$d_6$) δ ppm: 8.86 (s, 2H), 8.78 (s, 2H), 7.33-7.42 (m, 10H), 5.06-5.08 (m, 2H), 3.83 (d, J=10.4 Hz, 1H), 3.74 (d, J=10 Hz, 1H), 3.50-3.67 (m, 4H), 3.47 (d, J=10 Hz, 1H), 3.22 (d, J=10 Hz, 1H), 2.44-2.50 (m, 1H), 2.33-2.35 (m, 1H), 2.06-2.11 (m, 1H), 1.84-1.87 (m, 1H).

combined with one other batch on the same scale prepared by an identical method and quenched by addition of saturated ammonium chloride solution (100 ml). The resulting mixture was extracted with EtOAc (2×100 ml). The combined organic phase was dried over $Na_2SO_4$, filtered and concentrated under reduced pressure. The resulting residue was purified by column chromatography (5% EtOAc in hexane) yielding 1-(tert-butyl) 3-ethyl 3-(2-bromoallyl)pyr- Scheme 8

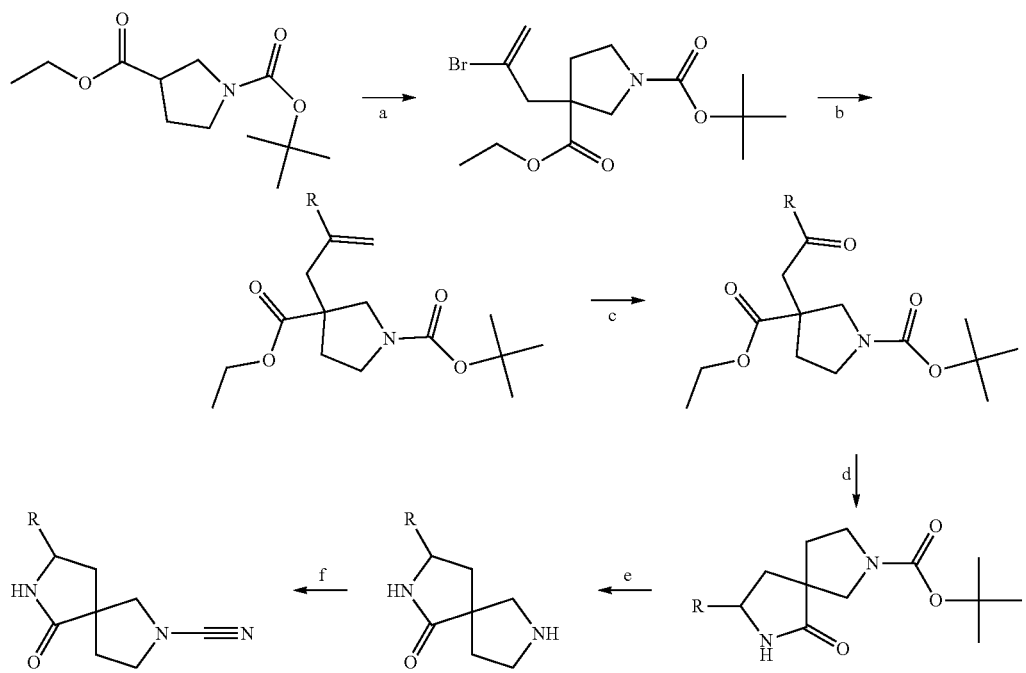

Reagents and conditions: a) LDA, 2,3-Dibromopropene, THF; b) KRBF$_3$, PdCl$_2$(dppf), Cs$_2$CO$_3$, toluene, water; c) K$_2$OsO$_4$•2H$_2$O, sodium periodate, acetone, water; d) NH$_4$OAc, NaCNBH$_3$, EtOH, MgSO$_4$; e) TFA, DCM; f) CNBr, Na$_2$CO$_3$, THF Example 80 8-Ethyl-6-oxo-2,7-diazaspiro[4.4]nonane-2-carbonitrile

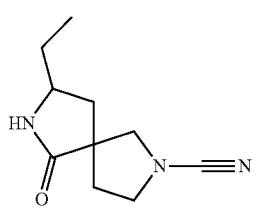

Step a.

To a solution of diisopropylamine (3.72 ml, 26.3 mmol) in dry THF (30 ml) was added 1.6M n-BuLi in hexane (15.4 ml, 24.6 mmol) at −78° C. The reaction mixture was stirred at −78° C. for 45 min. Ethyl 1-Boc-3-pyrrolidinecarboxylate (CAS Number 170844-49-2; 2.00 g, 8.22 mmol) was added to the reaction mixture at −78° C. and the reaction mixture was stirred at −78° C. for 1 h. 2,3-Dibromopropene (CAS Number 513-31-5; 1.23 ml, 12.33 mmol) was added in to the reaction mixture at −78° C. The resulting reaction mixture was warmed to 0° C. The resulting reaction mixture was rolidine-1,3-dicarboxylate (4.00 g, 11.077 mmol). LCMS: Method 1, 2.58 min, MS: ES+ 362.7

Step b.

To a solution of 1-(tert-butyl) 3-ethyl 3-(2-bromoallyl)pyrrolidine-1,3-dicarboxylate (0.50 g, 1.395 mmol) and potassium ethyltrifluoroborate (CAS Number 44248-07-9; 0.23 g, 1.661 mmol) in toluene:water (9:1) (5 ml) was added Cs$_2$CO$_3$ (1.35 g, 4.163 mmol) at rt. The reaction mixture was degassed with nitrogen for 20 min at rt before addition of PdCl$_2$(dppf) (0.10 g, 0.14 mmol) at rt. The reaction mixture was heated at 80° C. for 15 h. The resulting reaction mixture was combined with one other batch on the same scale prepared by an identical method then cooled to rt, poured into water (100 ml) and extracted with EtOAc (2×100 ml). The combined organic phase was washed with brine solution (50 ml), dried over Na$_2$SO$_4$, filtered and concentrated under reduced pressure. The resulting residue was purified by flash chromatography (8% EtOAc in hexane) yielding 1-(tert-butyl) 3-ethyl 3-(2-methylenebutyl)pyrrolidine-1,3-dicarboxylate (0.32 g, 1.028 mmol). LCMS: Method 1, 2.886 min, MS: ES+ 312.1.

Step c.

To a solution of 1-(tert-butyl) 3-ethyl 3-(2-methylenebutyl)pyrrolidine-1,3-dicarboxylate (0.30 g, 0.964 mmol) in acetone:water (1:1) (10 ml) was added potassium osmate (VI)dihydrate (0.014 g, 0.040 mmol) at rt. The reaction mixture was cooled to 10° C. Sodium metaperiodate (0.83 g, 3.840 mmol) was added portionwise over a period of 15 min at 10° C. The resulting reaction mixture was stirred at rt for 1 h. The resulting reaction mixture was diluted with water (75 ml) and extracted with EtOAc (2×75 ml). The combined organic phase was washed with brine solution (50 ml), dried over $Na_2SO_4$, filtered and concentrated under reduced pressure yielding 1-(tert-butyl) 3-ethyl 3-(2-oxobutyl)pyrrolidine-1,3-dicarboxylate (0.30 g, 0.957 mmol). LCMS: Method 1, 2.313 min, MS: ES+214.18 (M-Boc).

Step d.

To a solution of 1-(tert-butyl) 3-ethyl 3-(2-oxobutyl) pyrrolidine-1,3-dicarboxylate (0.30 g, 0.957 mmol) in ethanol (9 ml) were added ammonium acetate (1.11 g, 14.388 mmol) and $NaCNBH_3$ (0.24 g, 3.831 mmol) at rt. $MgSO_4$ (0.81 g, 6.715 mmol) was added at rt and the reaction mixture was heated at 80° C. for 15 h. The resulting mixture was concentrated under reduced pressure. The obtained residue was dissolved in EtOAc (100 ml), washed with saturated $NaHCO_3$ solution (50 ml), water (50 ml), brine solution (50 ml), dried over $Na_2SO_4$, filtered and concentrated under reduced pressure. The resulting residue was purified by flash chromatography (1.5% MeOH in DCM) yielding tert-butyl 8-ethyl-6-oxo-2,7-diazaspiro[4.4] nonane-2-carboxylate (0.045 g, 0.167 mmol). LCMS: Method 1, 2.04 min, MS: ES+ 213.2 (M-56).

Step e.

To a solution of tert-butyl 8-ethyl-6-oxo-2,7-diazaspiro [4.4]nonane-2-carboxylate (0.04 g, 0.159 mmol) in DCM (3 ml) was added TFA (0.5 ml) at rt. The reaction mixture was stirred at rt for 1 h. The resulting reaction mixture was concentrated under reduced pressure. The obtained residue was azeotropically distilled with diethylether (5 ml) yielding 3-ethyl-2,7-diazaspiro[4.4]nonan-1-one TFA salt (0.03 g, 0.106 mmol). MS: ES+ 169.2.

Step f.

To a solution of 3-ethyl-2,7-diazaspiro[4.4]nonan-1-one TFA salt (0.03 g, 0.106 mmol) in THF (2 ml) was added $NaHCO_3$ (0.018 g, 0.212 mmol) at rt. Cyanogen bromide (0.012 g, 0.117 mmol) was added to the reaction mixture at rt. The reaction mixture was stirred at rt for 1 h. The resulting reaction mixture was poured into water (50 ml) and extracted with EtOAc (2×30 ml). The combined organic phase was collected, dried over $Na_2SO_4$, filtered and concentrated under reduced pressure. The resulting residue was purified by column chromatography (1% MeOH in DCM) yielding the title compound as a mixture of diastereomers (0.008 g, 0.041 mmol). LCMS: Method 3, 2.78 min, MS: ES+ 194.0; $^1$H NMR (400 MHz, $CDCl_3$) δ ppm: 5.96 (s, 2H), 3.80 (d, J=9.6 Hz, 1H), 3.67-3.73 (m, 2H), 3.49-3.58 (m, 5H), 3.35 (d, J=9.2 Hz, 1H), 3.27 (d, J=9.6 Hz, 1H), 2.14-2.43 (m, 4H), 1.52-1.92 (m, 8H), 0.97 (t, J=14.8 Hz, 6H).

Example 81 8-Benzyl-6-oxo-2,7-diazaspiro[4.4] nonane-2-carbonitrile

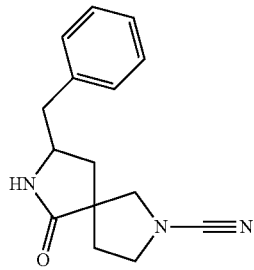 [SMILES: N#CN1CCC2(CC(Cc3ccccc3)NC2=O)C1]

Synthesised as a mixture of diastereomers using a procedure similar to that described for Example 80, using potassium benzyltrifluoroborate in step b. LCMS: Method 3, 3.57 min, MS: ES+ 356.1; $^1$H NMR (400 MHz, DMSO-d6) δ ppm: 8.12 (s, 1H), 7.29-7.31 (m, 2H), 7.22-7.24 (m, 3H), 3.78-3.81 (m, 2H), 3.47-3.52 (m, 2H), 3.23 (d, J=9.2 Hz, 1H), 2.89 (dd, J=4.8 Hz, 13.2 Hz, 1H), 2.58-2.63 (m, 1H), 1.96-2.05 (m, 2H), 1.59-1.70 (m, 2H).

Examples 82 and 83 8-Methyl-6-oxo-2,7-diazaspiro [4.4]nonane-2-carbonitrile

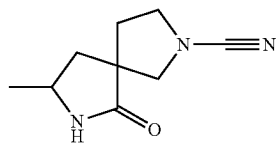

Step a.

A solution of 1-(tert-butyl) 3-ethyl pyrrolidine-1,3-dicarboxylate (CAS Number 170844-49-2; 4.0 g, 16.46 mmol) in THF (80 ml) was cooled to −78° C. 1M solution of LiHMDS in THF (21 ml, 21.39 mmol) was dropwise added to the reaction mixture at −78° C. The resulting reaction mixture was stirred at −78° C. for 30 min. 2-(Bromomethyl)prop-1-ene (CAS Number 1458-98-6; 3.1 g, 23.054 mmol) was slowly added to the reaction mixture at −78° C. The resulting reaction mixture was warmed to rt. The resulting reaction mixture was stirred at rt for 1 h. The resulting reaction mixture was poured into saturated aqueous $NH_4Cl$ solution (20 ml) and extracted with EtOAc (3×80 ml). The combined organic phase was collected, dried over $Na_2SO_4$, filtered and concentrated under reduced pressure to get crude material. The resulting residue was purified by column chromatography (6% EtOAc in hexane) yielding 1-(tert-butyl) 3-ethyl 3-(2-methylallyl)pyrrolidine-1,3-dicarboxylate (3.50 g, 11.78 mmol). LCMS: Method 1, 2.63 min, MS: ES+ 298.4.

Step b.

A solution of 1-(tert-butyl) 3-ethyl 3-(2-methylallyl)pyrrolidine-1,3-dicarboxylate (3.50 g, 11.78 mmol) in MeOH: DCM (1:1, 40 ml) was cooled to −78° C. Ozone gas was purged in to the reaction mixture at −78° C. for 1 h. The resulting reaction mixture was purged with nitrogen gas for 10 min. Dimethyl sulfide (2.10 g, 35.35 mmol) was added dropwise to the resulting reaction mixture at −78° C. The resulting reaction mixture was warmed to rt and stirred for 1 h. The reaction mixture was concentrated under vacuum and the resulting residue was purified by column chromatography (18-19% EtOAc in hexane) yielding 1-(tert-butyl) 3-ethyl 3-(2-oxopropyl)pyrrolidine-1,3-dicarboxylate (1.89 g, 6.32 mmol). LCMS: Method 1, 2.06 min, MS: ES+ 300.3.

Step c.

To a solution of 1-(tert-butyl) 3-ethyl 3-(2-oxopropyl) pyrrolidine-1,3-dicarboxylate (0.50 g, 1.67 mmol) in THF: acetic acid (9:1, 10 ml) was added CH$_3$COONH$_4$ (0.64 g, 8.36 mmol) at rt. The resulting reaction mixture was stirred at rt for 10 min. Sodium triacetoxyborohydride (1.06 g, 5.01 mmol) was added to the reaction mixture at rt and the resulting reaction mixture was heated at 70° C. for 20 h. The mixture was combined with two other batches prepared on the same scale by an identical method and was poured into water (80 ml) and neutralized with solid NaHCO$_3$. The mixture was extracted with EtOAc (3×80 ml) and the combined organic phase was collected, dried over Na$_2$SO$_4$, filtered and concentrated under reduced pressure to afford a residue which was purified by column chromatography (85% EtOAc in hexane) yielding tert-butyl 8-methyl-6-oxo-2,7-diazaspiro[4.4]nonane-2-carboxylate (1.0 g, 3.93 mmol). LCMS: Method 1, 1.91 min, MS: ES+255.5.

Step d.

To a solution of tert-butyl 8-methyl-6-oxo-2,7-diazaspiro [4.4]nonane-2-carboxylate (0.4 g, 1.57 mmol) in DCM (5 ml) was added TFA (1.30 ml, 15.74 mmol) at 0° C. The reaction mixture was stirred at rt for 1 h. The resulting reaction mixture was concentrated under reduced pressure. The obtained residue was triturated with diethyl ether (2×10 ml) yielding 3-methyl-2,7-diazaspiro[4.4]nonan-1-one TFA salt (0.40 g, quantitative). This material was directly used for the next step without further purification. LCMS: Method 4, 2.097 min, MS: ES+ 155.0.

Step e.

To a solution of 3-methyl-2,7-diazaspiro[4.4]nonan-1-one TFA salt (0.40 g, 1.49 mmol) in THF (5 ml) was added K$_2$CO$_3$ (0.82 g, 5.97 mmol) to 0° C. The reaction mixture was stirred to 0° C. for 10 min. Cyanogen bromide (0.19 g, 1.79 mmol) was added to the reaction mixture at 0° C. and stirred at 0° C. for a further 30 min. The resulting reaction mixture was filtered and concentrated under reduced pressure yielding title compound (0.50 g, quantitative) as crude material. LCMS: Method 1, 1.51 min, MS: ES+ 180.2. The obtained crude material was subjected for further diastereomeric separation by preparative HPLC; mobile phase: (A) 20 mM Ammonium Acetate in water (B) 100% MeCN: MeOH (50:50), column: X-bridge C18, 150×19 mm, 5 µm, flow rate: 15 ml/min which yielded Example 82 (0.055 g, 0.27 mmol) and Example 83 (0.058 g, 0.32 mmol).

Example 82 8-Methyl-6-oxo-2,7-diazaspiro[4.4] nonane-2-carbonitrile: Diastereomer 1

LCMS: Method 2, 2.383 min, MS: ES+ 179.90; Chiral HPLC: Method 6, RT 8.25 min, 8.42 min, 1H NMR (400 MHz, DMSO-d$_6$) δ ppm: 7.97 (s, 1H), 3.58-3.63 (m, 1H), 3.35-3.54 (m, 3H), 3.25-3.28 (m, 1H), 2.18-2.23 (m, 1H), 1.87-1.90 (m, 2H), 1.54-1.59 (m, 1H), 1.11 (d, J=6.0 Hz, 3H).

Example 83 8-Methyl-6-oxo-2,7-diazaspiro[4.4] nonane-2-carbonitrile: Diastereomer 2

LCMS: Method 2, 2.406 min, MS: ES+ 179.90; Chiral HPLC: Method 6, RT 8.16 min, 8.34 min, 1H NMR (400 MHz, DMSO-d$_6$) δ ppm: 7.99 (s, 1H), 3.52-3.63 (m, 2H), 3.37-3.42 (m, 2H), 3.24-3.26 (m, 1H), 2.22-2.27 (m, 1H), 2.07-2.12 (m, 1H), 1.75-1.78 (m, 1H), 1.50-1.55 (m, 1H), 1.11 (d, J=6.40 Hz, 3H).

Example 84 6-Oxo-8-phenyl-2,7-diazaspiro[4.4] nonane-2-carbonitrile: Diastereomer 1

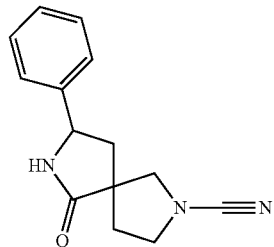 [SMILES: N#CN1CCC2(CC(c3ccccc3)NC2=O)C1]

Synthesised according to Scheme 8. Steps a-e were carried out using a procedure similar to that described for Example 80, using potassium phenyltrifluoroborate in step b. Step f and subsequent diastereomeric separation was carried out using a procedure similar to step e of Examples 82 and 83. Two racemic diastereomers were obtained with LCMS RT Method 2, 3.25 and 3.29 min. One of these showed appropriate biological properties to be included as an example. LCMS: Method 2, 3.29 min, MS: ES+ 242.3; $^1$H NMR (400 MHz, DMSO-d$_6$) δ ppm: 8.45 (s, 1H), 7.27-7.42 (m, 5H), 4.71 (t, J=7.6 Hz, 1H), 3.47-3.57 (m, 2H), 3.35-3.40 (m, 2H), 2.55-2.60 (m, 1H), 2.09-2.17 (m, 1H), 1.77-1.82 (m, 1H), 1.68-1.74 (m, 1H).

Example 85 2-Oxo-1,5-dihydro-2H-spiro[benzo[e] [1,4]oxazepine-3,3'-pyrrolidine]-1'-carbonitrile

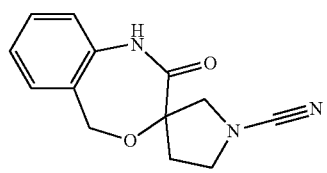 [SMILES: N#CN1CCC2(C1)OCc1ccccc1NC2=O]

Step a.

To a solution of 1-(tert-butyl) 3-methyl 3-hydroxypyrrolidine-1,3-dicarboxylate (Intermediate C, 0.7 g, 2.857 mmol) in DMF (10 ml) were added K$_2$CO$_3$ (1.18 g, 8.571 mmol) and 2-nitrobenzyl bromide (CAS Number 3958-60-9; 0.74 g, 3.428 mmol) at rt. The reaction mixture was stirred at rt for 16 h then poured into water (150 ml) and extracted with EtOAc (3×100 ml). The combined organic phase was separated, dried over Na$_2$SO$_4$, filtered and concentrated under reduced pressure. The resulting residue was purified by flash chromatography (neutral aluminium oxide, 5% EtOAc in hexane) yielding 1-(tert-butyl) 3-methyl 3-((2-nitrobenzyl)oxy)pyrrolidine-1,3-dicarboxylate (0.13 g, 0.342 mmol). LCMS: Method 1, 2.557 min, MS: ES+ 325.5 (M-56); $^1$H NMR (400 MHz, DMSO-d$_6$) δ ppm: 8.04 (d, J=8.0 Hz, 1H), 7.76 (d, J=4.0 Hz, 2H), 7.57-7.60 (m, 1H), 4.78-4.91 (m, 2H), 3.71 (s, 3H), 3.58-3.61 (m, 2H), 3.41-3.48 (m, 1H), 3.33-3.35 (m, 1H), 2.26-2.28 (m, 2H), 1.38 (d, J=13.6 Hz, 9H).

Step b.

To a stirred solution of 1-(tert-butyl) 3-methyl 3-((2-nitrobenzyl)oxy)pyrrolidine-1,3-dicarboxylate (0.12 g, 0.315 mmol) in THF:water (1:1; 6 ml) was added iron powder (0.176 g, 3.158 mmol) and ammonium chloride (0.168 g, 3.158 mmol) at rt. The reaction mixture was heated at 70° C. for 16 h. The resulting reaction mixture was cooled to rt and filtered through celite hyflow. The celite bed was washed with EtOAc (2×10 ml). The combined filtrate was poured into water (50 ml) and extracted with EtOAc (3×50 ml). The combined organic phase was separated, dried over $Na_2SO_4$, filtered and concentrated under reduced pressure yielding 1-(tert-butyl) 3-methyl 3-((2-aminobenzyl)oxy)pyrrolidine-1,3-dicarboxylate (0.1 g, 0.285 mmol). LCMS: Method 1, 2.339 min, MS: ES+ 351.38; $^1$H NMR (400 MHz, DMSO-$d_6$) δ ppm: 6.99-7.03 (m, 2H), 6.63 (d, J=8.0 Hz, 1H), 6.50 (t, J=7.6 Hz, 1H), 5.10 (s, 2H), 4.34-4.38 (m, 1H), 4.24-4.27 (m, 1H), 3.75 (s, 3H), 3.55-3.69 (m, 2H), 3.41-3.46 (m, 1H), 3.29-3.32 (m, 1H), 2.19-2.34 (m, 2H), 1.39 (d, J=4.0 Hz, 9H).

Step c.

To a stirred solution of 1-(tert-butyl) 3-methyl 3-((2-aminobenzyl)oxy)pyrrolidine-1,3-dicarboxylate (0.08 g, 0.228 mmol) in THF (5 ml) was added TBD (0.064 g, 0.457 mmol) at rt. The reaction mixture was heated at 70° C. for 1 h. The resulting reaction mixture was cooled to rt, poured into water (50 ml) and extracted with EtOAc (2×30 ml). The combined organic phase was separated, dried over $Na_2SO_4$, filtered and concentrated under reduced pressure. The resulting crude material was purified by flash chromatography (3% MeOH in DCM) yielding tert-butyl 2-oxo-1,5-dihydro-2H-spiro[benzo[e][1,4]oxazepine-3,3'-pyrrolidine]-1'-carboxylate (0.03 g, 0.094 mmol). LCMS: Method 1, 2.229 min, MS: ES+ 263.13 (M-56); H NMR (400 MHz, DMSO-$d_6$) δ ppm: 10.39 (s, 1H), 7.21-7.28 (m, 2H), 7.12 (d, J=8.0 Hz, 1H), 6.99-7.03 (m, 1H), 4.64 (s, 2H), 3.61-3.67 (m, 1H), 3.43-3.57 (m, 2H), 3.08-3.16 (m, 1H), 2.28-2.33 (m, 1H), 2.14-2.16 (m, 1H), 1.39 (d, J=4.0 Hz, 9H).

Step d.

To a stirred solution of tert-butyl 2-oxo-1,5-dihydro-2H-spiro[benzo[e][1,4]oxazepine-3,3'-pyrrolidine]-1'-carboxylate (0.027 g, 0.085 mmol) in DCM (2 ml) was added TFA (0.13 ml) at 0° C. The reaction mixture was stirred at 0° C. for 30 min. The resulting reaction mixture was concentrated under reduced pressure. The obtained residue was azeotropically distilled with DCM (3×5 ml). The obtained material was triturated with hexane (2×2 ml) and dried under high vacuum yielding 1,5-dihydro-2H-spiro[benzo[e][1,4]oxazepine-3,3'-pyrrolidin]-2-one TFA salt (0.02 g, 0.06 mmol). LCMS: Method 1, 1.365 min, MS: ES+ 219.28; $^1$H NMR (400 MHz, DMSO-$d_6$) δ ppm: 10.59 (s, 1 H), 9.20 (br, s, 2H), 7.26-7.30 (m, 2H), 7.15 (d, J=7.6 Hz, 1H), 7.03-7.05 (m, 1H), 4.62-4.72 (m, 2H), 3.29-3.58 (m, 4H), 2.27-2.39 (m, 2H).

Step e.

To a stirred solution of 1,5-dihydro-2H-spiro[benzo[e][1,4]oxazepine-3,3'-pyrrolidin]-2-one TFA salt (0.02 g, 0.0602 mmol) in THF (5 ml) was added $K_2CO_3$ (41.5 g, 0.301 mmol) at 0° C. Cyanogen bromide (0.0076 g, 0.0723 mmol) was added to the reaction mixture at 0° C. The reaction mixture was stirred at 0° C. for 10 min. The resulting reaction mixture was concentrated under vacuum and the resulting crude material was purified by flash chromatography (2% MeOH in DCM) yielding 2-oxo-1,5-dihydro-2H-spiro[benzo[e][1,4]oxazepine-3,3'-pyrrolidine]-1'-carbonitrile (0.009 g, 0.037 mmol). LCMS: Method 3, 3.414 min, MS: ES+ 244.02; $^1$H NMR (400 MHz, DMSO-$d_6$) δ ppm: 10.48 (s, 1H), 7.24-7.29 (m, 2H), 7.14 (d, J=7.6 Hz, 1H), 7.02 (t, J=8.0 Hz, 1H), 4.64-4.72 (m, 2H), 3.75 (d, J=10.8 Hz, 1H), 3.57-3.68 (m, 2H), 3.43-3.51 (m, 1H), 2.29-2.37 (m, 1H), 2.17-2.23 (m, 1H).

Example 86 2-Oxo-1,2,4,5-tetrahydrospiro[pyrido[2,3-b][1,4]diazepine-3,3'-pyrrolidine]-1'-carbonitrile

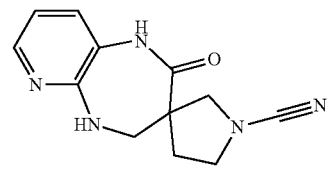 [SMILES: N#CN1CCC2(CNc3ncccc3NC2=O)C1]

Step a.

To a stirred solution of ethyl 2-cyanoacrylate (2.2 g, 17.6 mmol) in DCM (50 ml) were added TFA (0.48 g, 4.224 mmol) and N-benzyl-1-methoxy-N-((trimethylsilyl)methyl)methanamine (CAS Number 93102-05-7; 5.0 g, 21.12 mmol) at 0° C. The reaction mixture was stirred at rt for 16 h. The resulting reaction mixture was cooled to 10° C. and quenched by saturated $NaHCO_3$ solution (100 ml). The obtained mixture was extracted with DCM (3×50 ml). The combined organic phase was washed with water (50 ml). The obtained organic phase was dried over $Na_2SO_4$, filtered and concentrated under reduced pressure. The resulting residue was purified by column chromatography (3% EtOAc in hexane) yielding ethyl 1-benzyl-3-cyanopyrrolidine-3-carboxylate (2.4 g, 9.302 mmol). LCMS: Method 1, 1.714 min, MS: ES+ 258.8; $^1$H NMR (400 MHz, DMSO-$d_6$) δ ppm: 7.25-7.36 (m, 5H), 4.22 (q, J=7.2 Hz, 2H), 3.67 (dd, J=13.2 Hz, 18.0 Hz, 2H), 3.14 (d, J=9.6 Hz, 1H), 2.88 (d, J=10.0 Hz, 1H), 2.81-2.85 (m, 1H), 2.53-2.57 (m, 1H), 2.44-2.47 (m, 1H), 2.33-2.40 (m, 1H), 1.23 (t, J=7.2 Hz, 3H).

Step b.

To a stirred solution of ethyl 1-benzyl-3-cyanopyrrolidine-3-carboxylate (2.4 g, 9.298 mmol) in MeOH (25 ml) was carefully added Raney nickel (50% in water) (4.8 g, 2.0 vol. w/w) at rt in an autoclave. The reaction mixture was stirred at rt under 250 psi hydrogen pressure for 48 h. The reaction mixture was carefully filtered through a celite bed, washed with MeOH (20 ml) and the filtrate was concentrated under vacuum yielding a mixture (44:56 by LCMS analysis) of methyl 3-(aminomethyl)-1-benzylpyrrolidine-3-carboxylate and ethyl 3-(aminomethyl)-1-benzylpyrrolidine-3-carboxylate (2.2 g). LCMS: Method 4, 3.825 min, 4.133, MS: ES+ 249.01, 262.97. The obtained mixture was directly used for next step without further purification.

Step c.

To a stirred solution of a mixture of methyl 3-(aminomethyl)-1-benzylpyrrolidine-3-carboxylate and ethyl 3-(aminomethyl)-1-benzylpyrrolidine-3-carboxylate (2.2 g, 8.396 mmol) in toluene (15 ml) were added 2-fluoro-3-nitro pyridine (1.3 g, 9.236 mmol) and $K_2CO_3$ (1.74 g, 12.595 mmol) at rt. The reaction mixture was heated at 120° C. for 16 h. The reaction mixture was cooled to rt, poured into water (150 ml) and extracted with EtOAc (3×100 ml). The combined organic phase was washed with water (100 ml). The organic phase was separated, dried over $Na_2SO_4$, filtered and concentrated under reduced pressure. The resulting residue was purified by flash chromatography (15% EtOAc in hexane) yielding a mixture of methyl 1-benzyl-3-(((3- nitropyridin-2-yl)amino)methyl)pyrrolidine-3-carboxylate and ethyl 1-benzyl-3-(((3-nitropyridin-2-yl)amino)methyl) pyrrolidine-3-carboxylate (1.6 g). LCMS: Method 1, 1.782 min, 1.865 min, MS: ES+ 371.18, 385.18.

Step d.

To a stirred solution of a mixture of methyl 1-benzyl-3-(((3-nitropyridin-2-yl)amino)methyl)-pyrrolidine-3-carboxylate and ethyl 1-benzyl-3-(((3-nitropyridin-2-yl)amino)methyl)-pyrrolidine-3-carboxylate (1.6 g) in MeOH (25 ml) was carefully added Raney nickel (50% in water) (3.2 g, 2.0 vol. w/w) at rt. The reaction mixture was purged with hydrogen gas at rt for 2 h. The reaction mixture was carefully filtered through a celite bed, washed with MeOH (15 ml) and the filtrate was concentrated under vacuum yielding a mixture of methyl 3-(((3-aminopyridin-2-yl) amino)methyl)-1-benzylpyrrolidine-3-carboxylate and ethyl 3-(((3-aminopyridin-2-yl)amino)methyl)-1-benzylpyrrolidine-3-carboxylate (1.44 g). LCMS: Method 1, 1.434 min, 1.537 min, MS: ES+ 341.33, 355.34.

Step e.

A solution of a mixture of methyl 3-(((3-aminopyridin-2-yl)amino)methyl)-1-benzyl-pyrrolidine-3-carboxylate and ethyl 3-(((3-aminopyridin-2-yl)amino)methyl)-1-benzyl-pyrrolidine-3-carboxylate (1.4 g) in acetic acid (20 ml) was heated at 120° C. for 2 h. The reaction mixture was cooled to rt, poured into saturated NaHCO$_3$ solution (250 ml) and extracted with EtOAc (3×50 ml). The combined organic phase was separated and washed with DM water (50 ml). The organic phase was separated, dried over Na$_2$SO$_4$, filtered and concentrated under reduced pressure. The resulting residue was purified by column chromatography (0.5% MeOH in DCM) yielding 1'-benzyl-4,5-dihydrospiro[pyrido [2,3-b][1,4]diazepine-3,3'-pyrrolidin]-2(1H)-one (0.313 g, 1.016 mmol). LCMS: Method 1, 1.271 min, MS: ES+ 309.13; $^1$H NMR (400 MHz, DMSO-d$_6$) δ ppm: 9.57 (s, 1H), 7.69 (dd, J=1.2 Hz, 4.4 Hz, 1H), 7.29-7.31 (m, 4H), 7.23-7.24 (m, 1H), 7.19 (d, J=7.2 Hz, 1H), 6.83-6.88 (m, 1H), 6.53-6.56 (m, 1H), 3.51-3.60 (m, 2H), 3.28 (t, J=4.8 Hz, 2H), 2.73 (d, J=9.6 Hz, 1H), 2.55-2.60 (m, 2H), 2.38-2.42 (m, 1H), 2.03-2.10 (m, 1H), 1.67-1.72 (m, 1H).

Step f.

To a stirred solution of 1'-benzyl-4,5-dihydrospiro[pyrido [2,3-b][1,4]diazepine-3,3'-pyrrolidin]-2(1H)-one (0.31 g, 1.006 mmol) in THF (5 ml) were added K$_2$CO$_3$ (0.278 g, 2.012 mmol) and cyanogen bromide (0.107 g, 1.006 mmol) at 0° C. The reaction mixture was stirred at rt for 36 h. The resulting reaction mixture was poured into water (50 ml) and extracted with DCM (3×25 ml). The combined organic phase was separated and washed with water (50 ml). The organic phase was separated, dried over Na$_2$SO$_4$, filtered and concentrated under reduced pressure. The resulting residue was purified by flash chromatography (0.5% MeOH in DCM) yielded 2-oxo-1,2,4,5-tetrahydrospiro[pyrido[2,3-b][1,4]diazepine-3,3'-pyrrolidine]-1'-carbonitrile (0.245 g, quantitative). The obtained crude material was subjected to preparative HPLC purification; mobile phase: (A) 100% water and (B) 100% MeCN, column: Waters X Bridge C18 250×19 mm, 5 micron, flow rate 11.0 ml/min yielded 2-oxo-1,2,4,5-tetrahydrospiro[pyrido[2,3-b][1,4]diazepine-3,3'-pyrrolidine]-1'-carbonitrile (0.077 g, 0.317 mmol). LCMS: Method 4, 2.939 min, MS: ES+ 243.99; $^1$H NMR (400 MHz, DMSO-d$_6$) δ ppm: 9.85 (s, 1H), 7.75 (dd, J=1.6 Hz, 4.8 Hz, 1H), 7.28 (d, J=7.6 Hz, 1H), 6.89 (t, 4.8 Hz, 1H), 6.61 (dd, J=4.4 Hz, 7.6 Hz, 1H), 3.69 (d, J=10.0 Hz, 1H), 3.48 (t, J=7.2 Hz, 2H), 3.35-3.36 (m, 1H), 3.30-3.31 (m, 1H), 3.20-3.24 (m, 1H), 2.09-2.16 (m, 1H), 1.88-1.95 (m, 1H).

Example 87 8-Methyl-7,10-dioxo-8-phenyl-2,6,9-triazaspiro[4.5]decane-2-carbonitrile

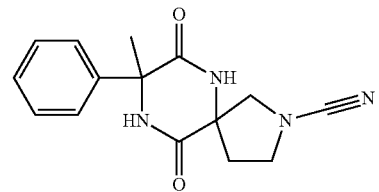 [SMILES: CC1(c2ccccc2)NC(=O)C2(CCN(C#N)C2)NC1=O]

Step a.

To a stirred solution of 2-amino-2-phenylpropanoic acid (CAS Number 565-07-1; 4.0 g, 24.21 mmol) in MeCN (50 ml) was added tetramethylammonium hydroxide 10% in water solution (21.8 ml, 24.21 mmol) at rt. Boc anhydride (7.92 g, 36.0 mmol) was added to the reaction mixture at rt. The reaction mixture was stirred at rt for 48 h. The resulting reaction mixture was poured into water (200 ml) and washed with diethyl ether (3×25 ml). The aqueous layer was acidified with 5% citric acid solution (~70 ml) and extracted with EtOAc (3×30 ml). The combined organic phase was separated, dried over Na$_2$SO$_4$, filtered and concentrated under reduced pressure yielding 2-((tert-butoxycarbonyl)amino)-2-phenylpropanoic acid (4.2 g, 15.84 mmol). LCMS: Method 1, 2.162 min, MS: ES+ 264.28; $^1$H NMR (400 MHz, DMSO-d6) δ ppm: 12.74 (s, 1H), 7.43 (d, J=8.0 Hz, 2H), 7.33 (t, J=7.2 Hz, 2H), 7.26 (t, J=7.2 Hz, 1H), 7.14 (br s, 1H), 1.72 (s, 3H), 1.36 (s, 9H). This material was used directly for the next step without further purification.

Step b.

To a solution of methyl 2-((tert-butoxycarbonyl)amino)-2-phenylpropanoic acid (1.13 g, 4.27 mmol) in dry THF (10 ml) were added HATU (4.86 g, 12.81 mmol) and DIPEA (2.2 ml, 12.81 mmol) at 0° C. The reaction mixture was stirred at 0° C. for 30 min. Methyl 3-amino-1-benzylpyrrolidine-3-carboxylate (Intermediate A; 1 g, 4.27 mmol) was added to the reaction mixture at 0° C. The resulting reaction mixture was stirred at rt for 16 h. The resulting reaction mixture was poured into water (20 ml) and extracted with DCM (6×20 ml). The combined organic phase was dried over Na$_2$SO$_4$, filtered and concentrated under reduced pressure. The obtained residue was purified by column chromatography (50-60% EtOAc in hexane) yielding methyl 1-benzyl-3-(2-((tert-butoxycarbonyl)amino)-2-phenylpropanamido)pyrrolidine-3-carboxylate (2.59 g, quantitative). LCMS: Method 1, 2.015 min, MS: ES+ 482.28.

Step c.

To a stirred solution of methyl 1-benzyl-3-(2-((tert-butoxycarbonyl)amino)-2-phenylpropanamido)pyrrolidine-3-carboxylate (1.2 g, 2.49 mmol) in DCM (5 ml) was added TFA (12 ml) at 0° C. The reaction mixture was stirred at rt for 3 h. The resulting reaction mixture was concentrated under vacuum. The obtained residue was triturated with n-pentane (3×10 ml) and dried under high vacuum. The resulting crude material was quickly poured into saturated NaHCO$_3$ solution and stirred well until pH 7-8. The resulting mixture was extracted with a mixture of MeOH:DCM (1:9, 5×15 ml). The combined organic phase was dried over Na$_2$SO$_4$, filtered and concentrated under reduced pressure yielding methyl 3-(2-amino-2-phenylpropanamido)-1-benzylpyrrolidine-3-carboxylate (0.776 g, 2.036 mmol). LCMS:

Method 3, 4.167 min, MS: ES+ 382.05. This material was used directly for the next step without further purification.

Step d.

To a solution of methyl 3-(2-amino-2-phenylpropanamido)-1-benzylpyrrolidine-3-carboxylate (0.776 g, 2.036 mmol) in dry THF (10 ml) was added TBD (0.708 g, 5.09 mmol) at rt. The reaction mixture was stirred at rt for 12 h. The resulting reaction mixture was poured into water (20 ml) and extracted with EtOAc (3×40 ml). The combined organic phase was dried over $Na_2SO_4$, filtered and concentrated under reduced pressure. The resulting residue was triturated with diethyl ether (2×15 ml) and dried under vacuum yielding 2-benzyl-8-methyl-8-phenyl-2,6,9-triazaspiro[4.5]decane-7,10-dione (0.380 g, 1.08 mmol). LCMS: Method 1, 1.586 min, MS: ES+ 350.48. This material was used directly for the next step without further purification.

Step e.

To a stirred solution of 2-benzyl-8-methyl-8-phenyl-2,6,9-triazaspiro[4.5]decane-7,10-dione (0.380 g, 1.08 mmol) in MeOH (15 ml) was added acetic acid (2 ml) at rt. Pd/C (50% moisture) (65 mg) was added to the reaction mixture at rt. The reaction mixture was purged with $H_2$ for 1.5 h at rt. The reaction mixture was carefully filtered through celite hyflow. The celite bed was washed with MeOH (2×5 ml). The combined filtrate was concentrated under vacuum. The obtained residue was triturated with diethyl ether (2×10 ml) and dried under high vacuum yielding 8-methyl-8-phenyl-2,6,9-triazaspiro[4.5]decane-7,10-dione (0.384 g, 1.203 mmol). LCMS: Method 3, 2.338, 2.551 min, MS: ES+ 259.98. This material was used directly for the next step without further purification.

Step f.

To a stirred solution of 8-methyl-8-phenyl-2,6,9-triazaspiro[4.5]decane-7,10-dione (0.384 g, 1.482 mmol) in THF:DMF (2:1, 8 ml) was added $K_2CO_3$ (0.519 g, 3.764 mmol) at rt. The reaction mixture was stirred at rt for 15 min. Cyanogen bromide (0.159 g, 1.504 mmol) was added to the reaction mixture. The reaction mixture was stirred at rt for 45 min. The resulting reaction mixture was poured into ice cold water (30 ml). The obtained precipitates were filtered under vacuum, washed with water (20 ml) and air dried. The obtained solid material was triturated with diethyl ether (3×10 ml) and dried under high vacuum yielding 8-methyl-7,10-dioxo-8-phenyl-2,6,9-triazaspiro[4.5]decane-2-carbonitrile (0.148 g, 0.520 mmol). LCMS: Method 2, 2.820, 2.907 min, MS: ES+ 285.24, 285.29; H NMR (400 MHz, DMSO-d6) δ ppm: 9.18 (s, 1H), 8.77 (s, 1H), 7.40-7.43 (m, 5H), 3.61-3.63 (m, 1H), 3.33-3.51 (m, 2H), 3.17-3.18 (m, 1H), 1.97-2.01 (m, 1H), 1.81-1.85 (m, 1H), 1.60 (s, 3H).

Biological Activity of Compounds of the Invention

ABBREVIATIONS

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
DMSO dimethyl sulfoxide In Vitro Cezanne 1 Inhibition Assay
Expression and Purification of Cezanne 1

The Cezanne 1 construct was PCR amplified and cloned into a pFLAG-CMV-6c vector (Sigma-Aldrich) with an N-terminal FLAG tag. HEK293T cells were transfected with FLAG-Cezanne 1 using TransIT-LT1 transfection reagent (Mirus) according to the manufacturer's instructions. Cells were harvested 48 hours after transfection. Cells were washed once with PBS and scraped in lysis buffer (50 mM Tris, pH 7.5, 150 mM NaCl, 3 mM EDTA, 0.5% NP40, 10% glycerol, 5 mM beta-mercaptoethanol, protease inhibitors (complete mini, Roche) and phosphatase inhibitors (PhosSTOP mini, Roche). Lysates were incubated for 30 min on ice and centrifuged at 4000 rpm for 10 min at 4° C. Soluble supernatant was added to FLAG affinity resin (EZview Red ANTI-FLAG M2 affinity gel, Sigma-Aldrich) equilibrated in low salt buffer (20 mM Tris, pH 7.5, 150 mM NaCl, 0.5 mM EDTA, 5 mM beta-mercaptoethanol) and incubated at 4° C. for 3 hours rotating. The resin was spun at 2000 rpm for 2 min and the supernatant was removed. The resin was washed two times with low salt buffer and one time with high salt buffer (20 mM Tris, pH 7.5, 500 mM NaCl, 0.5 mM EDTA, 5 mM beta-mercaptoethanol, protease inhibitors (complete mini, Roche) and phosphatase inhibitors (PhosSTOP mini, Roche). To elute the bound Cezanne 1, elution buffer (10 mM Tris, pH 7.5, 150 mM NaCl, 0.5 mM EDTA, 10% glycerol, 0.5% NP40, 5 mM beta-mercaptoethanol, 0.15 mg/ml 3× FLAG peptide (Sigma-Aldrich)) was added to the resin and incubated at 4° C. for 2.5 hours while rotating. The resin was centrifuged at 4000 rpm for 30 seconds, and the supernatant containing purified FLAG-Cezanne 1 was removed and stored at −80° C.

The purified FLAG-protein was characterised for molecular weight (left hand scale is in kDaltons) against BSA using SDS-PAGE as shown in FIG. 1.

Cezanne 1 Biochemical Kinetic Assay.

Reactions were performed in duplicate in black 384 well plates (small volume, Greiner 784076) in a final reaction volume of 21 μl. Cezanne 1 was diluted in reaction buffer (40 mM Tris, pH 7.5, 0.005% Tween 20, 0.5 mg/ml BSA, 5 mM—beta-mercaptoethanol) to the equivalent of 0, 0.001, 0.050, 0.01 and 0.05 l/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm. FIG. 2 shows a graph of the proteolytic activity of Cezanne 1 measured using a fluorescence polarisation assay. Various volumes of purified Cezanne 1 as indicated were incubated with a TAMRA labelled peptide linked to ubiquitin via an isopeptide bond.

Cezanne 1 Biochemical $IC_{50}$ Assay

Dilution plates were prepared at 21 times the final concentration (2100 μM for a final concentration of 100 μM) in 50% DMSO in a 96-well polypropylene V-bottom plate (Greiner #651201). A typical 8-point dilution series to be 100, 30, 10, 3, 1, 0.3, 0.1, 0.03 μM final. Reactions were performed in duplicate in black 384 well plates (small volume, Greiner 784076) in a final reaction volume of 21 μl. Either 1 μl of 50% DMSO or diluted compound was added to the plate. Cezanne 1 was diluted in reaction buffer (40 mM Tris, pH 7.5, 0.005% Tween 20, 0.5 mg/ml BSA, 5 mM—beta-mercaptoethanol) to the equivalent of 0.005 μl/well and 10 μl of diluted Cezanne 1 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in Cezanne 1 biochemical IC50 assay.

Ranges:
A<0.1 μM;
0.1<B<1 μM;
1<C<10 μM;
D>10 μM

| Example | IC50 range |
| --- | --- |
| 1 | C |
| 2 | C |
| 3 | C |
| 4 | C |
| 5 | C |
| 6 | C |
| 7 | C |
| 8 | C |
| 9 | C |
| 10 | C |
| 11 | C |
| 12 | C |
| 13 | C |
| 14 | C |
| 15 | C |
| 16 | B |
| 17 | C |
| 18 | B |
| 19 | B |
| 20 | C |
| 21 | B |
| 22 | B |
| 23 | B |
| 24 | A |
| 25 | B |
| 26 | B |
| 27 | C |
| 28 | B |
| 29 | C |
| 30 | B |
| 31 | C |
| 32 | C |
| 33 | C |
| 34 | C |
| 35 | C |
| 36 | B |
| 37 | C |
| 38 | C |
| 39 | C |
| 40 | B |
| 41 | B |
| 42 | B |
| 43 | B |
| 44 | B |
| 45 | B |
| 46 | C |
| 47 | C |
| 48 | B |
| 49 | B |
| 50 | B |
| 51 | B |
| 52 | B |
| 53 | B |
| 54 | B |
| 55 | C |
| 56 | C |
| 57 | B |
| 58 | B |
| 59 | B |
| 60 | B |
| 61 | C |
| 62 | D |
| 63 | C |
| 64 | B |
| 65 | C |
| 66 | B |
| 67 | B |
| 68 | B |
| 69 | B |
| 70 | B |
| 71 | B |
| 72 | B |
| 73 | B |
| 74 | B |
| 75 | B |
| 76 | C |
| 77 | C |
| 78 | C |
| 79 | C |
| 80 | D |
| 81 | C |
| 82 | D |
| 83 | D |
| 84 | D |
| 85 | C |
| 86 | B |
| 87 | B |
| 88 | C |
| 89 | C |
| 90 | B |
| 91 | C |
| 92 | C |
| 93 | B |
| 94 | B |
| 95 | B |
| 96 | C |
| 97 | B |
| 98 | B |
| 99 | C |
| 100 | B |
| 101 | B |
| 102 | C |
| 103 | B |
| 104 | B |
| 105 | B |
| 106 | C |
| 107 | B |
| 108 | B |
| 109 | B |
| 110 | B |
| 111 | B |
| 112 | B |
| 113 | B |
| 114 | B |
| 115 | B |
| 116 | B |
| 117 | B |
| 118 | B |
| 119 | B |
| 120 | B |
| 121 | B |
| 122 | C |
| 123 | B |
| 124 | B |
| 125 | B |
| 126 | B |
| 127 | B |
| 128 | B |
| 129 | B |
| 130 | B |
| 131 | B |
| 132 | B |
| 133 | B |
| 134 | B |
| 135 | A |
| 136 | A |
| 137 | A |
| 138 | B |
| 139 | B |
| 140 | B |
| 141 | C |
| 142 | C |
| 143 | B |
| 144 | B |

-continued

| Example | IC50 range |
| --- | --- |
| 145 | A |
| 146 | B |
| 147 | C |

The invention claimed is:
1. A compound of formula I:

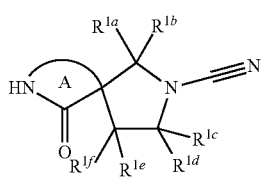

a tautomer thereof, or a pharmaceutically acceptable salt of said compound or tautomer, wherein:
$R^{1a}$, $R^{1b}$, $R^{1c}$ and $R^{1d}$ each independently represent hydrogen or $C_1$-$C_6$ alkyl;
$R^{1e}$ and $R^{1f}$ each independently represent hydrogen or $C_1$-$C_6$ alkyl;
ring A is a 9, 10 or 11-membered fused bicyclic heterocyclyl ring, which in addition to the amide nitrogen optionally comprises 1, 2 or 3 heteroatoms each independently selected from N, O and S; wherein the ring fused to the amide-containing ring is aromatic; and which may be optionally substituted with one -$Q^1$-($R^2$)$_n$, wherein n is 1; and optionally one, two or three -$Q^1$-($R^2$)$_n$, wherein n is 0; wherein each -$Q^1$-($R^2$)$_n$, is the same or different;
when n is 0, $Q^1$ represents halogen, cyano, oxo, hydroxyl, —$NR^3R^4$, —$CONR^3R^4$, —$NR^3COR^4$, —$NR^3CONR^4R^{4a}$, —$COR^3$, —C(O)O$R^3$, $C_1$-$C_6$ alkyl, or $C_1$-$C_6$ alkoxy; wherein the alkyl and alkoxy groups are optionally substituted with one to four halogen substituents;
when n is 1, $Q^1$ represents a covalent bond, an oxygen atom, a sulphur atom, —SO—, —SO$_2$—, —CO—, —C(O)O—, —CONR$^3$—, —NR$^3$—, —NR$^3$CO—, —NR$^3$CONR$^4$—, —SO$_2$NR$^3$—, —NR$^3$SO$^2$—, —NR$^3$SO$_2$NR$^4$—, —NR$^3$C(O)O—, —NR$^3$C(O)OR$^5$—, $C_1$-$C_6$ alkylene, or $C_2$-$C_6$ alkenylene;
$R^2$ represents a phenyl ring or a 5 to 10-membered heterocyclyl or heteroaryl ring, wherein said heterocyclyl and heteroaryl rings comprise 1, 2 or 3 heteroatoms, each independently selected from N, O and S;
wherein said $R^2$ ring is optionally substituted with one to two substituents independently selected from halogen, cyano, oxo, hydroxyl, —NR$^6$R$^7$, —CONR$^6$R$^7$, —NR$^6$COR$^7$, —NR$^6$CONR$^7$R$^{7a}$, —COR$^6$, —C(O)OR$^6$, —$C_1$-$C_6$ alkyl, —$C_1$-$C_6$ alkoxy, -$Q^{2a}$-$R^8$, -$Q^{2b}$-CONR$^6$-$Q^{2c}$-$R^8$, and -$Q^2$-NR$^6$SO$_2$-$Q^{2c}$-$R^8$; wherein the alkyl and alkoxy groups are optionally substituted with one to four substituents selected from halogen and hydroxyl;
$Q^{2a}$ represents a covalent bond, an oxygen atom, a sulphur atom, —SO—, —SO$_2$—, —CO—, or $C_1$-$C_6$ alkylene;
$Q^{2b}$ and $Q^{2c}$ each represent a covalent bond;
$R^3$, $R^4$ and $R^{4a}$ each independently represent hydrogen or $C_1$-$C_6$ alkyl;
$R^6$, $R^7$ and $R^{7a}$ each independently represent hydrogen or $C_1$-$C_6$ alkyl; and $R^8$ is selected from phenyl, piperazinyl, cyclopropyl, morpholinyl and piperidinyl; wherein $R^8$ is optionally substituted by fluorine, chlorine, oxo, cyano, $C_1$-$C_3$ alkyl, or $C_1$-$C_3$ alkoxy.

2. The compound according to claim 1, wherein ring A is selected from indoline-2-one, 3,4-dihydroquinolin-2(1H)-one, 1H-pyrido[2,3-b][1,4]oxazin-2(3H)-one, 3,4-dihydropyrido[2,3-b]pyrazine-2(1H)-one, 1,5-dihydrobenzo[e][1,4]oxazepin-2(3H)-one, 3,4-dihydro-1,5-naphthyridin-2(1H)-one, 3,4-dihydro-1,6-naphthyridin-2(1H)-one, 3,4-dihydro-1,7-naphthyridin-2(1H)-one, 3,4-dihydro-1,8-naphthyridin-2(1H)-one, 3,4-dihydropyrazino[2,3-b]pyrazine-2(1H)-one and 1,2,3,5-tetrahydro-4H-pyrido[2,3-b][1,4]diazepin-4-one.

3. The compound according to claim 1, wherein n is 1; and $Q^1$ is selected from a covalent bond and $C_1$-$C_3$ alkylene.

4. The compound according to claim 1, wherein $R^2$ is phenyl or a 5 or 6-membered monocyclic, or a 9 or 10-membered bicyclic, optionally substituted, heterocyclyl or, heteroaryl ring.

5. The compound according to claim 4, wherein $R^2$ is selected from optionally substituted, piperidinyl, pyrrolyl, phenyl, pyrazolyl, isoxazolyl, indazolyl, pyridinyl, dihydropyridinyl, benzothiazolyl and pyrimidinyl.

6. The compound according to claim 1, wherein $R^2$ is unsubstituted, or substituted with one or two substituents selected from halogen, cyano, oxo, $C_1$-$C_3$ alkyl, $C_1$-$C_3$ alkoxy, —CONR$^6$R$^7$, —NR$^6$COR$^7$, -$Q^{2a}$-$R^8$, and -$Q^{2b}$-NR$^6$SO$_2$-$Q^{2c}$-$R^8$; wherein
alkyl and alkoxy are optionally substituted with fluorine;
$Q^{2a}$ is a covalent bond, an oxygen atom, —CO—, —SO$_2$— or —$C_1$-$C_3$ alkylene;
$R^6$ and $R^7$ are each independently selected from hydrogen and $C_1$-$C_3$ alkyl.

7. The compound according to claim 1, wherein n is 0; $Q^1$ is selected from oxo, methyl, ethyl, $CF_3$, methoxy, halogen and —C(O)NR$^3$R$^4$; and $R^3$ and $R^4$ are each independently selected from hydrogen and methyl.

8. The compound according to claim 1, wherein $R^{1a}$, $R^{1b}$, $R^{1c}$, $R^{1d}$, $R^{1f}$ and $R^{1e}$ are each hydrogen.

9. The compound according to claim 1 selected from the group consisting of:
2'-oxo-1',4'-dihydro-2'H-spiro[pyrrolidine-3,3'-quinoline]-1-carbonitrile;
7'-chloro-2'-oxo-1',4'-dihydro-2'H-spiro[pyrrolidine-3,3'-quinoline]-1-carbonitrile;
7'-methoxy-2'-oxo-1',4'-dihydro-2'H-spiro[pyrrolidine-3,3'-quinoline]-1-carbonitrile;
7'-(5-isopropyl-2-methoxyphenyl)-2-oxo-1',4'-dihydro-2'H-spiro[pyrrolidine-3,3'-quinoline]-1 carbonitrile;
7'-([1,1'-biphenyl]-4-yl)-2'-oxo-1',4'-dihydro-2'H-spiro[pyrrolidine-3,3'-quinoline]-1-carbonitrile;
7-(4-(benzyloxy)phenyl)-2'-oxo-1',4'-dihydro-2'H-spiro[pyrrolidine-3,3-quinoline]-1-carbonitrile;
7'-(2-fluoro-5-methylphenyl)-2'-oxo-1',4'-dihydro-2'H-spiro[pyrrolidine-3,3'-quinoline]-1-carbonitrile;
7'-(3-cyanophenyl)-2'-oxo-1,4'-dihydro-2H-spiro[pyrrolidine-3,3-quinoline]-1-carbonitrile;
7'-(1-methyl-1H-pyrazol-5-yl)-2'-oxo-1',4'-dihydro-2'H-spiro[pyrrolidine-3,3-quinoline]-1-carbonitrile;
2'-oxo-7'-(4-phenoxyphenyl)-1',4'-dihydro-2'1H-spiro[pyrrolidine-3,3'-quinoline]-1-carbonitrile;
7'-(1-methyl-1H-pyrazol-4-yl)-2'-oxo-1',4'-dihydro-2'H-spiro[pyrolidine-3,3'-quinoline]-1-carbonitrile;
7'-(4-cyanophenyl)-2-oxo-1',4'-dihydro-2'H-spiro[pyrrolidine-3,3'-quinoline]-1-carbonitrile;

'-(2-chloro-5-(trifluoro methoxy)phenyl)-2'-oxo-1',4'-dihydro-2'H-spiro[pyrrolidine-3,3'-quinoline]-1-carbonitrile;

5-(1-cyano-2'-oxo-1',4'-dihydro-2'H-spiro[pyrrolidine-3,3'-quinolin]-7'-yl)-N-methylpicolinamide;

7'-(2-(benzyloxy)phenyl)-2'-oxo-1',4'-dihydro-2'H-spiro[pyrrolidine-3,3'-quinoline]-1-carbonitrile;

4-(1-cyano-2'-oxo-1',4'-dihydro-2'H-spiro[pyrrolidine-3,3-quinolin]-7'-yl)-N-methylbenzamide;

7'-(3-((2-chlorobenzyl)oxy)phenyl)-2'-oxo-1',4'-dihydro-2'H-spiro[pyrrolidine-3,3'-quinoline]-1-carbonitrile;

7'-(4-(4-methylpiperazin-1-yl)phenyl)-2'-oxo-1',4'-dihydro-2'H-spiro[pyrrolidine-3,3-quinoline]-1-carbonitrile;

7'-(6-methoxypyridin-3-yl)-2'-oxo-1',4'-dihydro-2'H-spiro[pyrrolidine-33-q oline]-1-carbonitrile;

7'-(5-fluoro-2-isopropoxyphenyl)-2'-oxo-1',4'-dihydro-2'H-spiro[pyrrolidine-3,3'-quinoline]-1-carbonitrile;

7'-(3-methyl-1H-indazol-6-yl)-2'-oxo-1',4'-dihydro-2'H-spiro[pyrrolidine-3,3'-quinoline]-1-carbonitrile;

7'-(4-(4-methylpiperazine-1-carbonyl)phenyl)-2'-oxo-1',4'-dihydro-2'H-spiro[pyrrolidine-3,3'-quinoline]-1-carbonitrile;

7'-(1-methyl-1H-indazol-5-yl)-2'-oxo-1',4'-dihydro-2'H-spiro[pyrrolidine-3,3'-quinoline]-1-carbonitrile;

7'-(5-methyl-1H-indazol-4-yl)-2'-oxo-1',4'-dihydro-2'I-spiro[pyrrolidine-3,3'-quinoline]-1-carbonitrile;

N-(3-(1-cyano-2'-oxo-1',4'-dihydro-2'H-spiro[pyrrolidine-3,3'-quinolin]-7'-yl)phenyl)cyclopropanesulfonamide;

7'-(3-methyl-1H-pyrazol-4-yl)-2'-oxo-1',4'-dihydro-2'H-spiro[pyrrolidine-3,3'-quinoline]-1-carbonitrile;

2'-oxo-7'-(pyrimidin-5-yl)-1',4'-dihydro-2'H-spiro[pyrolidine-3,3'-quinoline]-1-carbonitrile;

N-(3-(1-cyano-2'-oxo-1',4'-dihydro-2'H-spiro[pyrrolidine-3,3-quinolin]-7'-yl)phenyl)acetamide;

3-(1-cyano-2'-oxo-1',4'-dihydro-2'H-spiro[pyrrolidine-3,3'-quinolin]-7'-yl)-N,N-dimethylbenzamide;

N-(4-(1-cyano-2'-oxo-1',4'-dihydro-2'1H-spiro[pyrrolidine-3,3'-quinolin]-7'-yl)phenyl)acetamide;

7'-(4-(morpholinosulfonyl)phenyl)-2'-oxo-1',4'-dihydro-2'H-spiro[pyrrolidine-3,3'-quinoline]-1-carbonitrile;

7'-(3,5-dimethyl-1H-pyrazol-4-yl)-2'-oxo-1',4'-dihydro-2'H-spiro[pyrrolidine-3,3-quinoline]-1-carbonitrile;

7'-(2-methylpyridin-4-yl)-2'-oxo-1',4'-dihydro-2'H-spiro[pyrrolidine-3,3'-quinoline]-1-carbonitrile;

2'-oxo-7'-(3-(piperidin-1-yl)phenyl)-1',4'-dihydro-2'H-spiro[pyrrolidine-3,3'-quinoline]-1-carbonitrile;

N-(2-(1-cyano-2'-oxo-1',4'-dihydro-2'H-spiro[pyrrolidine-3,3'-quinoline]-7'-yl)phenyl)acetamide;

7'-(4-(morpholine-4-carbonyl)phenyl)-2'-oxo-1',4'-dihydro-2'H-spiro[pyrrolidine-3,3'-quinoline]-1-carbonitrile;

7'-(3-(3-(morpholinosulfonyl)phenyl)-2'-oxo-1',4'-dihydro-2'H-spiro[pyrrolidine-3,3'-quinoline]-1-carbonitrile;

7'-(1-methyl-6-oxo-1,6-dihydropyridin-3-yl)-2'-oxo-1',4'-dihydro-2'-spiro[pyrrolidine-3,3'-quinoline]-1-carbonitrile;

7'-(2-methylbenzo[d]thiazol-5-yl)-2'-oxo-1',4'-dihydro-2'H-spiro[pyrrolidine-3,3'-quinoline]-1-carbonitrile;

2'-oxo-6'-phenyl-1',4'-dihydro-2'H-spiro[pyrrolidine-3,3'-quinoline]-1-carbonitrile;

6'-(4-cyanophenyl)-2'-oxo-1',4'-dihydro-2'H-spiro[pyrrolidine-3,3'-quinoline]-1-carbonitrile;

6'-(3-cyanophenyl)-2'-oxo-1',4'-dihydro-2'H-spiro[pyrrolidine-3,3'-quinoline]-carbonitrile;

6'-(4-fluorophenyl)-2'-oxo-1',4'-dihydro-2'H-spiro[pyrrolidine-3,3'-quinoline]-1-carbonitrile;

6'-(3-fluorophenyl)-2'-oxo-1',4'-dihydro-2'H-spiro[pyrrolidine-3,3'-quinoline]-1-carbonitrile;

1-cyano-N,N-dimethyl-2'-oxo-1',4'-dihydro-2'I-spiro[pyrrolidine-3,3'-quinoline]-7'-carboxamide;

1-cyano-N-methyl-2'-oxo-1',4'-dihydro-2'H-spiro[pyrrolidine-3,3'-quinoline]-7'-carboxamide;

2-oxo-1,2-dihydrospiro[pyrido[2,3-b][1,4]oxazine-3,3'-pyrrolidine]-1'-carbonitrile;

2-oxo-7-phenyl 1,2-dihydrospiro[pyrido[2,3-b][1,4]oxazine-3,3'-pyrrolidine]-1'-carbonitrile;

7-(4-cyanophenyl)-2-oxo-1,2-dihydrospiro[pyrido[2,3-b][1,4]oxazine-3,3-pyrrolidine]-1'-carbonitrile;

7-(3-cyanophenyl)-2-oxo-1,2-dihydrospiro[pyrido[2,3-b][1,4]oxazine-3,3'-pyrrolidine]-1'-carbonitrile;

7-(4-fluorophenyl)-2-oxo-1,2-dihydrospiro[pyrido[2,3-b][1,4]oxazine-3,3'-pyrrolidine]-1'-carbonitrile;

7-(3-fluorophenyl)-2-oxo-1,2-dihydrospiro[pyrido[2,3-b][1,4]oxazine-3,3-pyrrolidine]-1'-carbonitrile;

2-oxo-6-phenyl-1,2-dihydrospiro[pyrido[2,3-b][1,4]oxazine-3,3'-pyrrolidine]-1'-carbonitrile;

2-oxo-1,4-dihydro-2H-spiro[pyrido[2,3-b]pyrazine-3,3'-pyrrolidine]-1'-carbonitrile;

2-oxo-6-(trifluoromethyl)-1,4-dihydro-2H-spiro[pyrido[2,3-b]pyrazine-3,3'-pyrrolidine]-1'-carbonitrile;

2-oxo-7-phenyl-1,4-dihydro-2H-spiro[pyrido[2,3-b]pyrazine-3,3'-pyrrolidine]-1-carbonitrile;

7-(4-cyanophenyl)-2-oxo-1,4-dihydro-2H-spiro[pyrido[2,3-b]pyrazine-3,3'-pyrrolidine]-1'-carbonitrile;

7-(4-fluorophenyl)-2-oxo-1,4-dihydro-2H-spiro[pyrido[2,3-b]pyrazine-3,3'-pyrrolidine]-1'-carbonitrile;

7-(3-fluorophenyl)-2-oxo-1,4-dihydro-2H-spiro[pyrido[2,3-b]pyrazine-3,3'-pyrrolidine]-1'-carbonitrile;

3-oxo-3,4-dihydro-1H-spiro[pyrido[2,3-b]pyrazine-2,3'-pyrrolidine]-1'-carbonitrile;

(S)-2-oxo-7-phenyl-1,2-dihydrospiro[pyrido[2,3-b][1,4]oxazine-3,3'-pyrrolidine]-1'-carbonitrile;

(S)-2-oxo-1,2-dihydrospiro[pyrido[2,3-b][1,4]oxazine-3,3'-pyrrolidine]-1'-carbonitrile;

(S)-2-oxo-1,4-dihydro-2'H-spiro[pyrido[2,3-b]pyrazine-3,3'-pyrrolidine]-1'-carbonitrile;

(R)-2'-oxo-6'-phenyl-1,4'-dihydro-2'H-spiro[pyrrolidine-3,3'-quinoline]-1-carbonitrile;

(S)-2-oxo-7-phenyl-1,4-dihydro-2H-spiro[pyrido[2,3-b]pyrazine-3,3'-pyrrolidine]-1'-carbonitrile;

(S)-7-(3-fluorophenyl)-2-oxo-1,2-dihydrospiro[pyrido[2,3-b][1,4]oxazine-3,3'-pyrrolidine]-1'-carbonitrile;

(S)-7-(4-cyanophenyl)-2-oxo-1,2-dihydrospiro[pyrido[2,3-b][1,4]oxazine-3,3'-pyrrolidine]-1'-carbonitrile;

(S)-7-(3-cyanophenyl)-2-oxo-1,2-dihydrospiro[pyrido[2,3-b][1,4]oxazine-3,3'-pyrrolidine]-1'-carbonitrile;

(S)-7-(4-fluorophenyl)-2-oxo-1,4-dihydro-2H-spiro[pyrido[2,3-b]pyrazine-3,3'-pyrrolidine]-1'-carbonitrile;

(S)-7-(3-fluorophenyl)-2-oxo-1,4-dihydro-2H-spiro[pyrido[23-b]pyrazine-3,3'-pyrrolidine]-1'-carbonitrile;

(S)-7-(4-fluorophenyl)-2-oxo-1,2-dihydrospiro[pyrido[2,3-b][1,4]oxazine-3,3'-pyrrolidine]-1'-carbonitrile;

(S)-7-(3-cyanophenyl)-2-oxo-1,4-dihydro-2H-spiro[pyrido[2,3-b]pyrazine-3,3'-pyrrolidine]-1'-carbonitrile;

2-oxo-1,5-dihydro-2H-spiro[benzo[e][1,4]oxazepine-3,3'-pyrrolidine]-1'-carbonitrile;

2-oxo-1,2,4,5-tetrahydrospiro[pyrido[2,3-b][1,4]diazepine-3,3'-pyrrolidine]-1'-carbonitrile;

2-oxo-6-phenyl-1,4-dihydro-2H-spiro[pyrido[2,3-b]pyrazine-3,3'-pyrrolidine]-1'-carbonitrile;
7-(5-methyl-1H-indazol-4-yl)-2-oxo-1,4-dihydro-2H-spiro[pyrido[2,3-b]pyrazine-3,3'-pyrrolidine]-1'-carbonitrile;
7-(1,4-dimethyl-1H-pyrazol-5-yl)-2-oxo-1,4-dihydro-2H-spiro[pyrido[2,3-b]pyrazine-3,3'-pyrrolidine]-1'-carbonitrile;
(R)-7'-(5-methyl-1H-indazol-4-yl)-2'-oxo-1',4'-dihydro-2'H-spiro[pyrrolidine-3,3'-quinoline]-1-carbonitrile;
7'-(1H-indazol-4-yl)-2'-oxo-1',4'-dihydro-2'H-spiro[pyrrolidine-3,3'-quinoline]-1-carbonitrile;
6'-(1H-indazol-4-yl)-2'-oxo-1',4'-dihydro-2'H-spiro[pyrrolidine-3,3'-quinoline]-1-carbonitrile;
1'-cyano-N-(4-fluorophenyl)-2-oxo-1,2-dihydrospiro[pyrido[2,3-b][1,4]oxazine-3,3'-pyrrolidine]-6-carboxamide;
2-oxo-6-(piperidine-1-carbonyl)-1,2-dihydrospiro[pyrido[2,3-b][1,4]oxazine-3,3'-pyrrolidine]-1'-carbonitrile;
7-(1H-indazol-4-yl)-2-oxo-1,2-dihydrospiro[pyrido[2,3-b][1,4]oxazine-3,3'-pyrrolidine]-1'-carbonitrile;
6-(1H-indazol-4-yl)-2-oxo-1,2-dihydrospiro[pyrido[2,3-b][1,4]oxazine-3,3-pyrrolidine]-1'-carbonitrile;
1'-cyano-2-oxo-N-phenyl-1,2-dihydrospiro[pyrido[2,3-b][1,4]oxazine-3,3'-pyrrolidine]-6-carboxamide;
1'-cyano-N-(2-fluorophenyl)-2-oxo-1,2-dihydrospiro[pyrido[2,3-b][1,4]oxazine-3,3'-pyrrolidine]-6-carboxamide;
7-(1-methyl-1H-indazol-4-yl)-2-oxo-1,2-dihydrospiro[pyrido[2,3-b][1,4]oxazine-3,3'-pyrrolidine]-1'-carbonitrile;
7-(1-(2-hydroxyethyl)-1H-indazol-4-yl)-2-oxo-1,2-dihydrospiro[pyrido[2,3-b][1,4]oxazine-3,3'-pyrrolidine]-1'-carbonitrile;
7-(1-(2-methoxyethyl)-1H-indazol-4-yl)-2-oxo-1,2-dihydrospiro[pyrido[2,3-b][1,4]oxazine-3,3'-pyrrolidine]-1'-carbonitrile;
7-methoxy-2-methylpyridin-3-yl)-2-oxo-1,2-dihydrospiro[pyrido[2,3-b][1,4]oxazine-3,3'-pyrrolidine]-1'-carbonitrile;
2'-oxo-7'-(3-(trifluoromethoxy)phenyl)-1',4'-dihydro-2'H-spiro[pyrrolidine-3,3'-quinoline]-1-carbonitrile;
4-(1-cyano-2'-oxo-1',4'-dihydro-2'H-spiro[pyrrolidine-3,3'-quinolin]-7'-yl)-N,N-dimethylbenzamide;
7'-(3-(4-methylpiperazine-1-carbonyl)phenyl)-2'-oxo-1',4'-dihydro-2'H-spiro[pyrrolidine-3,3'-quinoline]-1-carbonitrile;
7'-(1-methyl-1H-pyrrol-2-yl)-2'-oxo-1',4'-dihydro-2'H-spiro[pyrrolidine-3,3'-quinoline]-1-carbonitrile;
6'-([1,1'-biphenyl]-4-yl)-2'-oxo-1',4'-dihydro-2'H-spiro[pyrrolidine-3,3'-quinoline]-1-carbonitrile;
6'-(4-(benzyloxy)phenyl)-2'-oxo-1',4'-dihydro-2'H-spiro[pyrrolidine-3,3'-quinoline]-1-carbonitrile;
6'-(1-methyl-1H-pyrazol-5-yl)-2'-oxo-1',4'-dihydro-2'H-spiro[pyrrolidine-3,3'-quinoline]-1-carbonitrile;
2'-oxo-6'-(3-(trifluoromethoxy)phenyl)-1',4'-dihydro-2'H-spiro[pyrrolidine-3,3'-quinoline]-1-carbonitrile;
2'-oxo-6'-(4-phenoxyphenyl)-1,4'-dihydro-2'H-spiro[pyrrolidine-3,3'-quinolin]-1-carbonitrile;
6'-(1-methyl-1H-pyrazol-4-yl)-2'-oxo-1',4'-dihydro-2'H-spiro[pyrrolidine-3,3'-quinoline]-1-carbonitrile;
5-(1-cyano-2'-oxo-1',4'-dihydro-2'H-spiro[pyrrolidine-3,3'-quinolin]-6'-yl)-N-methylpicolinamide;
6'-(2-(benzyloxy)phenyl)-2'-oxo-1',4'-dihydro-2'H-spiro[pyrrolidine-3,3'-quinoline]-1-carbonitrile;
4-(1-cyano-2'-oxo-1',4'-dihydro-2'H-spiro[pyrrolidine-3,3'-quinolin]-6'-yl)-N-methylbenzamide;
6'-(5-isopropyl-2-methoxyphenyl)-2'-oxo-1',4'-dihydro-2'H-spiro[pyrrolidine-3,3'-quinoline]-1-carbonitrile;
6'-(3-((2-chlorobenzyl)oxy)phenyl)-2'-oxo-1',4'-dihydro-2'H-spiro[pyrrolidine-3,3'-quinoline]-1-carbonitrile;
6'-(6-methoxypyridin-3-yl)-2'-oxo-1',4'-dihydro-2'H-spiro[pyrrolidine-3,3'-quinoline]-1-carbonitrile;
6'-(5-fluoro-2-isopropoxyphenyl)-2'-oxo-1',4'-dihydro-2'H-spiro[pyrrolidine-3,3'-quinoline]-1-carbonitrile;
6'-(3-methyl-1H-indazol-6-yl)-2'-oxo-1',4'-dihydro-2'H-spiro[pyrrolidine-3,3'-quinoline]-1-carbonitrile;
6'-(4-(4-methylpiperazine-1-carbonyl)phenyl)-2'-oxo-1',4'-dihydro-2'H-spiro[pyrrolidine-3,3'-quinoline]-1-carbonitrile;
6'-(1-methyl-1H-indazol-5-yl)-2'-oxo-1',4'-dihydro-2'H-spiro[pyrrolidine-3,3'-quinoline]-1-carbonitrile;
6'-(5-methyl-1H-indazol-4-yl)-2'-oxo-1',4'-dihydro-2'H-spiro[pyrrolidine-3,3'-quinoline]-1-carbonitrile;
N-(3-(1-cyano-2'-oxo-1',4'-dihydro-2'H-spiro[pyrrolidine-3,3'-quinolin]-6'-yl)phenyl)cyclopropanesulfonamide;
4-(1-cyano-2'-oxo-1',4'-dihydro-2'H-spiro[pyrrolidine-3,3'-quinolin]-6'-yl)-N,N-dimethylbenzamide;
2'-oxo-6'-(pyrimidin-5-yl)-1',4'-dihydro-2'H-spiro[pyrrolidine-3,3'-quinoline]-1-carbonitrile;
N-(3-(1-cyano-2'-oxo-1',4'-dihydro-2'H-spiro[pyrrolidine-3,3'-quinolin]-6'-yl)phenyl)acetamide;
N-(4-(1-cyano-2'-oxo-1',4'-dihydro-2'H-spiro[pyrrolidine-3,3'-quinolin]6'-yl)phenyl)acetamide;
6'-(3-(4-methylpiperazine-1-carbonyl)phenyl)-2'-oxo-1',4'-dihydro-2'H-spiro[pyrrolidine-3,3'-quinoline]-1-carbonitrile;
6'-(1-methyl-1H-pyrrol-2-yl)-2'-oxo-1',4'-dihydro-2'H-spiro[pyrrolidine-3,3'-quinoline]-1-carbonitrile;
6'-(4-(morpholinosulfonyl)phenyl)-2'-oxo-1',4'-dihydro-2'H-spiro[pyrrolidine-3,3'-quinoline]-1-carbonitrile;
6'-(3,5-dimethyl-1H-pyrazol-4-yl)-2'-oxo-1',4'-dihydro-2'H-spiro[pyrrolidine-3,3'-quinoline]-1-carbonitrile;
2'-oxo-6'-(3-(piperidin-1-yl)phenyl)-1',4'-dihydro-2'H-spiro[pyrrolidine-3,3'-quinoline]-1-carbonitrile;
N-(2-(1-cyano-2'-oxo-1',4'-dihydro-2'H-spiro[pyrrolidine-3,3'-quinolin]-6'-yl)phenyl)acetamide;
6'-(4-(morpholine-4-carbonyl)phenyl)-2'-oxo-1',4'-dihydro-2'H-spiro[pyrrolidine-3,3'-quinoline]-1-carbonitrile;
6'-(3-(morpholinosulfonyl)phenyl)-2'-oxo-1',4'-dihydro-2'H-spiro[pyrrolidine-3,3'-quinoline]-1-carbonitrile;
6'-(1-methyl-6-oxo-1,6-dihydropyridin-3-yl)-2'-oxo-1',4'-dihydro-2'H-spiro[pyrrolidine-3,3'-quinoline]-1-carbonitrile;
6'-(2-methylbenzo[d]thiazol-5-yl)-2'-oxo-1',4'-dihydro-2i-spiro[pyrrolidine-3,3'-quinoline]-1-carbonitrile;
6'-(3,5-dimethylisoxazol-4-yl)-2'-oxo-1',4'-dihydro-2'H-spiro[pyrrolidine-3,3'-quinoline]-1-carbonitrile;
6'-(2-chloro-5-(trifluoromethoxy)phenyl)-2'-oxo-1',4'-dihydro-2'H-spiro[pyrrolidine-3,3'-quinoline]-1-carbonitrile;
6'-(4-(4-methylpiperazin-1-yl)phenyl)-2'-oxo-1',4'-dihydro-2'H-spiro[pyrrolidine-3,3'-quinoline]-1-carbonitrile;
N-benzyl-4-(1-cyano-2'-oxo-1',4'-dihydro-2'H-spiro[pyrrolidine-3,3'-quinolin]-6'-yl)benzamide;
6'-(3-methyl-1H-pyrazol-4-yl)-2'-oxo-1',4'-dihydro-2'H-spiro[pyrrolidine-3,3'-quinoline]-1-carbonitrile;
6'-(4-(morpholinomethyl)phenyl)-2'-oxo-1',4'-dihydro-2'H-spiro[pyrrolidine-3,3'-quinoline]-1-carbonitrile;
3-(1-cyano-2'-oxo-1',4'-dihydro-2¹H-spiro[pyrrolidine-3,3'-quinolin]-6'-yl)-N,N-dimethylbenzamide; and 6'-(2-methylpyridin-4-yl)-2'-oxo-1',4'-dihydro-2'H-spiro[pyrrolidine-3,3'-quinoline]-1-carbonitrile;
a tautomer thereof, or a pharmaceutically acceptable salt of said compound or tautomer.

10. A pharmaceutical composition comprising a compound of formula (I) as defined in claim 1, a tautomer thereof, or a pharmaceutically acceptable salt of said compound or tautomer, together with one or more pharmaceutically acceptable excipients.

\* \* \* \* \*